(12) United States Patent
Ying et al.

(10) Patent No.: US 7,211,275 B2
(45) Date of Patent: May 1, 2007

(54) COMPOSITE MATERIALS FOR CONTROLLED RELEASE OF WATER SOLUBLE PRODUCTS

(75) Inventors: Jackie Y. Ying, Winchester, MA (US); Tseh-Hwan Yong, Somerville, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 11/034,217

(22) Filed: Jan. 13, 2005

(65) Prior Publication Data

US 2006/0024377 A1    Feb. 2, 2006

Related U.S. Application Data

(60) Provisional application No. 60/536,710, filed on Jan. 16, 2004.

(51) Int. Cl.
*A61K 9/58* (2006.01)

(52) U.S. Cl. ............... 424/462; 424/457; 424/458; 424/470; 424/482; 514/12

(58) Field of Classification Search ............... None
See application file for complete search history.

(56) References Cited

U.S. PATENT DOCUMENTS

| 5,955,529 | A * | 9/1999 | Imai et al. ............ 524/417 |
| 6,767,928 | B1 * | 7/2004 | Murphy et al. ......... 521/51 |
| 2002/0086842 | A1 * | 7/2002 | Plank et al. ............ 514/44 |

* cited by examiner

*Primary Examiner*—Robert A. Wax
(74) *Attorney, Agent, or Firm*—Pearl, Cohen, Zedek, Latzer, LLP; Mark S. Cohen

(57) ABSTRACT

Composite materials comprising a water-soluble compound adsorbed onto a basic inorganic material and a bio-degradable polymer which yields acidic degradation products, methods of producing same, and methods of use thereof are described, wherein the composite materials are designed so as to provide controlled release of the water soluble molecule.

53 Claims, 28 Drawing Sheets

COMPOSITE MATERIALS FOR CONTROLLED RELEASE OF WATER SOLUBLE PRODUCTS

CROSS REFERENCE TO RELATED APPLICATIONS

This Application claims priority from U.S. Provisional Application Ser. No. 60/536,710, filed Jan. 16, 2004, which is hereby incorporated in its entirety.

FIELD OF THE INVENTION

This invention provides a composite material, comprising a water-soluble molecule, designed so as to provide controlled release of the water-soluble molecule. Uses of the composite material for drug, protein and gene delivery are described, as well as applications in tissue engineering.

BACKGROUND OF THE INVENTION

A variety of sustained release formulations for delivery of water-soluble products such as drugs, proteins and nucleic acids are known in the art. Among these are techniques for the preparation of polymer microspheres, via spray drying, spray congealing, coacervation, or solvent evaporation, which provide for the sustained release of encapsulated bioactive materials. Many encapsulation techniques utilize polymers dissolved in an organic medium and then emulsified in water, a so-called oil-in-water process (O/W), for encapsulating water-soluble material. Water-soluble products partition into an aqueous medium, however, and in general, such methods result in low encapsulation efficiency. Similarly, encapsulation via water-in-oil-in-water or oil-in-oil (O/O) emulsion processes suffer limitations including the use of different organic solvents, first to solubilize the polymer, and then to wash the polymer microspheres free of the oil in which they are formed, and subsequent removal of the solvents.

A major complicating factor in achieving high encapsulation efficiency of peptides, nucleic acids and some drugs is their water solubility. Solubility of, for example, peptides is considerably reduced, however, when the peptide is present as a free base, due to intermolecular interactions. One method of enhancing the encapsulation efficiency of the peptides in an O/W process is by using a peptide as a free base adsorbed onto a bioresorbable inorganic matrix, however, pH conditions must be carefully maintained, or the solubilization of the peptide may occur, leading to poor encapsulation efficiency. In addition, such encapsulation does not provide a controlled release mechanism.

Thus there remains a need for high loading, controlled release mechanisms in microencapsulated water-soluble products.

SUMMARY OF THE INVENTION

In one embodiment, the invention provides a controlled release composite, comprising a basic, inorganic material, a water-soluble compound adsorbed onto the inorganic material and a bio-degradable polymer which yields acidic degradation products, wherein acidic degradation products from the polymer facilitate dissolution of said basic inorganic material, releasing the water-soluble compound. In one embodiment, the water-soluble compound is a peptide, a protein, a nucleic acid or a drug. In another embodiment, the peptide or protein is osteogenic, chondrogenic or angiogenic. In one embodiment, the basic inorganic material is hydroxyapatite, carbonated apatite, calcium phosphate, calcium carbonate, zinc oxide, magnesium oxide, or alumina. In another embodiment, the bio-degradable polymer is a poly($\alpha$-hydroxyacid), such as poly(lactic acid), poly(glycolic acid), or blends thereof, a poly(orthoester), or a poly (anhydride), or a poly(hydroxyl alkanoate).

In another embodiment, the composite may be in the form of a particle, which in another embodiment is a micropaticle or a nanoparticle. In one embodiment, the composite may be in the form of a gel, bulk scaffold, thin film or pellet, or in another embodiment, the gel, bulk scaffold, thin film or pellet may further comprise particles of this invention.

In another embodiment, the composite may further comprise an amphoteric species, which alters the rate of dissolution of said basic inorganic material, liberation of said adsorbed compound, or a combination thereof. In another embodiment, the *amphoteric* species serves as a diffusion barrier to the liberated compound.

In one embodiment, the biodegradable polymer concentration, molecular weight, or combination thereof, is varied. In another embodiment, biodegradable polymer comprises a blend of at least 2 polymers, which, in another embodiment, differ in their hydrophobicity, or in another embodiment, are varied in terms of their concentration.

In another embodiment, this invention provides a process for preparing a composite scaffolding comprising a water-soluble compound, comprising the steps of (a) adsorbing a water-soluble compound onto a basic, inorganic material, (b) combining the product in (a) with a solution of a bio-degradable polymer which yields acidic degradation products to form a solid-in-oil emulsion, (c) precipitating the composite scaffolding product in (b), and (d) isolating the composite scaffolding.

In another embodiment, this invention provides a method of controlled release of a therapeutic compound to a subject, comprising administering to the subject a controlled release composite comprising a therapeutic water-soluble compound adsorbed onto a basic, inorganic material and a bio-degradable polymer which yields acidic degradation products, whereby degradation of said polymer yields acidic degradation products therefrom, which stimulates dissolution of the inorganic material and release of said therapeutic compound over a period of time, thereby being a method of controlled release of a therapeutic water-soluble compound.

In one embodiment, the therapeutic compound is a peptide, a protein, a nucleic acid or a drug. In another embodiment, the therapeutic compound is osteogenic, chondrogenic or angiogenic. In another embodiment, the therapeutic compound is an antibacterial, antiviral, antifungal or antiparasitic compound. In another embodiment, the therapeutic compound has cytotoxic or anti-cancer activity. In another embodiment, the therapeutic compound is an enzyme, a receptor, a channel protein, a hormone, a cytokine or a growth factor. In another embodiment, the therapeutic compound is immunostimulatory. In another embodiment, the therapeutic compound inhibits inflammatory or immune responses.

In another embodiment, dissolution of the basic inorganic material releases charged species over a course of time. In one embodiment, the charged species are therapeutic, and in another embodiment, comprise calcium or phosphate, or a combination thereof. In another embodiment, the charged species are osteogenic, or in another embodiment, the charged species promote tissue repair.

In another embodiment, this invention provides a method of tissue engineering comprising the step of contacting a cell with a composite scaffolding comprising a water-soluble tissue-promoting factor adsorbed onto a basic, inorganic material and a bio-degradable polymer which yields acidic degradation products, whereby degradation of the polymer yields acidic degradation products therefrom, which stimulates dissolution of the inorganic material and release of the water-soluble tissue-promoting factor, and whereby the cell responds to the tissue-promoting factor, promoting tissue formation, thereby providing a method of tissue engineering. In one embodiment, the tissue is bone or cartilage. In another embodiment, the tissue-promoting factor is a bone morphogenetic protein, a member of the TGF-β superfamily, or a member of the BMP signaling cascade. In another embodiment, release of the water-soluble tissue-promoting factor occurs over a period of time.

In another embodiment, this invention provides a method of stimulating or enhancing bone repair, or maintaining or increasing bone volume, bone quality, or bone strength in the body of a subject in need, comprising the steps of: contacting a cell in the subject with a composite controlled release system comprising a water-soluble osteogenesis-promoting factor adsorbed onto a basic, inorganic material and a bio-degradable polymer which yields acidic degradation products, whereby degradation of the polymer yields acidic degradation products therefrom, which stimulates dissolution of the inorganic material and release of the water-soluble osteogenesis-promoting factor, and whereby the cell responds to the tissue-promoting factor, promoting bone formation, thereby providing a method of stimulating or enhancing bone repair, or maintaining or increasing bone volume, bone quality, or bone strength in the body of a subject in need. In one embodiment, release of the water-soluble osteogenesis-promoting factor occurs over a period of time.

In another embodiment, this invention provides a method of nucleic acid delivery, comprising contacting a cell with a composite controlled release system comprising a nucleic acid adsorbed onto a basic, inorganic material and a bio-degradable polymer which yields acidic degradation products, whereby degradation of the polymer yields acidic degradation products therefrom, which stimulates dissolution of the inorganic material and release of the nucleic acid, thereby being a method of nucleic acid delivery. In one embodiment, the nucleic acid encodes for a compound, which is osteogenic, chondrogenic or angiogenic. In another embodiment, the nucleic acid encodes for an antibacterial, antiviral, antifungal or antiparasitic peptide or protein. In another embodiment, the nucleic acid encodes for a peptide or protein with cytotoxic or anti-cancer activity. In another embodiment, the nucleic acid encodes for an enzyme, a receptor, a channel protein, a hormone, a cytokine or a growth factor. In another embodiment, the nucleic acid encodes for a peptide or protein, which is immunostimulatory. In another embodiment, the nucleic acid encodes for a peptide or protein, which inhibits inflammatory or immune responses. In another embodiment, release of the nucleic acid occurs over a period of time.

BRIEF DESCRIPTION OF THE DRAWINGS

FIG. 12 A: Effect of protein loading in apatite-protein complex on protein release. Particles were fabricated from 24 kD PLGA. "20 w/w/o" particles contained 18 µg of FITC-BSA per mg carrier and "9 w/w %" particles contained 9 µg of FITC-BSA per mg carrier. (B) Effect of apatite-protein complex loading on protein release, expressed as cumulative mass of BSA released per mg carrier and (C) percentage cumulative release of BSA.

Apatite-protein loadings in composite particles were 2.0, 3.5, 10.7 and 16.7 w/w %. Particles contained 2, 3, 9 and 15 μg of FITC-BSA per mg carrier, respectively. Molecular weight of PLGA used was 24 kD. (D) Release of BSA from PLGA and PLGA+PLA microparticles prepared by the double emulsion method and (E) Release of acid from the degradation of PLGA of different molecular weights in blank composite particles over a period of 4 weeks.

Figure 13:
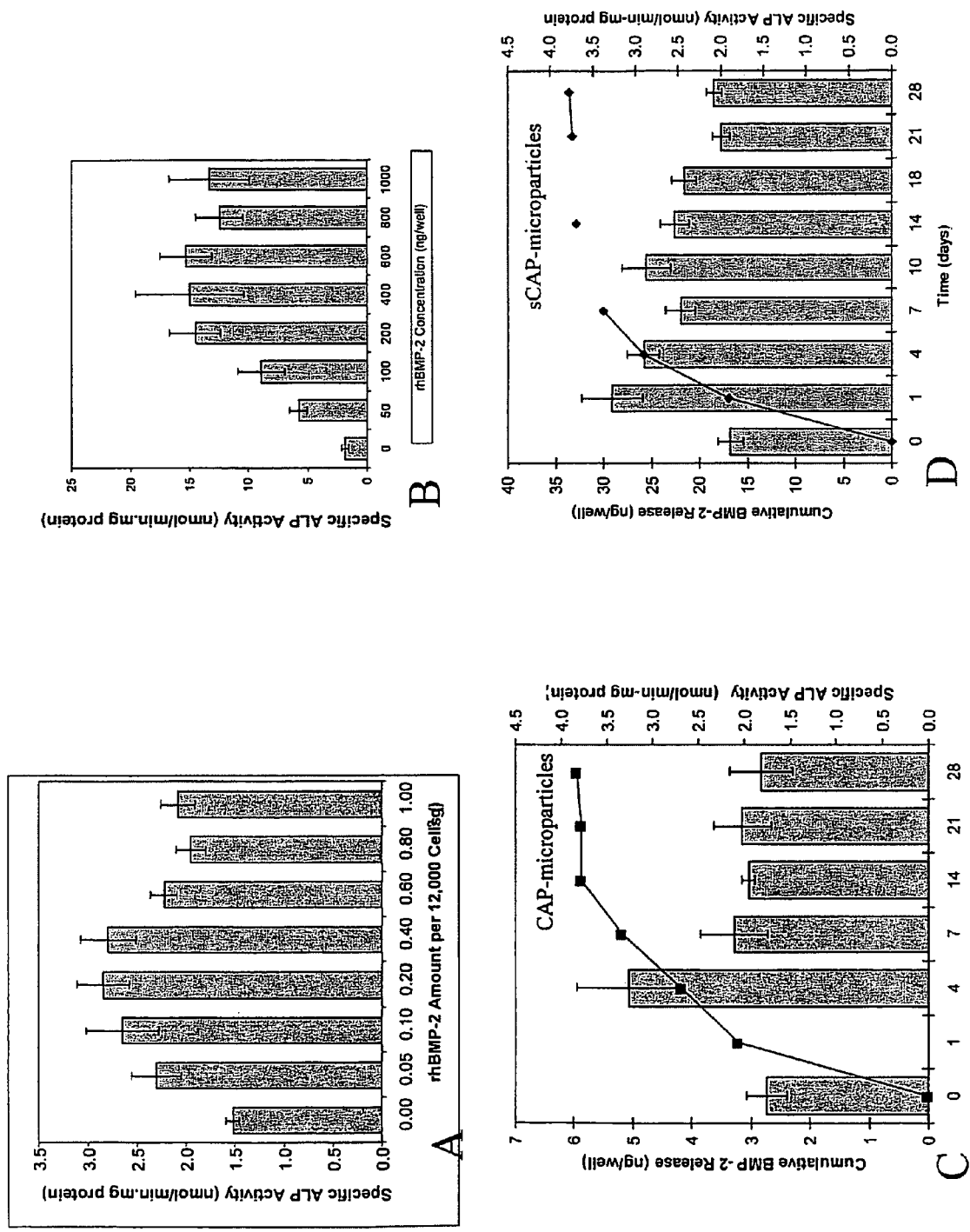

FIG. 13 demonstrates induction of alkaline phosphatase activity in C3H10T1/2 cells administered rhBMP-2 in composite microparticles. C3H10T1/2 cells administered composite microparticles containing rhBMP-2 adsorbed to CAP (C) or sCAP (D) exhibited elevated ALP activity, over time, as compared to cells provided rhBMP-2 alone (expressed as amount per 12,000 cells, (A) and (B). Each well contained 0.5 ml of medium; 50 ng/well is equivalent to 100 ng/ml of rhBMP-2. ALP activity of cell lysates measured spectroscopically at 405 nm, using a p-nitrophenyl phosphate substrate, with the reaction carried out at 37° C.

Figure 14:
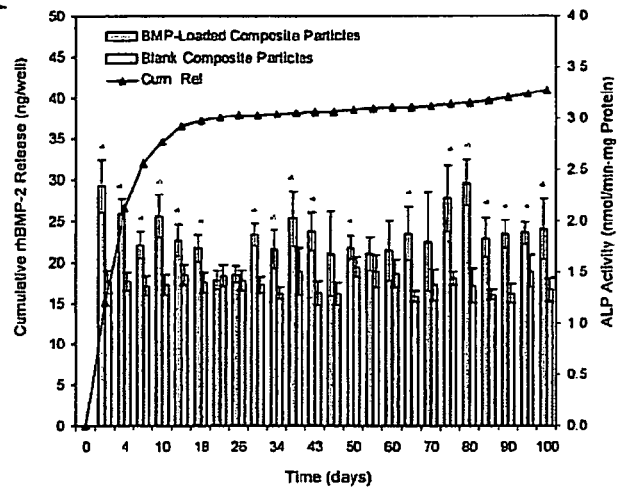
Figure 14:
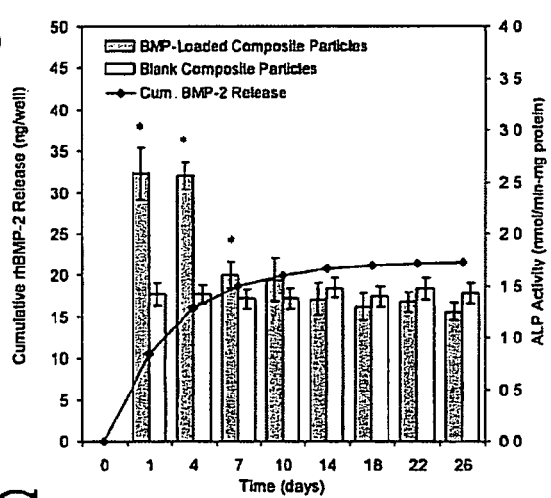
Figure 14:
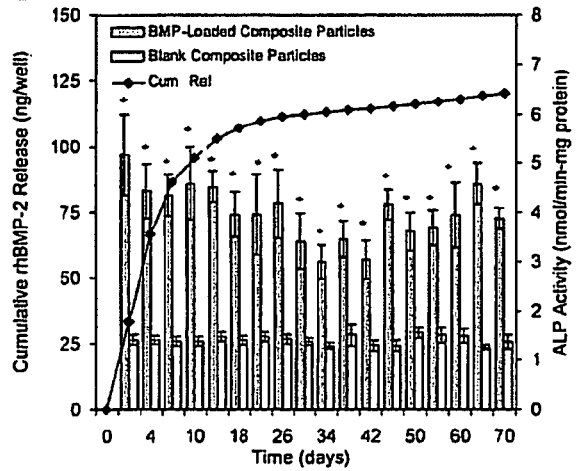

FIG. 14: ALP activity induced by release medium from rhBMP-2-loaded composite microparticles, as a function of time. An asterisk denotes statistical significance of p<0.05 by Student's t-test for n=5. Cumulative release is given in units of 'ng/well' to reflect the actual amounts to which the cells were exposed, and to facilitate comparison with FIG. 13. (A) Particles contained 145 ng of rhBMP-2 per mg of carrier, and were fabricated from 59 kD PLGA and 0.08 mg of carbonated apatite per mg of PLGA. (B) Particles contained 145 ng of rhBMP-2 per mg carrier, and were fabricated from 59 kD PLGA and 0.18 mg of carbonated apatite per mg of PLGA or (C) Particles contained 145 ng of rhBMP-2 per mg carrier, and were fabricated from a 3:2 blend of 59 kD PLGA and 25 kD PLA. Apatite loading was 0.08 mg of carbonated apatite per mg of polymer.

Figure 15:
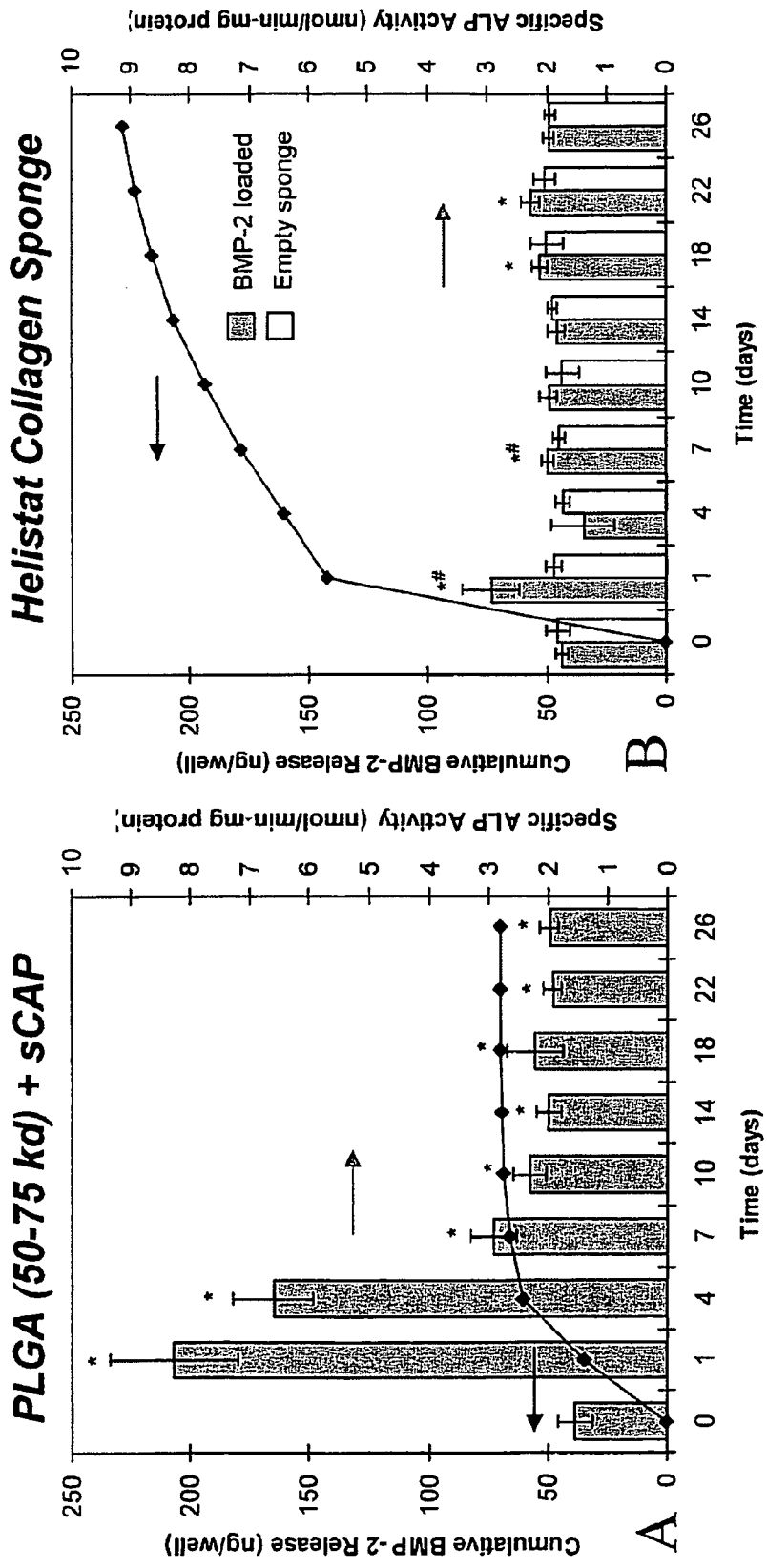
Figure 15C:
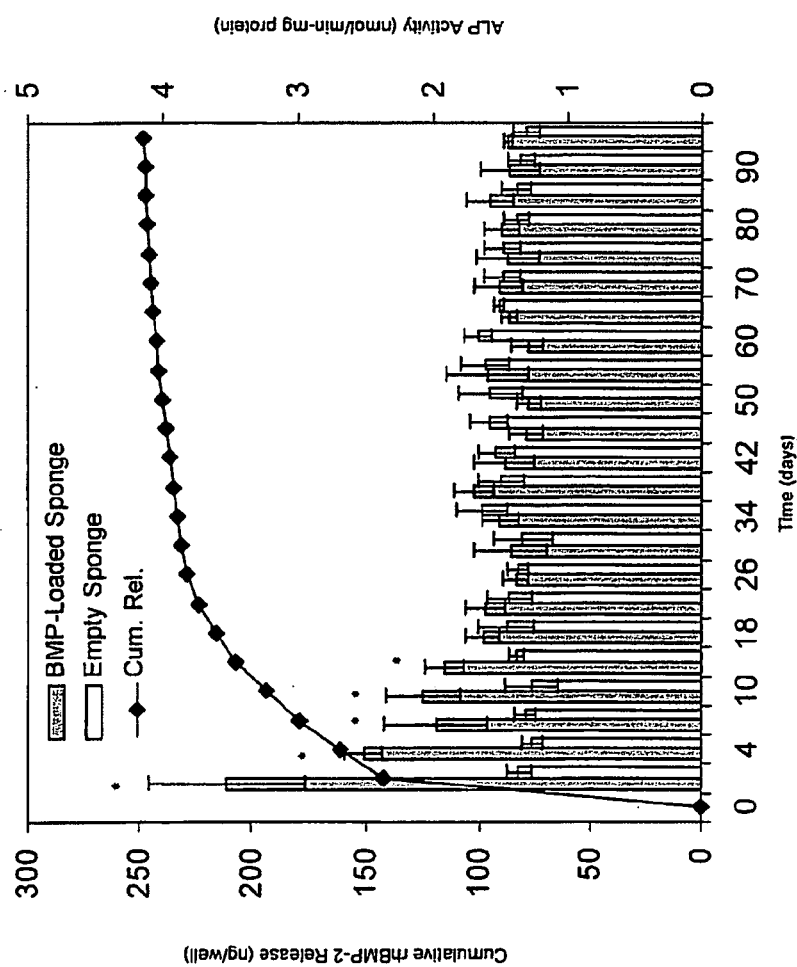

FIG. 15 demonstrates induction of alkaline phosphatase activity in C3H10T/1/2 cells administered composite microparticles comprising sCAP adsorbed rhBMP-2 and PLGA of between 50–75 kD (A), which exceeded that of BMP-2 loaded Helistat collagen sponges (B). More BMP-2 is released from composite microparticles comprising a higher polymer MW, loaded with comparable BMP-2 concentration. C. ALP activity induced by release medium collected at each time point from rhBMP-2-loaded Helistat sponges. Sponges contained 200 ng of rhBMP-2 per mg carrier.

Figure 16:
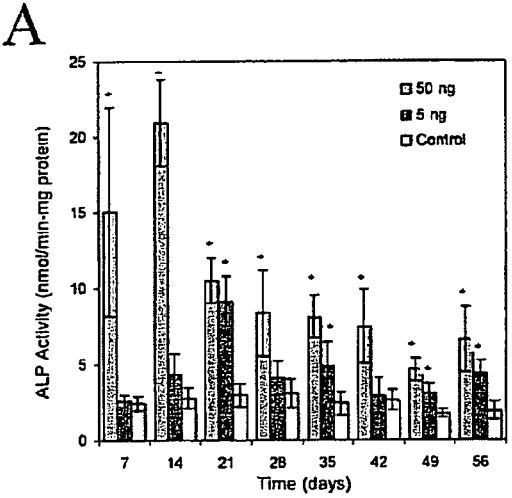
Figure 16:
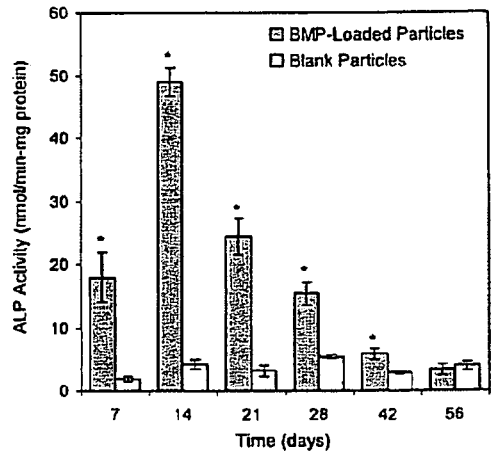
Figure 16:
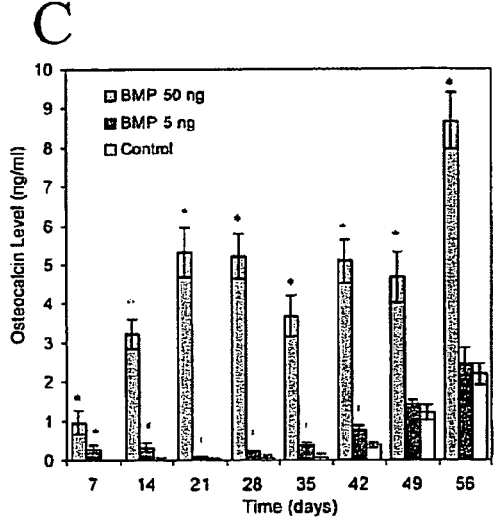
Figure 16:
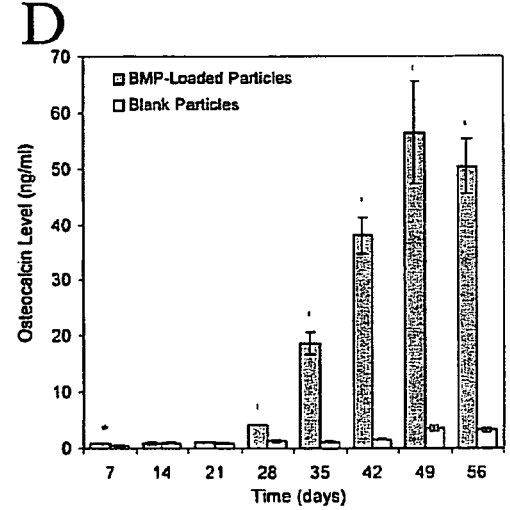

FIG. 16 Effect of length of exposure to rhBMP-2 on ALP activity. rhBMP-2 concentrations of 0 (control), 5 and 50 ng/well were used (A) and ALP activity was measured, as well as in particles containing 145 ng of rhBMP-2 per mg of carrier, fabricated from 59 kD PLGA and 0.08 mg of carbonated apatite per mg of PLGA (B). (C) Similarly, the effect of length of exposure to rhBMP-2 on osteocalcin levels, with BMP-2 concentrations being 0 (control), 5 and 50 ng of rhBMP-2 per well (C) and those containing 145 ng of rhBMP-2 per mg carrier, fabricated from 59 kD PLGA and 0.08 mg of carbonated apatite per mg of PLGA (D), were evaluated.

Figure 17:
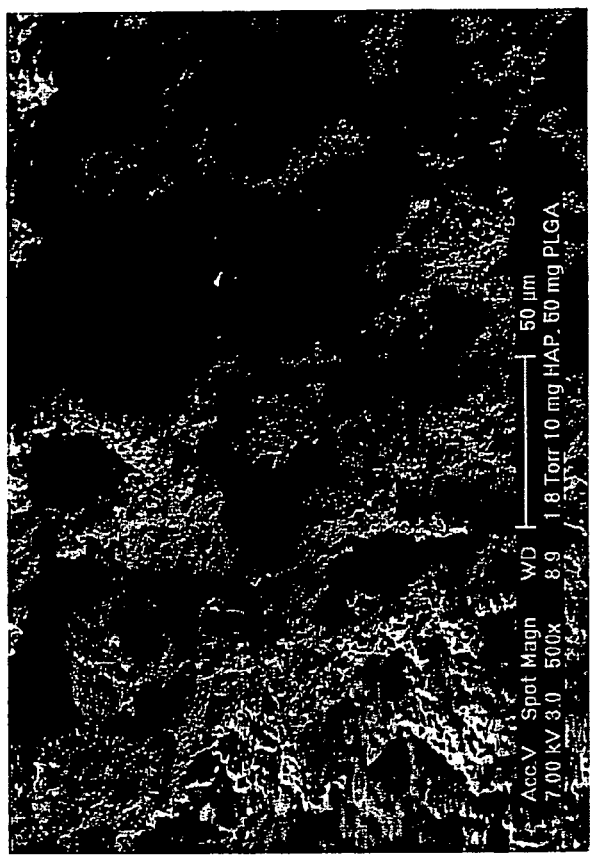
Figure 17:
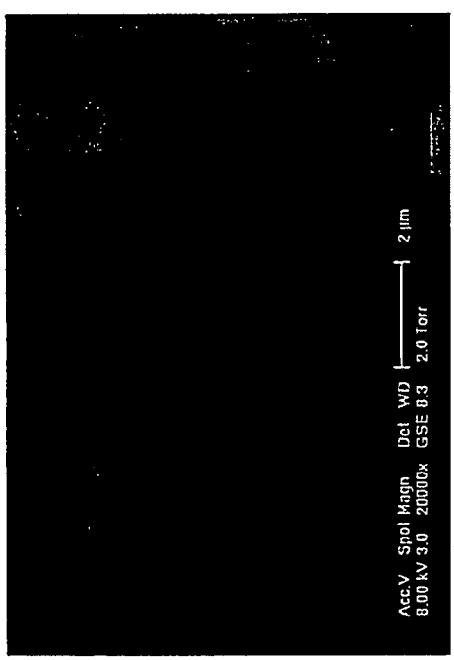
Figure 17:
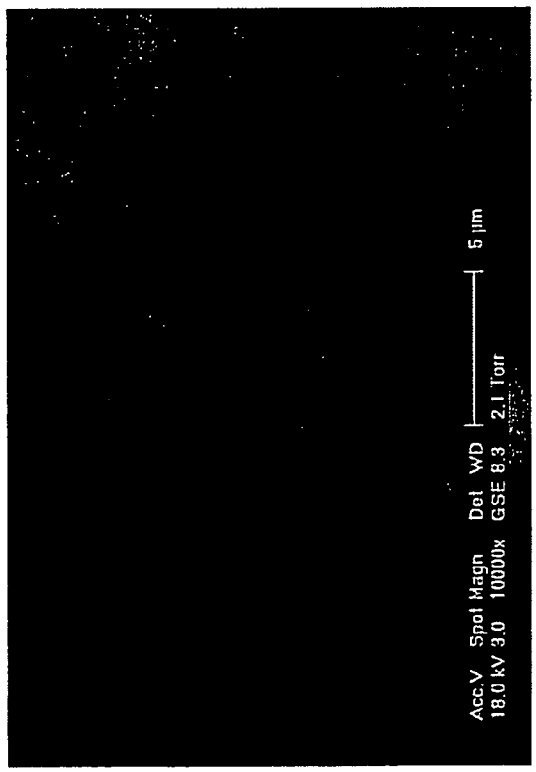

FIG. 17 demonstrates the assembly of composite microparticles into a scaffolding, visualized by ESEM. CAP power alone, or samples following the adsorption of BSA onto CAP visualized by SEM, provided a relatively amorphous aggregate (A and B, respectively), while PLGA-HAP-BSA assembled into a more organized porous scaffolding (C).

Figure 18:
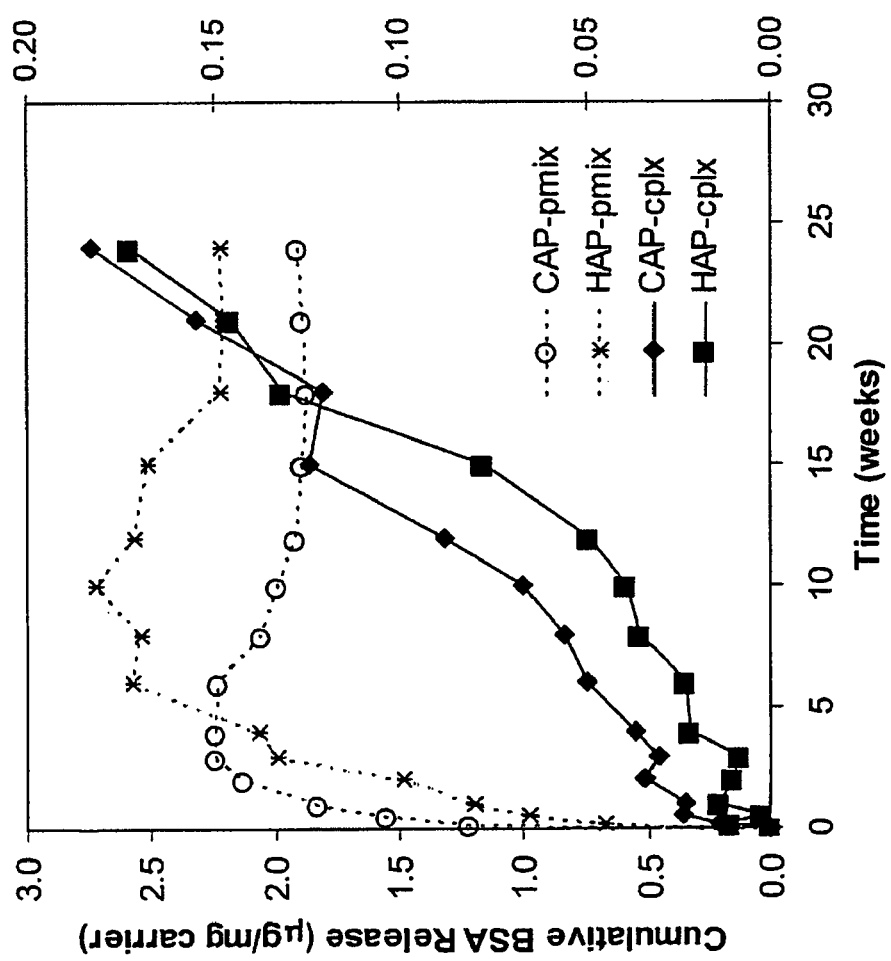

FIG. 18 demonstrates protein release from composite scaffolds containing an apatite-BSA complex (-cplx) or a physical mixture of apatite and BSA (-pmix). Scaffolds contained 20 mg of FITC-BSA per mg carrier and were constructed of 24 kD PLGA.

Figure 19:
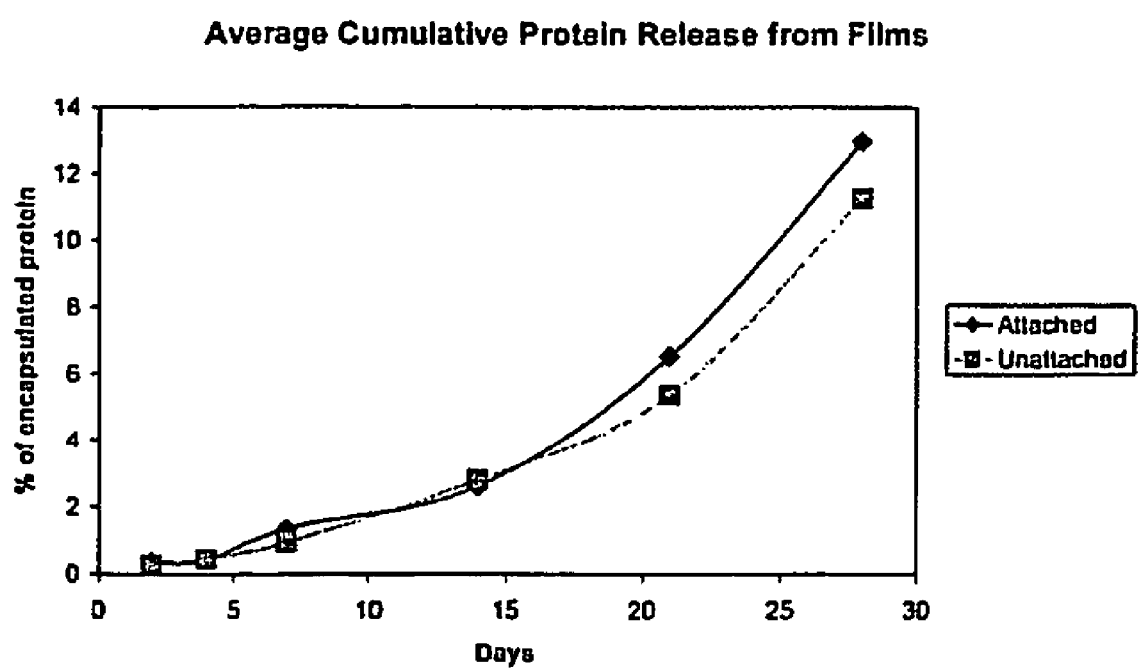

FIG. 19 demonstrates the cumulative release of FITC-BSA from composite films over 4 weeks.

Figure 20:
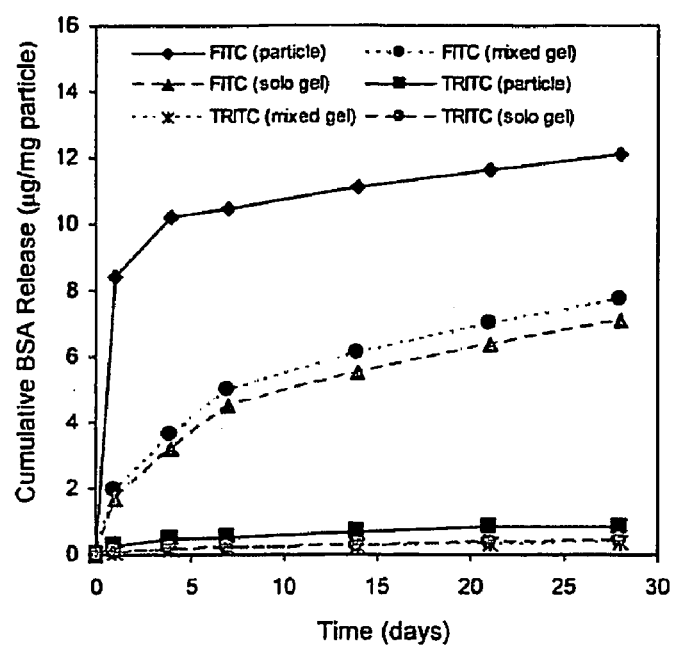

FIG. 20 demonstrates BSA release from composite particles and composite gelatin scaffolds. Protein release was normalized by the mass of the corresponding set of composite particles. Solid curves indicate release from the composite particles alone. Composite particles encapsulating FITC-BSA were fabricated from 250 mg of 6 kD PLGA and 50 mg of sCAP. Composite particles encapsulating TRITC-BSA were fabricated from 250 mg of 59 kD PLGA and 50 mg of sCAP. 'solo gel' refers to release from composite gelatin scaffolds containing one set of composite particles whereas 'mixed gel' refers to release from composite gelatin scaffolds containing an equi-mixture of the two sets of composite particles. The particle loading (28.5 w/w %), and hence, the protein content (20 μg per mg of particle, 200 μg per gel) of 'solo gels' and 'mixed gels' were the same.

Figure 21:
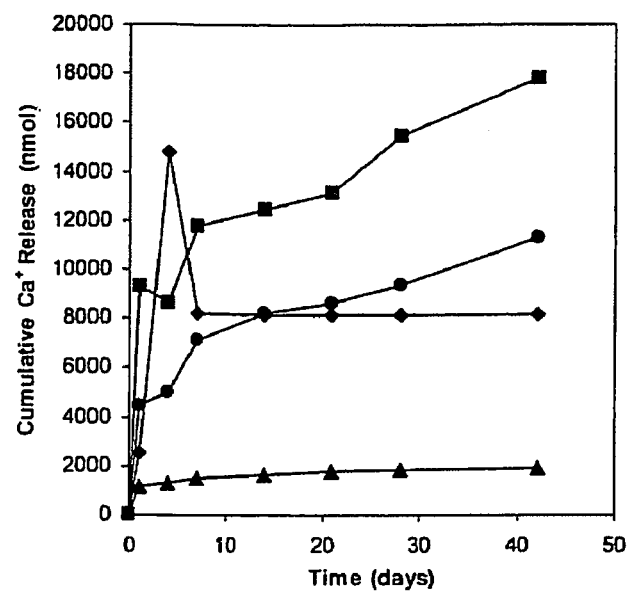

FIG. 21 demonstrates calcium release from composite microparticles prepared with 13 kD PLGA (♦), 59 kD PLGA (●), and 59 kD PLGA with loaded BSA (■). The CAP loading of the composite particles was 16.67 w/w %. Calcium release from an equivalent amount of CAP is shown by ▲.

Figure 22:
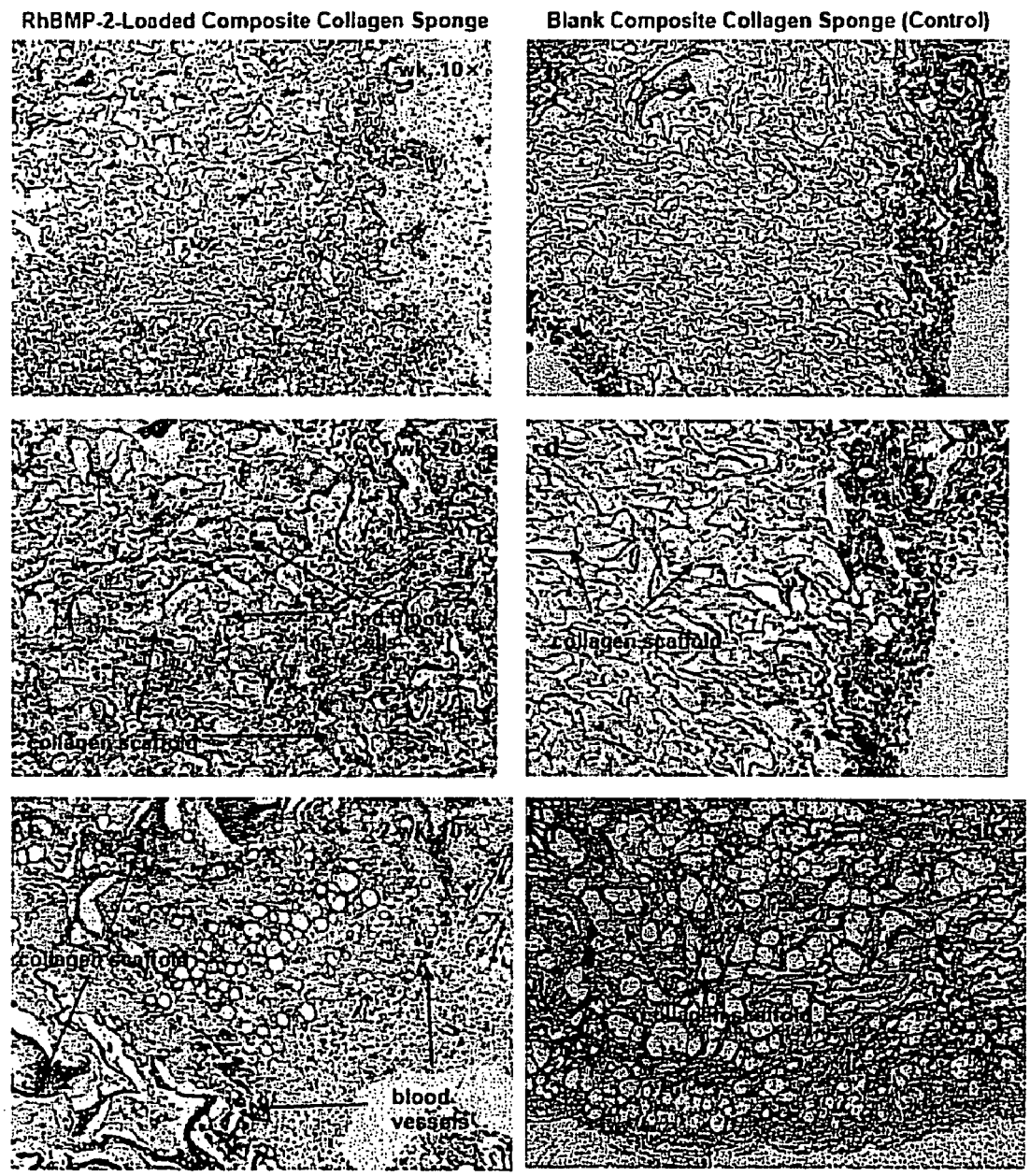

FIG. 22 demonstrates histologic changes induced by composite collagen sponges loaded with BMP-2. H & E staining of excised composite collagen sponges at 1 week (a-d) and 2 weeks (e,f). Micrographs for rhBMP-2-loaded composite collagen sponges are in the left column (a,c, and e); micrographs for blank composite collage sponges are in the right column (b, d, f). Magnification: 10× (a, b, e, and f) and 20× (c and d). Mayer's hematoxylin used for all sections except (e) which was stained with Harris' hematoxylin.

Figure 23:
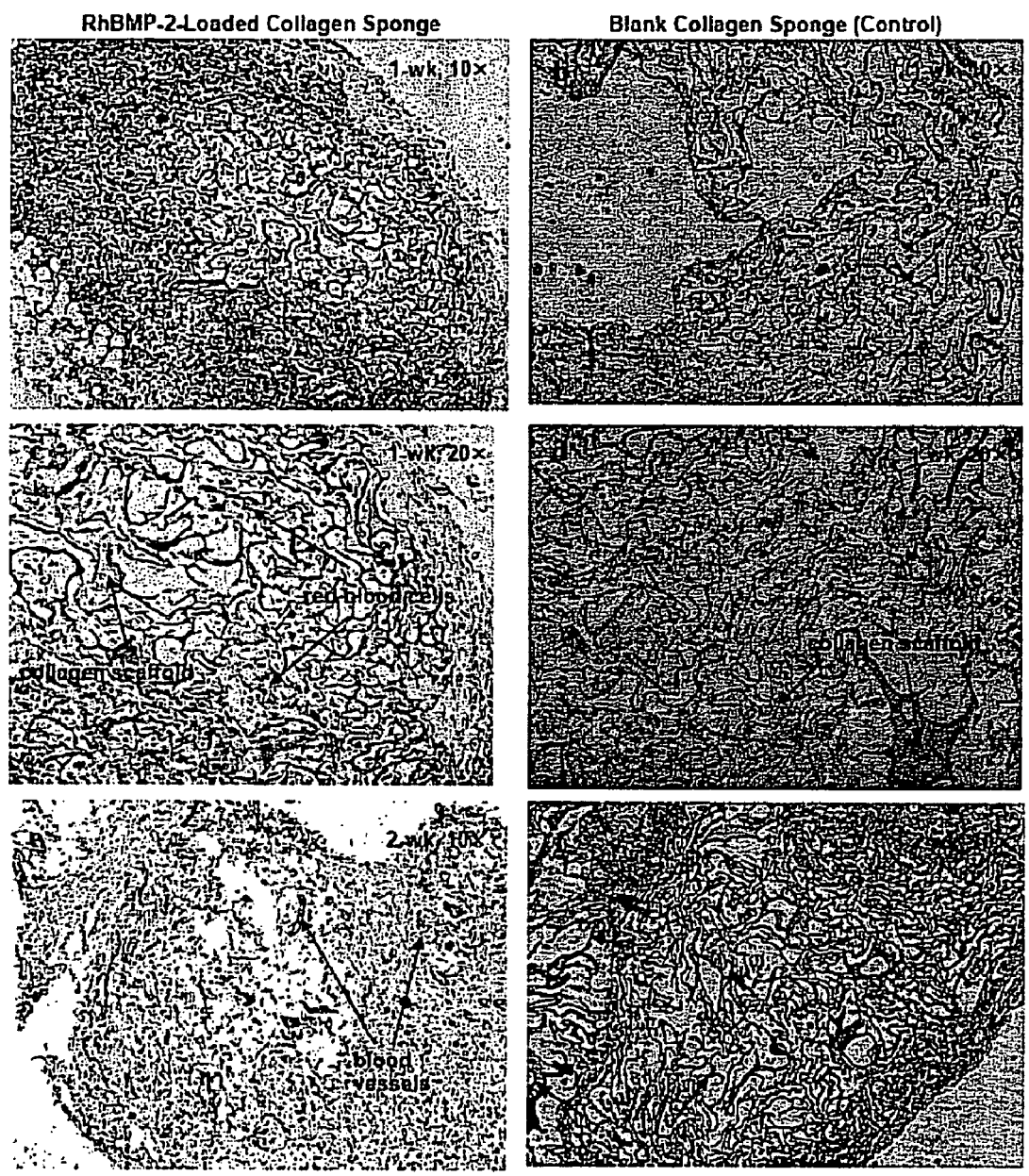

FIG. 23 demonstrates histologic changes induced by collagen sponges loaded with BMP-2. H & E staining of excised collagen sponges at 1 week (a-d) and 2 weeks (e,f). Micrographs for rhBMP-2-loaded collagen sponges are in the left column (a,c, and e); micrographs for blank collagen sponges are in the right column (b, d, f). Magnification: 10× (a, b, e, and f) and 20× (c and d). Mayer's hematoxylin used for all sections except (e) which was stained with Harris' hematoxylin.

DETAILED EMBODIMENTS OF THE INVENTION

The invention is directed to, in one embodiment, composite materials, comprising a water-soluble molecule and methods of producing same, wherein the composite materials are designed so as to provide controlled release of the water-soluble molecule.

Composite materials, also referred to, in one embodiment, as "controlled release composites", are microparticles, in another embodiment, comprising, in other embodiments, a water soluble compound, such as, in one embodiment, a protein, adsorbed onto a basic inorganic compound, and a biodegradable polymer which produces acidic degradation products, which provides sustained release of the protein, as exemplified herein, in, examples 2, 3 and 5.

In one embodiment, the invention provides a controlled release composite comprising a water-soluble compound adsorbed onto a basic, inorganic material and a bio-degradable polymer which yields acidic degradation products, wherein acidic degradation products from said polymer facilitate dissolution of said basic inorganic material, over a course of time, thereby being a composite controlled release system.

In one embodiment, the composite is in the form of a microparticle, nanoparticle, bulk scaffold, thin film, gel or pellet.

In one embodiment, a biodegradable polymer refers to a material, which is degraded in the biological environment of the cell or subject in which it is found. In one embodiment, the biodegradable polymer undergoes degradation, during which, acidic products are released. In one embodiment, bio-degradation involves the degradation of the polymer into its component subunits, via, for example, digestion, by a biochemical process. In one embodiment, biodegradation may involve cleavage of bonds (whether covalent or otherwise) in the polymer backbone. In another embodiment, biodegradation may involve cleavage of a bond (whether covalent or otherwise) internal to a side-chain or one that connects a side chain to the polymer backbone. In one embodiment, the polymeric phase is hydrolyzed, yielding acidic degradation products, which then dissolve the basic inorganic phase, and facilitate the release of the adsorbed compound.

According to this aspect of the invention, and in one embodiment, any degradation resulting in the production of acidic products may participate in the dissolution of the inorganic phase comprising the inorganic basic material onto which the water-soluble compound is adsorbed.

In another embodiment, degradation results in the production of charged species. According to this aspect of the invention, and in one embodiment, dissolution of the basic inorganic phase may result in the release of anions and cations comprising the basic inorganic phase. For example, the use of apatite as the inorganic phase will result in the release of calcium and phosphate ions, which may be useful, in another embodiment, in some chemical reactions (e.g. gelation of sodium alginate by calcium ions) or, in another embodiment, may have some useful physiological effects (e.g. calcium phosphate stimulation of osteogenesis and bone repair).

In one embodiment, this invention provides a means of controlled release of cations and anions, using the composite materials of this invention, as described, wherein said composite comprises a basic, inorganic material and a bio-degradable polymer which yields acidic degradation products, wherein dissolution of the basic inorganic material releases cations and/or anions in a controlled manner, over a period of time. In one embodiment, a water-soluble molecule of interest is adsorbed onto the basic, inorganic material. In another embodiment, composite materials may comprise the basic, inorganic material and a bio-degradable polymer which yields acidic degradation products, without additional agents or compounds adsorbed on the inorganic material. It is to be understood that any use of the composite materials of this invention wherein a controlled release of a charged species is thus effected, is to be considered as part of this invention, and an embodiment thereof.

In one embodiment, a biodegradable polymer that yields acidic degradation products may comprise bio-erodible polymers such as polyesters (for example, polylactides, poly-α-hydroxyacids, polyglycolides, polycaprolactone and copolymers and blends thereof), polycarbonates, polyorthoesters, polyacetals, polyanhydrides, their copolymers or blends. In another embodiment, the biodegradable polymer that yields acidic degradation product is a polylactide-co-glycolide. In another embodiment, the bio-degradable polymer is a poly DL-lactide, or a poly-L-lactide, or a polyglycolide. Polymers may optionally contain anionic or cationic groups.

In one embodiment, the bio-degradable polymer may be in solution containing between 1% and 100% polymer, or, in another embodiment, between 5% and 15% polymer, or in another embodiment, between 1% and 10%, or in another embodiment, between 10% and 20%, or in another embodiment, between 10% and 50%, or in another embodiment, between 25% and 50%, or in another embodiment, between 30% and 60%, or in another embodiment, between 25% and 75%, or in another embodiment, between 40% and 80%, or in another embodiment, between 10% and 50%, or in another embodiment, between 50% and 100%. The polymer solution can be prepared, in another embodiment, in dichloromethane (DCM), chloroform, ethylacetate, methylformate, dichloroethane, toluene, cyclohexane, acetone or other solvents, well known to one skilled in the art. The polymer solution may be utilized to construct the composite controlled release systems of this invention.

In one embodiment, the basic, inorganic material may comprise hydroxyapatite, carbonated apatite, calcium phosphate, zinc hydroxide, etc. In another embodiment, submicron sized particles of the inorganic material may be prepared, and in another embodiment, a surfactant may be added to reduce agglomeration in preparation of the particles. In one embodiment, the surfactant is Pluronic® F-68 (BASF Wyandotte, Wyandotte, Mich.), Pluronic® F-127 (BASF Wyandotte), Brij® 35 (ICI Americas; Wilmington, Del.), Triton® X-100 (Rohm and Haas Co., Philadelphia, Pa.), Brij® 52 (ICI Americas), Span® 20 (ICI Americas), Generol® 122 ES (Henkel Corp.), Triton® N-42 (Rohm and Haas Co.,), Triton® N-101 (Rohm and Haas Co.,), Triton®X-405 (Rohm and Haas Co.,), Tween® 80 (ICI Americas), Tween® 85 (ICI Americas), and Brij® 56 (ICI Americas).

In one embodiment, the water-soluble compound is a peptide or a protein.

According to this aspect of the invention, and in one embodiment, a protein or peptide comprises, or refers to native peptides (either degradation products, synthetically synthesized peptides or recombinant peptides) and peptidomimetics (typically, synthetically synthesized peptides), such as peptoids and semipeptoids which are peptide analogs, which may have, for example, modifications rendering the peptides more stable while in a body or more capable of penetrating into cells. Such modifications comprise, in another embodiment, N terminus modification, C terminus modification, peptide bond modification, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992).

The proteins/peptides may comprise any of the 20 naturally occurring amino acids, post-translationally modified amino acids, including, for example, hydroxyproline, phosphoserine and phosphothreonine; and others such as, for example, 2-aminoadipic acid, hydroxylysine, isodesmosine, nor-valine, nor-leucine and ornithine. In another embodiment, the proteins/peptides comprise D- or L-amino acids, or a combination thereof. In another embodiment, the protein/peptides may comprise one or more modified amino acids or one or more non-amino acid monomers (e.g. fatty acids, complex carbohydrates etc).

In another embodiment, peptides may comprise fragments of native polypeptides from any animal species (including humans), derivatives of native (human and non-human) polypeptides and their fragments, and variants of native polypeptides. In one embodiment, "fragments" comprise regions within the sequence of a mature native polypeptide, and in another embodiment, "derivatives" comprise amino acid sequence and glycosylation variants, and covalent modifications of a native polypeptide. In another embodiment, "variants" refers to amino acid sequence and glycosylation variants of the native polypeptide.

In another embodiment, the water-soluble compound is a nucleic acid.

In one embodiment, the term "nucleic acid" molecule refers to DNA or RNA which may be single or double stranded. The nucleic acid may comprise a sequence that is prokaryotic or eukaryotic mRNA in nature. The DNA may comprise cDNA from eukaryotic or prokaryotic mRNA, genomic DNA sequences from eukaryotic or prokaryotic DNA, or, in another embodiment, synthetic DNA sequences. The term also refers to sequences that include any of the known base analogs of DNA and RNA.

The nucleic acid sequences within the controlled release composite of this invention may be naked nucleic acid, or, in another embodiment, may be contained within a vector.

According to this aspect of the invention, and in one embodiment, polynucleotide segments encoding sequences of interest can be ligated into commercially available expression vector systems suitable for transducing/transforming mammalian cells and for directing the expression of recombinant products within the transduced cells. It will be appreciated that such commercially available vector systems can easily be modified via commonly used recombinant techniques in order to replace, duplicate or mutate existing promoter or enhancer sequences and/or introduce any additional polynucleotide sequences such as for example, sequences encoding additional selection markers or sequences encoding reporter polypeptides (for further detail see, for example, "Methods in Enzymology" Vol. 1–317, Academic Press, Current Protocols in Molecular Biology, Ausubel F. M. et al. (eds.) Greene Publishing Associates, (1989) and in Molecular Cloning: A Laboratory Manual, 2nd Edition, Sambrook et al. Cold Spring Harbor Laboratory Press, (1989), or other standard laboratory manuals).

Uptake of the nucleic acid released via composite microparticles or scaffolding of this invention within a cell can be assessed by standard approaches routinely used in the art. For example, filter hybridization techniques (e.g., Northern or Southern blotting) may be performed on cells or tissue contacted with the composite microparticles or scaffolding of this invention, or, in another embodiment, RNase protection or reverse transcriptase-polymerase chain reaction (RT-PCR) may be performed, to detect uptake of the plasmids or DNA, and measure expression thereof. The gene product can be detected by an appropriate assay, for example by immunological detection of a produced protein, such as with a specific antibody, or by a functional assay to detect a functional activity of the gene product, such as an enzymatic assay. If the gene product of interest to be expressed by a cell is not readily assayable, an expression system can first be optimized using a reporter gene linked to the regulatory elements and vector to be used. The reporter gene encodes a gene product, which is easily detectable and, thus, can be used to evaluate efficacy of the system. Standard reporter genes used in the art include genes encoding β-galactosidase, chloramphenicol acetyl transferase, luciferase and human growth hormone, or any of the marker proteins listed herein. Similarly, composite microparticles and scaffolding release of proteins may be similarly assessed.

In another embodiment, the water-soluble compound is a drug. In one embodiment, the term "drug" refers to a molecule that alleviates a symptom, disease or disorder when administered to a subject afflicted thereof. In one embodiment, a drug is a synthetic molecule, or in another embodiment, a drug is a naturally occurring compound isolated from a source found in nature.

In one embodiment, drugs may comprise antihypertensives, antidepressants, antianxiety agents, anticlotting agents, anticonvulsants, blood glucose-lowering agents, decongestants, antihistamines, antitussives, anti-inflammatories, antipsychotic agents, cognitive enhancers, cholesterol-reducing agents, antiobesity agents, autoimmune disorder agents, anti-impotence agents, antibacterial and antifungal agents, hypnotic agents, anti-Parkinsonism in agents, antibiotics, antiviral agents, anti-neoplastics, barbituates, sedatives, nutritional agents, beta blockers, emetics, anti-emetics, diuretics, anticoagulants, cardiotonics, androgens, corticoids, anabolic agents, growth hormone secretagogues, anti-infective agents, coronary vasodilators, carbonic anhydrase inhibitors, antiprotozoals, gastrointestinal agents, serotonin antagonists, anesthetics, hypoglycemic agents, dopaminergic agents, anti-Alzheimer's Disease agents, anti-ulcer agents, platelet inhibitors and glycogen phosphorylase inhibitors.

According to this aspect of the invention, and in one embodiment, examples of the drugs released according to this invention are antihypertensives including prazosin, nifedipine, trimazosin, amlodipine, and doxazosin mesylate; the antianxiety agent hydroxyzine; a blood glucose lowering agent such as glipizide; an anti-impotence agent such as sildenafil citrate; anti-neoplastics such as chlorambucil, lomustine or echinomycin; anti-inflammatory agents such as betamethasone, prednisolone, piroxicam, aspirin, flurbiprofen and (+)-N-{4-[3-(4-fluorophenoxy)phenoxy]-2-cyclopenten-1-yl}-N-hyroxyurea; antivirals such as acyclovir, nelfinavir, or virazole; vitamins/nutritional agents such as retinol and vitamin E; emetics such as apomorphine; diuretics such as chlorthalidone and spironolactone; an anticoagulant such as dicumarol; cardiotonics such as digoxin and digitoxin; androgens such as 17-methyltestosterone and testosterone; a mineral corticoid such as desoxycorticosterone; a steroidal hypnotic/anesthetic such as alfaxalone; an anabolic agent such as fluoxymesterone or methanstenolone; antidepression agents such as fluoxetine, pyroxidine, venlafaxine, sertraline, paroxetine, sulpiride, [3,6-dimethyl-2-(2,4,6-trimethyl-phenoxy)-pyridin-4-yl]-(lethylpropyl)-amine or 3,5-dimethyl-4-(3'-pentoxy)-2-(2',4',6'-trimethylphenoxy)pyridine; an antibiotic such as ampicillin and penicillin G; an anti-infective such as benzalkonium chloride or chlorhexidine; a coronary vasodilator such as nitroglycerin or mioflazine; a hypnotic such as etomidate; a carbonic anhydrase inhibitor such as acetazolamide or chlorzolamide; an antifungal such as econazole, terconazole, fluconazole, voriconazole or griseofulvin; an antiprotozoal such as metronidazole; an imidazole-type anti-neoplastic such as tubulazole; an anthelmintic agent such as thiabendazole or oxfendazole; an antihistamine such as astemizole, levocabastine, cetirizine, or cinnarizine; a decongestant such as pseudoephedrine; antipsychotics such as fluspirilene, penfluridole, risperidone or ziprasidone; a gastrointestinal agent such as loperamide or cisapride; a serotonin antagonist such as ketanserin or mianserin; an anesthetic such as lidocaine; a hypoglycemic agent such as acetohexamide; an anti-emetic such as dimenhydrinate; an antibacterial such as cotrimoxazole; a dopaminergic agent such as L-DOPA; anti-Alzheimer agents such as THA or donepezil; an anti-ulcer agent/H2 antagonist such as famotidine; a sedative/hypnotic such as chlordiazepoxide or triazolam; a vasodilator such as alprostadil; a platelet inhibitor such as prostacyclin; an ACE inhibitor/antihypertensive such as enalaprilic acid or lisinopril; a tetracycline antibiotic such as oxytetracycline or minocycline; a macrolide antibiotic such as azithromycin, clarithromycin, erythromycin or spiramycin; and glycogen phosphorylase inhibitors such as [R—(R*S*)]-5-chloro-N-[2-hydroxy-3{methoxymethylamino}-3-oxo-1-(phenylmethyl)-propyl]-IH-indole-2-carboxamide or 5-chloro-1-Hindole-2-carboxylic acid [(IS)-benzyl(2R)-hydroxy-3-((3R,4S)dihydroxy-pyrrolidin-1-yl-)-oxypropyl] amide.

Further examples of drugs deliverable by the invention are the glucose-lowering drug chlorpropamide, the anti-fungal fluconazole, the anti-hypercholesterolemic atorvastatin calcium, the antipsychotic thiothixene hydrochloride, the anxiolytics hydroxyzine hydrochloride or doxepin hydrochloride, the anti-hypertensive amlodipine besylate, the anti-inflammatories piroxicam and celicoxib and valdicoxib, and the antibiotics carbenicillin indanyl sodium, bacampicillin hydrochloride, troleandomycin, and doxycycline hyclate.

In another embodiment a drug of this invention may comprise other antineoplastic agents such as platinum compounds (e.g., spiroplatin, cisplatin, and carboplatin), methotrexate, fluorouracil, adriamycin, mitomycin, ansamitocin, bleomycin, cytosine arabinoside, arabinosyl adenine, mercaptopolylysine, vincristine, busulfan, chlorambucil, melphalan (e.g., PAM, L-PAM or phenylalanine mustard), mercaptopurine, mitotane, procarbazine hydrochloride dactinomycin (actinomycin D), daunorubicin hydrochloride, doxorubicin hydrochloride, paclitaxel and other taxenes, rapamycin, manumycin A, TNP-470, plicamycin (mithramycin), aminoglutethimide, estramustine phosphate sodium, flutamide, leuprolide acetate, megestrol acetate, tamoxifen citrate, testolactone, trilostane, amsacrine (m-AMSA), asparaginase (L-asparaginase) Erwina asparaginase, interferon .alpha.-2a, interferon .alpha.-2b, teniposide (VM-26), vinblastine sulfate (VLB), vincristine sulfate, bleomycin sulfate, hydroxyurea, procarbazine, and dacarbazine; mitotic inhibitors such as etoposide, colchicine, and the vinca alkaloids, radiopharmaceuticals such as radioactive iodine and phosphorus products; hormones such as progestins, estrogens and antiestrogens; anti-helmintics, antimalarials, and antituberculosis drugs; biologicals such as immune serums, antitoxins and antivenoms; rabies prophylaxis products; bacterial vaccines; viral vaccines; respiratory products such as xanthine derivatives theophylline. and aminophylline; thyroid agents such as iodine products and anti-thyroid agents; cardiovascular products including chelating agents and mercurial diuretics and cardiac glycosides; glucagon; blood products such as parenteral iron, hemin, hematoporphyrins and their derivatives; biological response modifiers such as muramyldipeptide, muramyltripeptide, microbial cell wall components, lymphokines (e.g., bacterial endotoxin such as lipopolysaccharide, macrophage activation factor), sub-units of bacteria (such as Mycobacteria, Corynebacteria), the synthetic dipeptide N-acetyl-muramyl-L-alanyl-D-isoglutamine; anti-fungal agents such as ketoconazole, nystatin, griseofulvin, flucytosine (5-fc), miconazole, amphotericin B, ricin, cyclosporins, and β-lactam antibiotics (e.g., sulfazecin); hormones such as growth hormone, melanocyte stimulating hormone, estradiol, beclomethasone dipropionate, betamethasone, betamethasone acetate and betamethasone sodium phosphate, vetamethasone disodium phosphate, vetamethasone sodium phosphate, cortisone acetate, dexamethasone, dexamethasone acetate, dexamethasone sodium phosphate, flunisolide, hydrocortisone, hydrocortisone acetate, hydrocortisone cypionate, hydrocortisone sodium phosphate, hydrocortisone sodium succinate, methylprednisolone, methylprednisolone acetate, methylprednisolone sodium succinate, paramethasone acetate, prednisolone, prednisolone acetate, prednisolone sodium phosphate, prednisolone tebutate, prednisone, triamcinolone, triamcinolone acetonide, triamcinolone diacetate, triamcinolone hexacetonide, fludrocortisone acetate, oxytocin, vassopressin, and their derivatives; vitamins such as cyanocobalamin neinoic acid, retinoids and derivatives such as retinol palmitate, and .alpha.-tocopherol; peptides, such as manganese super oxide dismutase; enzymes such as alkaline phosphatase; anti-allergic agents such as amelexanox; anti-coagulation agents such as phenprocoumon and heparin; circulatory drugs such as propranolol; metabolic potentiators such as glutathione; antituberculars such as para-aminosalicylic acid, isoniazid, capreomycin sulfate cycloserine, ethambutol hydrochloride ethionamide, pyrazinamide, rifampin, and streptomycin sulfate; antivirals such as amantadine azidothymidine (AZT, DDI, Foscarnet, or Zidovudine), ribavirin and vidarabine monohydrate (adenine arabinoside, ara-A); antianginals such as diltiazem, nifedipine, verapamil, erythritol tetranitrate, isosorbide dinitrate, nitroglycerin (glyceryl trinitrate) and pentaerythritol tetranitrate; anticoagulants such as phenprocoumon, heparin; antibiotics such as dapsone, chloramphenicol, neomycin, cefaclor, cefadroxil, cephalexin, cephradine erythromycin, clindamycin, lincomycin, amoxicillin, ampicillin, bacampicillin, carbenicillin, dicloxacillin, cyclacillin, picloxacillin, hetacillin, methicillin, nafcillin, oxacillin, penicillin including penicillin G and penicillin V, ticarcillin rifampin and tetracycline; antiinflammatories such as diflunisal, ibuprofen, indomethacin, meclofenamate, mefenamic acid, naproxen, oxyphenbutazone, phenylbutazone, piroxicam, sulindac, tolmetin, aspirin and salicylates; antiprotozoans such as chloroquine, hydroxychloroquine, metronidazole, quinine and meglumine antimonate; antirheumatics such as penicillamine; narcotics such as paregoric; opiates such as codeine, heroin, methadone, morphine and opium; cardiac glycosides such as deslanoside, digitoxin, digoxin, digitalin and digitalis; neuromuscular blockers such as atracurium mesylate, gallamine triethiodide, hexafluorenium bromide, metocurine iodide, pancuronium bromide, succinyicholine chloride (suxamethonium chloride), tubocurarine chloride and vecuronium bromide; sedatives (hypnotics) such as amobarbital, amobarbital sodium, aprobarbital, butabarbital sodium, choral hydrate, ethchlorvynol, ethinamate, flurazepam hydrochloride, glutethimide, methotrimeprazine hydrochloride, methyprylon, midazolam hydrochloride, paraldehyde, pentobarbital, pentobarbital sodium, phenobarbital sodium, secobarbital sodium, talbutal, temazepam and triazolam; local anesthetics such as bupivacaine hydrochloride, chloroprocaine hydrochloride, etidocaine hydrochloride, lidocaine hydrochloride, mepivacaine hydrochloride, procaine hydrochloride and tetracaine hydrochloride; general anesthetics such as droperidol, etomidate, fentanyl citrate with droperidol, ketamine hydrochloride, methohexital sodium and thiopental sodium; and radioactive particles or ions such as strontium, iodide rhenium and yttrium.

In another embodiment of this invention, the water-soluble compound may comprise an imaging or diagnostic agent, for example, and in other embodiments, radio-opaque agents, labeled antibodies, labeled nucleic acid probes, dyes, such as colored or fluorescent dyes, etc; adjuvants, radiosensitizers, or inhibitors of multidrug resistance and/or efflux pumps, etc.

In another embodiment, the peptide, protein or drug promotes tissue formation. In one embodiment, the peptide, protein or drug is osteogenic, chondrogenic or angiogenic.

Preparation of the controlled release composite of this invention may be accomplished via any number of means well known to one skilled in the art.

In one embodiment, composite controlled release particles comprising a water-soluble compound, may be prepared by a process comprising the steps of adsorbing a water-soluble compound onto a basic, inorganic material, combining the product in (a) with a solution of a biodegradable polymer which yields acidic degradation products to form composite microparticles suspended as a solid-in oil emulsion, homogenizing the product in (b) in an aqueous solution and isolating said composite particles.

In another embodiment, the composite controlled release particles comprising a water-soluble compound, may be prepared by a microprecipitation process, as described and exemplified hereinbelow.

In one embodiment, the composite materials of this invention may be prepared as described, or as exemplified hereinbelow in Examples 1, 7, 8, 9, 10 or 11.

The water-soluble compound of this invention is adsorbed onto a basic inorganic material, in one embodiment, via the addition of a solution of the water-soluble compound to an aqueous suspension of the basic inorganic material. In one embodiment, the suspension is then stirred for a period of time in order to enable adsorption to take place. In one embodiment, stirring may take place over the course of 1 to 24 hours. In another embodiment, stirring may take place over the course of 1 to 10 hours, or in another embodiment, over the course of 10 to 15 hours, or in another embodiment, over the course of 15 to 20 hours, or in another embodiment, over the course of 10 to 24 hours.

In one embodiment, the basic inorganic material will have a surface area of at least 10 $m^2/g$, which allows for a greater number of sites for protein adsorption. In one embodiment, the basic inorganic material will have a surface area of at least 15 $m^2/g$, or in another embodiment, at least 20 $m^2/g$, or in another embodiment, at least 25 $m^2/g$, or in another embodiment, at least 30 $m^2/g$, or in another embodiment, at least 35 $m^2/g$, or in another embodiment, at least 40 $m^2/g$, or in another embodiment, at least 50 $m^2/g$.

In one embodiment, adsorption of the water-soluble compound onto the basic inorganic material is conducted in an aqueous medium, with the water-soluble compound present at a concentration of between 100 ng/ml-10 mg/ml, or, in another embodiment, 250 ng/ml to 1 mg/ml, or, in another embodiment, 500 ng/ml to 1 mg/ml, or, in another embodiment, 1 μg/ml to 10 mg/ml, or, in another embodiment, 10 μg/ml to 5 mg/ml, or, in another embodiment, 50 μg/ml to 5 mg/ml, or, in another embodiment, 75 μg/ml to 10 mg/ml, or, in another embodiment, 0.1 to 1 mg/ml, or, in another embodiment, 0.1 to 5 mg/ml, or, in another embodiment, 1 to 5 mg/ml, or, in another embodiment, 1 to 10 mg/ml, or, in another embodiment, 5 to 10 mg/ml. In one embodiment, the water-soluble compound concentration in the aqueous medium may be relatively dilute.

In another embodiment, the ratio of water-soluble compound to inorganic basic material may range from 1:10,000–1:1 by mass. In one embodiment, the ratio of water-soluble compound to inorganic basic material is 1:10,000, or in another embodiment, 1:5,000, or in another embodiment, 1:1,000, or in another embodiment, 1:100, or in another embodiment, 1:10, or in another embodiment, 1:5, or in another embodiment, 1:1. In one embodiment, the amount of water-soluble compound will not exceed the amount of inorganic basic material. In one embodiment, the amount of water-soluble compound may be at a concentration several-fold less than that of the inorganic basic material.

In another embodiment, the inorganic material with adsorbed compound will have a diameter of between 10 nm to 50 microns. In another embodiment, the inorganic material with adsorbed compound will have a diameter of between 10 nm to 50 nm, or in another embodiment, of between 50 nm to 100 nm, or in another embodiment, of between 50 nm to 150 nm, or in another embodiment, of between 100 nm to 250 nm, or in another embodiment, of between 50 nm to 100 nm, or in another embodiment, of between 250 nm to 500 nm, or in another embodiment, of between 500 nm to 750 nm, or in another embodiment, of between 500 nm to 1 micron, or in another embodiment, of between 1 micron to 10 microns, or in another embodiment, of between 10 microns to 25 microns, or in another embodiment, of between 25 microns to 50 microns.

In another embodiment, the inorganic material with adsorbed compound is added to a bio-degradable polymer solution at a ratio of inorganic material to polymer concentration of 0.001 to 0.75. In another embodiment, the ratio of inorganic material to polymer concentration is 0.001 to 0.10, or, in another embodiment, the ratio of inorganic material to polymer concentration is 0.001 to 0.01, or, in another embodiment, the ratio of inorganic material to polymer concentration is 0.001 to 0.01, or, in another embodiment, the ratio of inorganic material to polymer concentration is 0.01 to 0.1, or, in another embodiment, the ratio of inorganic material to polymer concentration is 0.01 to 0.25, or, in another embodiment, the ratio of inorganic material to polymer concentration is 0.01 to 0.50, or, in another embodiment, the ratio of inorganic material to polymer concentration is 0.01 to 0.5, or, in another embodiment, the ratio of inorganic material to polymer concentration is 0.01 to 0.75, or, in another embodiment, the ratio of inorganic material to polymer concentration is 0.1 to 0.25, or, in another embodiment, the ratio of inorganic material to polymer concentration is 0.1 to 0.50, or, in another embodiment, the ratio of inorganic material to polymer concentration is 0.1 to 0.75. In another embodiment, the ratio of inorganic material to polymer may range from 0.001:1 to 1:1 by mass. In one embodiment, the ratio of inorganic material to polymer is 0.08:1, or in another embodiment, the ratio of inorganic material to polymer is 0.16:1, or, in another embodiment, the ratio of inorganic material to polymer is 0.2:1.

In one embodiment, the basic, inorganic material adsorbed water-soluble compound is then collected by centrifugation, or in another embodiment, ultrafiltration, and in another embodiment, may be washed, and, in another embodiment, lyophilized. In one embodiment, dry, lyophilization produces a free-flowing powder for subsequent easy dispersion in a biodegradable polymer solution.

The amount of water-soluble compound adsorbed onto the basic inorganic material may be determined, in another embodiment. Such a determination may be effected, in one embodiment, via measuring the concentration of the original water-soluble compound, and making such a determination on the supernatant recovered following adsorption, with the difference representing the amount of compound adsorbed. In one embodiment, the water-soluble compound may be modified to comprise an indicator compound, which can facilitate a determination of the amount of compound adsorbed.

In one embodiment, the basic inorganic material adsorbed water-soluble compound may then be combined with a solution of the biodegradable polymer, forming a solid-in-oil suspension. In one embodiment, vortexing, or in another embodiment, sonication of the combined products provides a uniform suspension. In one embodiment, the polymer solution is prepared in water immiscible organic solvents such as dichloromethane (DCM), chloroform, dichloroethane, trichloroethane, cyclohexane, benzene, toluene, ethyl acetate, acetone, and the like, which can be used alone or, in another embodiment, as a mixture thereof.

The solid-in-oil suspension thus obtained, in the composite controlled release systems of this invention, is then homogenized in an aqueous solution. The suspension may be heated, in one embodiment, wherein heating may, in another embodiment, serve to drive off the organic solvent and solidify the microparticles. The particles may, in another embodiment, be collected by centrifugation, washed and lyophilized.

In another embodiment, the time, speed, or combination thereof of the homogenization step may be varied. In one embodiment, the homogenization time may be in a range of between 1 to 10 minutes. In one embodiment, homogenization is carried out for 2 minutes, or, in another embodiment, homogenization is carried out for 3 minutes, or, in another embodiment, homogenization is carried out for 4 minutes, or, in another embodiment, homogenization is carried out for 5 minutes, or, in another embodiment, homogenization is carried out for 7 minutes, or, in another embodiment, homogenization is carried out for 10 minutes.

In another embodiment, homogenization speed may vary from between 1,000 to 20,000 rpm. In one embodiment, homogenization speed is 5,000 rpm, or in another embodiment, homogenization speed is 8,000 rpm, or in another embodiment, homogenization speed is 12,000 rpm, or in another embodiment, homogenization speed is 16,000 rpm, or in another embodiment, homogenization speed is 20,000 rpm.

In another embodiment, both the time and speed of homogenization is varied, so that composite particles comprising a given water-insoluble compound differing in size are produced.

In another embodiment the aqueous solution may comprise a surfactant or other detergent. In another embodiment, the polymer solution concentration, the molecular weight of said polymer, or a combination thereof, may be varied. In another embodiment, varying the polymer solution concentration, molecular weight of the polymer, or a combination thereof, affects the release rate of the water-soluble product. In one embodiment, varying the polymer solution concentration, molecular weight of the polymer, or a combination thereof when preparing composite particles of this invention produces composite particles differing in size.

Figure 7:
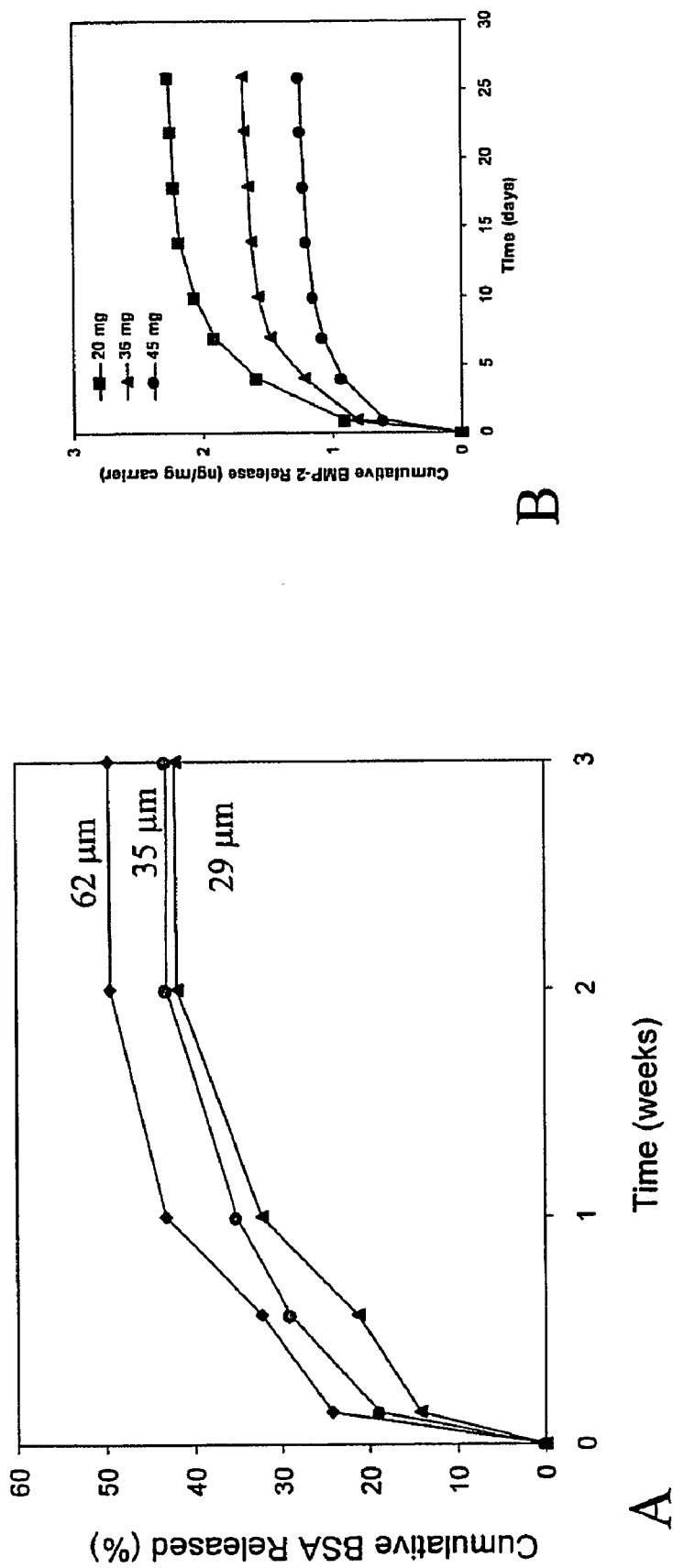
FIG. 7 demonstrates protein release from composite microparticles. Effects on release profiles, with microparticles, which differ with respect to size. Processing parameters were adjusted to obtain particles of different size with comparable apatite and BSA loading (A). Protein release was conducted at 37° C. (B) Effect of apatite loading (per 250 mg of polymer) on rhBMP-2 release. Composite particles were fabricated from 59 kD PLGA and contained 65 ng of rhBMP-2 per mg of carrier.
Figure 8:
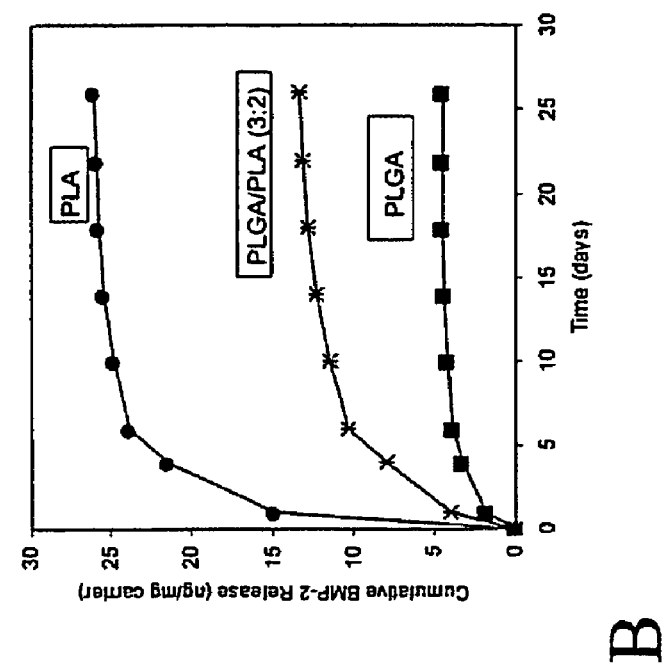
FIG. 8 demonstrates the effect of polymer hydrophobicity on protein release. Particles contained 15 mg of FITC-BSA per mg carrier. The molecular weight of PLGA was 24 kD and that of PLA was 25 kD (A). (B) Effect of polymer hydrophobicity on rhBMP-2 release. Composite particles contained 145 ng of rhBMP-2 per mg of carrier. Molecular weights of PLGA and PLA were 59 kD and 25 kD, respectively.
Figure 8:
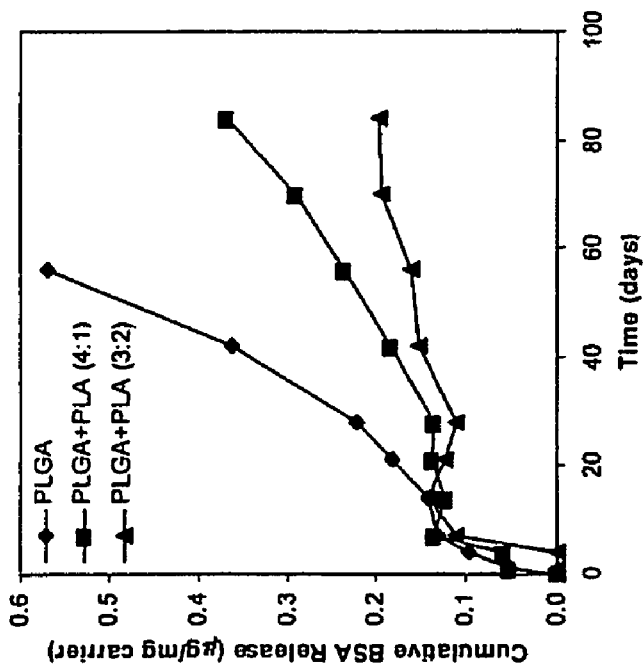

In another embodiment, the polymer may comprise a blend of at least 2 polymers, which differ in their hydrophobicity. In another embodiment, a hydrophilic polymer may be blended with a hydrophobic polymer. In another embodiment, the blended polymers may be varied in terms of their concentration. In another embodiment, varying the concentration of the polymers affects the release rate of the water-soluble compound, or composite particle size in composite particle embodiments of this invention, or the polymer degradation rate, or a combination thereof, as was exemplified herein in FIGS. 7 and 8.

In another embodiment, the particle size of the basic inorganic material may be varied to produce composite particles differing in size, or in another embodiment, to alter release kinetics of the water-soluble compound. As exemplified in FIG. 10 herein, smaller particle size of the CAP resulted in greater, sustained release of the adsorbed BSA and BMP.

In another embodiment, free apatite may be added with the adsorbed water-soluble compound to the solution of a biodegradable polymer when forming the composite particles, or composite controlled release systems of this invention. In another embodiment, any free basic inorganic molecule of this invention may be added to the solution of a biodegradable polymer when forming the composite particles or composite controlled release systems of this invention. According to this aspect of the invention, and in one embodiment, such basic inorganic molecules may be added to regulate the amount of water-soluble compound released.

In another embodiment, the composite may further comprise an amphoteric species. In one embodiment, the *amphoteric* species alters the rate of dissolution of the basic inorganic material, or in another embodiment, the liberation of the adsorbed compound, or in another embodiment, both. In another embodiment, the amphoteric species serves as a diffusion barrier to the liberated compound.

In another embodiment, the composite may comprise a species, which imparts enhanced viscosity to the composite upon administration in vivo. In one embodiment, the species is a glycosaminoglycan, or an extracellular matrix component. In one embodiment, the species serves as a diffusion barrier to the liberated compound of the composite, and thereby participates in the controlled release of the compound.

In one embodiment, the composite may be produced via the addition of composite particles prepared by any means, as will be appreciated by one skilled in the art, wherein the particles comprise the water-soluble molecule-loaded basic inorganic material in complex with a polymer which produces acidic degradation products, and the particles may then be added to a solution of gelatin. In one embodiment, the term "in complex" refers to the water-soluble molecule-loaded basic inorganic material being embedded within or, in another embodiment, mixed with the polymer.

Particle loading may be varied, in one embodiment. For example, protein-loaded apatite-PLGA composite particles may be added to a 10 w/v % solution of gelatin, and various amounts of the particles may be added to achieve particle loading with varied concentration. In another embodiment, the mixture may then be crosslinked with an appropriate crosslinking agent, such as, for example, glutaraldehyde or formaldehyde, or formalin, or any other appropriate agent as will be known to one skilled in the art. In one embodiment, such formulations may assume the form of gels, and may represent an embodiment of composite gels of this invention.

In one embodiment, the amphoteric species is a gelatin, or in another embodiment, a collagen, a fibrinogen (fibrin), a hyaluronic acid or a chitosan. In one embodiment, gelatin refers to a material whether extracted by traditional methods or recombinant or biosynthetic in origin, or to any molecule having at least one structural and/or functional characteristic of gelatin. Gelatin may, in one embodiment, be obtained by extraction from collagen derived from animal (e.g., bovine, porcine, rodent, chicken, equine, piscine, etc.) sources, for example, bones and tissues. The term gelatin encompasses, in other embodiments, both the composition of more than one polypeptide included in a gelatin product, as well as an individual polypeptide contributing to the gelatin material.

Polypeptides from which gelatin can be derived, in other embodiments, are polypeptides such as collagens, procollagens, and other polypeptides having at least one structural and/or functional characteristic of collagen. Such a polypeptide could include a single collagen chain, or a collagen homotrimer or heterotrimer, or any fragments, derivatives, oligomers, polymers, or subunits thereof, containing at least one collagenous domain (a Gly-X-Y region). Engineered collagens, derived from transcribing/translating sequences not found in nature, such as altered collagen constructs, etc., for example, polynucleotides comprising a sequence that is altered, through deletions, additions, substitutions, or other changes, from the naturally occurring collagen gene, are also to be considered as part of this invention.

Figure 12:
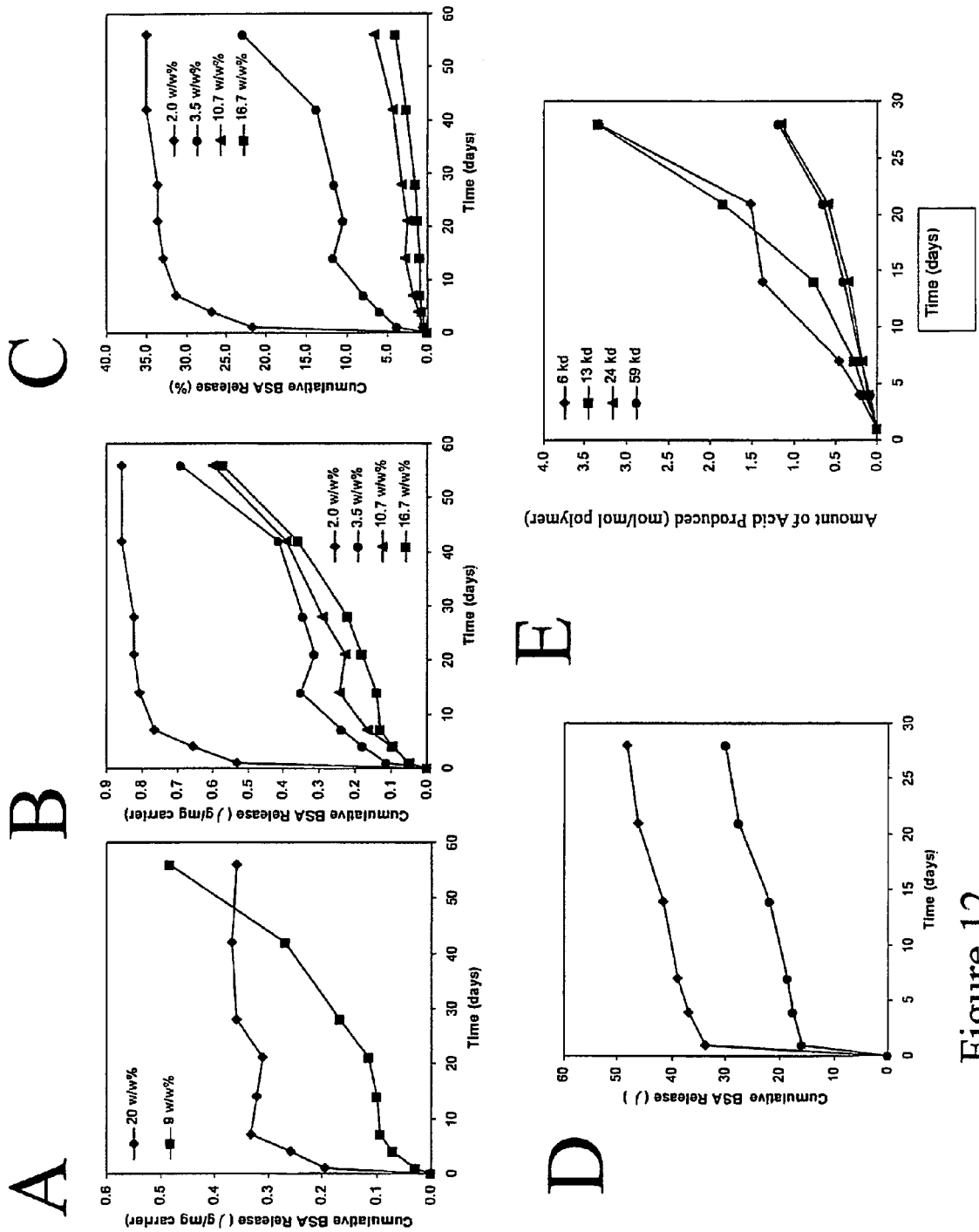
FIG. 12 demonstrates the effect of apatite-protein complex loading on protein release, expressed as cumulative mass of BSA released per mg carrier and percentage cumulative release of BSA.

In another embodiment, the percent water-soluble compound adsorbed onto said basic, inorganic material is varied. In one embodiment, the percent water-soluble compound loaded in the composite microparticle ranges from 1 to 40 wt % (We have attained a loading of 31 wt %, and I believe we can reach 40 wt % with some new materials we are testing), or in another embodiment, from 1 to 5 wt %, or in another embodiment, from 5 to 10 wt %, or in another embodiment, from 10 to 15 wt %, or in another embodiment, from 10 to 20 wt %, or in another embodiment, from 15 to 20 wt %, or in another embodiment, from 10 to 30 wt %, or in another embodiment, from 15 to 40 wt %, or in another embodiment, from 25 to 40 wt %. In another embodiment, the percent water-soluble compound loaded in the composite microparticle is 2, or 3.5, or 11, or 17 wt %, and is exemplified herein in FIG. 12, which represents another embodiment of this invention.

In another embodiment, varying the percent water-soluble compound adsorbed onto the basic, inorganic material, or loaded in the composite microparticle affects the release kinetics of the water-soluble compound from the composite microparticles.

In another embodiment, this invention provides a particle produced by a process of this invention, or any embodiment thereof. It is to be understood that processes exemplified herein, such as those described in Example 1 and 8, or modifications thereof that yield a composite controlled release particle, are to be considered as part of this invention and embodiments thereof.

In another embodiment, this invention provides a composite material comprising a water-soluble compound adsorbed onto a basic, inorganic material and a bio-degradable polymer which yields acidic degradation products. In one embodiment, the water-soluble compound is a peptide, a protein, a nucleic acid or a drug. In another embodiment, the peptide or protein is osteogenic, chondrogenic or angiogenic. In another embodiment, the basic inorganic material is hydroxyapatite or carbonated apatite. In another embodiment, the biodegradable polymer is polylactide-co-glycolide. In another embodiment, the polymer comprises a blend of at least 2 polymers, which differ in their hydrophobicity. In another embodiment, the polymers may differ in terms of their concentration. In another embodiment, the basic inorganic material may be in the form of a particle with a diameter ranging in size from 1 to 200 µm. Composite controlled release particles of this invention may range from the nanometer to micrometer scale, or may be larger, in another embodiment.

It is to be understood that a particle comprising any embodiment described herein for a water-soluble compound, or a basic, inorganic material, or a bio-degradable polymer, or combination thereof, is to be considered as part of this invention, as additional embodiments thereof.

In another embodiment, this invention provides a process for preparing a composite scaffolding comprising a water-soluble compound, comprising the steps of (a) adsorbing a water-soluble compound onto a basic, inorganic material, (b) combining the product in (a) with a solution of a biodegradable polymer which yields acidic degradation products to form a solid-in oil emulsion, (c) precipitating the composite scaffolding product in (b), and (d) isolating the composite scaffolding.

In one embodiment, combining the product in (a) with a solution of a biodegradable polymer may be accomplished via sonication.

In one embodiment, precipitation according to this aspect of the invention may be effected via the addition of an alcohol. In one embodiment, the alcohol is ethanol. Precipitation may be conducted via any means well known to one in the art. In another embodiment the composite scaffolding is dried following precipitation, by any means well known to one skilled in the art.

In another embodiment, this invention provides a process for preparing a composite scaffolding comprising a water-soluble compound, comprising the steps of (a) preparing composite microparticles according to a process of this invention, (b) combining the composite microparticles of (a) with a solution of gelatin, chitosan, arabinogalactan, collagen, alginate, hyaluronic acid, fibrin, cellulose, or a synthetic polymers such as, in other embodiments, PEG-PLGA or PVA-PLGA, polylactic or polyglycolic acid; (c) adding a cross-linker to the product of (b) forming a composite scaffolding, (d) lyophilizing the composite scaffolding, and (f) isolating the composite scaffolding.

According to this aspect of the invention, and in one embodiment, the gelatin, chitosan, arabinogalactan, collagen, alginate, hyaluronic acid, fibrin, cellulose or a synthetic polymers such as, in other embodiments, PEG-PLGA or PVA-PLGA, polylactic or polyglycolic acid used may be of varied molecular weights, and derived from any number of sources. In one embodiment, high molecular weight gelatin, chitosan, arabinogalactan, collagen, alginate, hyaluronic acid, fibrin, cellulose or a synthetic polymers such as, in other embodiments, PEG-PLGA or PVA-PLGA, polylactic or polyglycolic acid is utilized, and in another embodiment, such use results in slower in-vivo degradation.

In one embodiment, cross-linking is accomplished with glutaraldehyde and is conducted, in one embodiment, at room temperature, or in another embodiment, at 4° C. In another embodiment, other cross-linking agents such as formaldehyde, or in another embodiment, paraformaldehyde, or in another embodiment, formalin, or in another embodiment, acetone is utilized, or in another embodiment, carbodiimide. In another embodiment, capping of unreacted cross-linking agent is conducted, which reduces cytotoxicity, in another embodiment. In one embodiment, capping is conducted with glycine, and the scaffolding is washed following the capping. In another embodiment, the scaffolding is frozen. In one embodiment, the freezing rate influences the pore size of the scaffold. In another embodiment, the scaffold is lyophilized following freezing. In another embodiment, the compressive modulus of gelatin, for example, is enhanced by the composite microparticles comprising the scaffold.

In another embodiment, this invention provides a porous scaffolding, comprising a composite material of this invention, and in another embodiment, prepared by a process of this invention, or any embodiment thereof.

It is to be understood that the composite controlled releasing of this invention may comprise composite controlled release particles, which may comprise any embodiment listed herein, or combinations thereof.

In another embodiment, this invention provides a composite scaffolding, comprising a water-soluble compound adsorbed onto a basic, inorganic material and a biodegradable polymer which yields acidic degradation products. In one embodiment, the composite material may be in the form of a film or gel, as described, and as exemplified herein. In one embodiment, the water-soluble compound is a peptide, a protein, a nucleic acid or a drug, or any other embodiment listed herein. In another embodiment, the peptide or protein or drug is osteogenic, chondrogenic or angiogenic. In another embodiment, the basic inorganic material is hydroxyapatite or carbonated apatite, or any other embodiment listed herein. In another embodiment, the biodegradable polymer is polylactide-co-glycolide or other embodiments listed herein. In another embodiment, the polymer may comprises a blend of at least 2 polymers, as described herein, and comprise any and all embodiment thereof. In another embodiment, the basic inorganic material may be in the form of a particle with a diameter ranging in size from 1 to 200 µm. In one embodiment, the composite scaffolds of this invention may provide sustained release of a water-soluble compound comprising the scaffolding, wherein release may be sustained for a period of, in one embodiment, hours, to, in another embodiment, days, or in another embodiment, weeks. In one embodiment, release of the water-soluble compound may be detected for 4 weeks or more, as exemplified herein in FIG. 14.

In another embodiment, this invention provides a method of controlled release of a therapeutic compound to a subject, comprising administering to the subject a composite controlled release system comprising a therapeutic water-soluble compound adsorbed onto a basic, inorganic material and a bio-degradable polymer which yields acidic degradation products, whereby degradation of said polymer yields acidic degradation products therefrom, which stimulates dissolution of the inorganic material and release of said therapeutic compound over a period of time, thereby being a method of controlled release of a therapeutic compound.

In another embodiment, this invention provides a method of controlled release of a therapeutic compound, comprising contacting a cell in a subject with a composite microparticle comprising a water-soluble therapeutic compound adsorbed onto a basic, inorganic material and a bio-degradable polymer which yields acidic degradation products, whereby degradation of said polymer yields acidic degradation products therefrom, which stimulates dissolution of the inorganic material and release of said therapeutic compound over a period of time, thereby being a method of controlled release of a therapeutic compound.

In one embodiment, the therapeutic compound is a peptide, a protein, a nucleic acid or a drug. In another embodiment, the therapeutic compound is osteogenic, chondrogenic or angiogenic. In another embodiment, the therapeutic compound is an antibacterial, antiviral, antifungal or antiparasitic compound. In another embodiment, the therapeutic compound has cytotoxic or anti-cancer activity. In another embodiment, the therapeutic compound is an enzyme, a receptor, a channel protein, a hormone, a cytokine or a growth factor. In another embodiment, the therapeutic compound is immunostimulatory. In another embodiment, the therapeutic compound inhibits inflammatory or immune responses.

In another embodiment, dissolution of the basic inorganic material releases charged species over a course of time. In one embodiment, the charged species are therapeutic, and in another embodiment, comprise calcium or phosphate, or a combination thereof. In another embodiment, the charged species are osteogenic, or in another embodiment, the charged species promote tissue repair.

It is to be understood that the water-soluble therapeutic compound utilized for the methods of this invention may comprise any embodiment listed herein referring to the same, or a combination thereof. In one embodiment, the therapeutic compound is osteogenic, chondrogenic or angiogenic. In another embodiment, the therapeutic compound is an antibacterial, antiviral, antifungal or antiparasitic compound. In another embodiment, the therapeutic compound has cytotoxic or anti-cancer activity. In another embodiment, the therapeutic compound is an enzyme, a receptor, a channel protein, a hormone, a cytokine or a growth factor. In another embodiment, the therapeutic compound is immunostimulatory. In another embodiment, the therapeutic compound inhibits inflammatory or immune responses.

In one embodiment, the term "therapeutic", refers to a molecule, which when provided to a subject in need, provides a beneficial effect. In some cases, the molecule is therapeutic in that it functions to replace an absence or diminished presence of such a molecule in a subject. In one embodiment, the molecule is a nucleic acid coding for the expression of a protein is absent, such as in cases of an endogenous null mutant being compensated for by expression of the foreign protein. In other embodiments, the endogenous protein is mutated, and produces a non-functional protein, compensated for by the expression of a heterologous functional protein. In other embodiments, expression of a heterologous protein is additive to low endogenous levels, resulting in cumulative enhanced expression of a given protein. In other embodiments, the molecule stimulates a signalling cascade that provides for expression, or secretion, or others of a critical element for cellular or host functioning. In one embodiment, the therapeutic compound is a protein or polypeptide.

In one embodiment, the therapeutic protein may include cytokines, such as interferons or interleukins, or their receptors. Lack of expression of cytokines, or of the appropriate ones, has been implicated in susceptibility to diseases, and enhanced expression may lead to resistance to a number of infections. Expression patterns of cytokines may be altered to produce a beneficial effect, such as for example, a biasing of the immune response toward a Th1 type expression pattern, or a Th2 pattern in infection, or in autoimmune disease, wherein altered expression patterns may prove beneficial to the host.

In another embodiment, the therapeutic protein may comprise an enzyme, such as one involved in glycogen storage or breakDown. In another embodiment, the therapeutic protein comprises a transporter, such as an ion transporter, for example CFTR, or a glucose transporter, or other transporters whose deficiency, or inappropriate expression results in a variety of diseases.

In another embodiment, the therapeutic protein comprises a tumor suppressor, or pro-apoptotic compound, which alters progression of cancer-related events.

In another embodiment, the therapeutic protein expressed may be selected from the group consisting of natural or non-natural insulins, amylases, proteases, lipases, kinases, phosphatases, glycosyl transferases, trypsinogen, chymotrypsinogen, carboxypeptidases, hormones, ribonucleases, deoxyribonucleases, triacylglycerol lipase, phospholipase A2, elastases, amylases, blood clotting factors, UDP glucuronyl transferases, ornithine transcarbamoylases, cytochrome p450 enzymes, adenosine deaminases, serum thymic factors, thymic humoral factors, thymopoietins, growth hormones, somatomedins, costimulatory factors, antibodies, colony stimulating factors, erythropoietin, epidermal growth factors, hepatic erythropoietic factors (hepatopoietin), liver-cell growth factors, interleukins, interferons, negative growth factors, fibroblast growth factors, transforming growth factors of the α family, transforming growth factors of the β family, gastrins, secretins, cholecystokinins, somatostatins, serotonins, substance P and transcription factors.

In another embodiment, the therapeutic compound is immunogenic. In one embodiment, the term "immunogenic" refers to an ability to elicit an immune response. In one embodiment, the therapeutic compound elicits a "Th1" response, in a disease where a so-called "Th2" type response has developed, when the development of a so-called "Th1" type response is beneficial to the subject, or vice versa.

In another embodiment, the therapeutic compound of the present invention may comprise an immunomodulating protein. In one embodiment, the immunomodulating protein comprises cytokines, chemokines, complement or components, such as interleukins 1 to 15, interferons alpha, beta or gamma, tumour necrosis factor, granulocyte-macrophage colony stimulating factor (GM-CSF), macrophage colony stimulating factor (M-CSF), granulocyte colony stimulating factor (G-CSF), chemokines such as neutrophil activating protein (NAP), macrophage chemoattractant and activating factor (MCAF), RANTES, macrophage inflammatory peptides MIP-1a and MIP-1b, or complement components.

In another embodiment, a therapeutic compound of this invention may comprise a growth factor, or tissue-promoting factor. In one embodiment, the therapeutic compound is a bone morphogenetic protein, or OP-1, OP-2, BMP-5, BMP-6, BMP-2, BMP-3, BMP-4, BMP-9, DPP, Vg-1, 60A, or Vgr-1.

In another embodiment, this invention provides a method of tissue engineering comprising the step of contacting a cell with a composite scaffolding comprising a water-soluble tissue-promoting factor adsorbed onto a basic, inorganic material and a bio-degradable polymer which yields acidic degradation products, whereby degradation of the polymer yields acidic degradation products therefrom, which stimulates dissolution of the inorganic material and release of the water-soluble tissue-promoting factor, and whereby the cell responds to the tissue-promoting factor, promoting tissue formation, thereby providing a method of tissue engineering. In one embodiment, the tissue is bone or cartilage. In another embodiment, the tissue-promoting factor is a bone morphogenetic protein, a member of the TGF-β superfamily, or a member of the BMP signaling cascade.

In one embodiment, the term "contacting a cell" refers to both direct and indirect exposure of the cell to a composite microparticle or scaffolding of the invention. In one embodiment, contacting a cell may comprise direct interaction with the composite microparticle or scaffolding, or, in another emobodiment, indirect contact, such as via provision in a culture medium that surrounds the cell. It is to be understood that any means by which a cellular responsiveness is induced in response to a proximity of the cell to a composite microparticle or scaffolding of this invention is to be considered as part of this invention, and an embodiment thereof.

In one embodiment, according to this aspect of the invention, the contacted cell may comprise a plurality of cells derived from the tissue-type, which is for engineering. In another embodiment, the cell is a stem cell, which may be induced to differentiate to a cell type of the tissue that is desired for engineering. In one embodiment, the stem cell may itself elaborate factors promoting further tissue engineering. These tissue-promoting factors may, in one embodiment, be different, or in another embodiment, correspond to factors comprising the composite microparticles and/or scaffolding of this invention.

Composite microparticles comprising bone morphogenetic factor showed high levels and sustained release herein. Mesenchymal stem cells contacted with such composite microparticles responded in turn, via production of ALP, a marker for osteogenic cell differentiation. Osteoblasts have been shown to deposit bone in response to BMP-2.

In another embodiment, this invention provides a method of stimulating or enhancing bone repair, or maintaining or increasing bone volume, bone quality, or bone strength in the body of a subject in need, comprising the steps of: contacting a cell in the subject with a composite microparticle comprising a water-soluble osteogenesis-promoting factor adsorbed onto a basic, inorganic material and a bio-degradable polymer which yields acidic degradation products, whereby degradation of the polymer yields acidic degradation products therefrom, which stimulates dissolution of the inorganic material and release of the water-soluble tissue-promoting factor, and whereby the cell responds to the tissue-promoting factor, promoting tissue formation, thereby providing a method of tissue engineering.

In another embodiment, this invention provides a method of stimulating or enhancing bone repair, or maintaining or increasing bone volume, bone quality, or bone strength in the body of a subject in need, comprising the steps of: contacting a cell in the subject with a composite scaffolding, or composite controlled release system of this invention, comprising a water-soluble osteogenesis-promoting factor adsorbed onto a basic, inorganic material and a biodegradable polymer which yields acidic degradation products, whereby degradation of the polymer yields acidic degradation products therefrom, which stimulates dissolution of said inorganic material and release of the water-soluble tissue-promoting factor, and whereby the cell responds to the tissue-promoting factor, promoting tissue formation, thereby providing a method of tissue engineering. In another embodiment, release of the water-soluble osteogenesis-promoting factor occurs over a period of time.

Non-union bone fractures have been shown to be affected by the addition of BMP therapy, wherein bridging of the defect is seen, though the BMPs must be present for long periods of time, and present locally at the defect site. In one embodiment, the present invention provides a composite microparticle or scaffolding with long BMP retention times, tunable release kinetics, which provide the therapeutic at a desired constant rate, and in another embodiment, provide for sustained release.

In another embodiment, this invention provides a method of nucleic acid delivery, comprising contacting a cell with a composite microparticle comprising a nucleic acid adsorbed onto a basic, inorganic material and a bio-degradable polymer which yields acidic degradation products, whereby degradation of the polymer yields acidic degradation products therefrom, which stimulates dissolution of the inorganic material and release of the nucleic acid, thereby being a method of nucleic acid delivery. In one embodiment, the nucleic acid encodes for a compound, which is osteogenic, chondrogenic or angiogenic. In another embodiment, the nucleic acid encodes for an antibacterial, antiviral, antifungal or antiparasitic peptide or protein. In another embodiment, the nucleic acid encodes for a peptide or protein with cytotoxic or anti-cancer activity. In another embodiment, the nucleic acid encodes for an enzyme, a receptor, a channel protein, a hormone, a cytokine or a growth factor. In another embodiment, the nucleic acid encodes for a peptide or protein, which is immunostimulatory. In another embodiment, the nucleic acid encodes for a peptide or protein, which inhibits inflammatory or immune responses. In another embodiment, release of the nucleic acid occurs over a period of time.

In one embodiment, the cell may be any responsive cell, such as, in one embodiment, an epithelial cell, a lung cell, a kidney cell, a liver cell, a cardiocyte, an astrocyte, a glial cell, a prostate cell, a professional antigen presenting cell, a lymphocyte, an M cell, a pancreatic cell, a stem cell, a myoblast, a hepatocyte, an osteoblast, an osteocyte, an osteoclast, a chondrocyte, a chodroblast, or other bone or cartilage cells and may be used for applications as described in, for example, Wilson, J. M et al. (1988) Proc. Natl. Acad. Sci. USA 85:3014–3018; Armentano, D. et al. (1990) Proc. Natl. Acad. Sci. USA 87:6141–6145; Wolff, J. A. et al. (1990) Science 247:1465–1468; Chowdhury, J. R. et al. (1991) Science 254:1802–1805; Ferry, N. et al. (1991) Proc. Natl. Acad. Sci. USA 88:8377–8381; Wilson, J. M. et al. (1992) J. Biol. Chem. 267:963–967; Quantin, B. et al. (1992) Proc. Natl. Acad. Sci. USA 89:2581–2584; Dai, Y. et al. (1992) Proc. Natl. Acad. Sci. USA 89:10892–10895; van Beusechem, V. W. et al. (1992) Proc. Natl. Acad Sci. USA 89:7640–7644; Rosenfeld, M. A. et al. (1992) Cell 68:143–155; Kay, M. A. et al. (1992) Human Gene Therapy 3:641–647; Cristiano, R. J. et al. (1993) Proc. Natl. Acad Sci. USA 90:2122–2126; Hwu, P. et al. (1993) J. Immunol. 150:4104–4115; and Herz, J. and Gerard, R. D. (1993) Proc. Natl. Acad Sci. USA 90:2812–2816.

In another embodiment, this invention provides a method of controlled release drug delivery, comprising contacting a cell with a controlled release composite of this invention, for example, a composite microparticle, comprising a water-soluble drug adsorbed onto a basic, inorganic material and a bio-degradable polymer which yields acidic degradation products, whereby degradation of the polymer yields acidic degradation products therefrom, which stimulates dissolution of the inorganic material and release of the water-soluble drug over a period of time, thereby being a method of controlled release drug delivery. In one embodiment, the drug promotes osteogenesis, chondrogenesis or angiogenesis. In another embodiment, the drug exhibits antibacterial, antiviral, antifungal or antiparasitic activity. In another embodiment, the drug exhibits cytotoxic or anti-cancer activity. In another embodiment, the drug is immunostimulatory. In another embodiment, the drug inhibits inflammatory or immune responses.

It is to be understood that a drug or other therapeutic compound is envisioned for use in controlled release delivery by the method according to this aspect of the invention, and that any embodiment for a drug or therapeutic compound herein may be applied to this aspect of the invention, as well, and is to be considered as part of this invention.

In one embodiment, the design of the controlled release composite, such as, for example, composite particles or scaffolding of this invention provides an interplay between acid evolution from polymer degradation and dissolution of the basic inorganic phase, controlling release of the water-soluble compound. In one embodiment, the release profile may be regulated via a wide range of parameters, such as, in one embodiment, parameters affecting polymer degradation, or, in another embodiment, inorganic matrix dissolution, or in another embodiment, loading of the water-soluble compound.

In one embodiment, the controlled release composite, such as, for example, composite particles or scaffolding of this invention are so designed as to provide flexibility in the release profile of the adsorbed water-soluble compound, the type of compounds released, the formulation, shape, morphology or size of the particles or scaffolding, such as, in one embodiment, the ability to formulate as particles, films, bulk scaffolds, and others, each of which represents an embodiment herein. In one embodiment, the invention provides composites which are in the form of a gel, bulk scaffold, thin film or pellet, which, in another embodiment, comprises particles comprising the inorganic basic compound with adsorbed water-soluble compound and biodegradable polymer which releases acid degradation products. The particles comprising a particular scaffold, gel, thin film or pellet, may differ in their water-soluble compound, biodegradable polymer, polymer concentration, polymer molecular weight, type of inorganic material used, composition, size, or combination thereof.

Controlled release composites, including, for example, particles, scaffolds, films, etc., of this invention, may be administered to a subject, in one embodiment, in any effective, convenient manner including, for instance, administration by intravascular (i.v.), intramuscular (i.m.), intranasal (i.n.), subcutaneous (s.c.), oral, rectal, intravaginal delivery, or by any means in which the composite controlled release system can be delivered to tissue (e.g., needle or catheter). Alternatively, topical administration may be desired for insertion into epithelial cells. In another embodiment, the method of administration may be via aspiration or aerosol formulation.

In one embodiment, for administration to mammals, and particularly humans, it is expected that a physician will determine the actual dosage and duration of treatment, which will be most suitable for an individual and can vary with the age, weight and response of the particular individual.

The following examples are intended to illustrate but not limit the present invention.

EXAMPLES

Materials and Experimental Methods

Apatite Synthesis:

Hydroxyapatite (HAP) and carbonated apatite (CAP) were synthesized according to the method developed by Ahn et al. [Ahn, E. S., *Nanostructured Apatites as Orthopedic Biomaterials*, Ph.D. Thesis, Department of Chemical Engineering, Massachusetts Institute of Technology, Cambridge, Mass., 2001; Ahn, E. S. et al., *Nano Lett.* 2001, 1, 149–153; Ying, J. et al., U.S. Pat. No. 6,013,591 (2000)]. For the synthesis of HAP, 900 ml of 0.167 M $Ca(NO_3)_2$ (Fluka) and 900 ml of 0.100 M $(NH_4)_2HPO_4$ (Fluka) were prepared in distilled water. The pH of the $(NH_4)_2HPO_4$ solution was raised to 10.4 with ammonium hydroxide. The $Ca(NO_3)_2$ solution was added to the $(NH_4)_2HPO_4$ solution at a rate of ~3 ml/minutes. The resulting suspension was stirred at room temperature for 72 hours. After this aging step, the white precipitate was collected by centrifugation, washed with aqueous $NH_4OH$ solutions of decreasing pH, followed by two ethanol washes. The gel was air-dried overnight, then oven-dried at 120° C. for 24 hours. The dried gel was ground in a heated mortar and calcined at 550° C. for 2 hours (ramp rate of 10° C./min). After calcination, the HAP powder was sieved through a 45-μm mesh. CAP was synthesized by the same method but with the following modifications. $(NH_4)HCO_3$, the carbonate source, was added to the $(NH_4)_2HPO_4$ solution to a concentration of 0.100 M. After the ovendrying step, the gel was ground and sieved. The powder was not calcined to avoid driving off the carbonate groups at elevated temperatures.

For the synthesis of submicron-sized apatite particles, modifications were made to the above protocol to reduce agglomeration. Tween 80 (Aldrich) was added as a surfactant to constitute 10 v/v % of the $(NH_4)_2HPO_4/(NH_4)HCO_3$ solution. Apatite was collected and washed by ultrafiltration instead of centrifugation. The washed apatite was dried by lyophilization, which produced a fine, fluffy powder without the need for grinding or sieving. Calcination, which leads to grain growth, was not performed on these apatite powders. The hydroxyapatite and carbonated apatite thus prepared are referred to as sHAP and sCAP, respectively.

Two types of HAP powder were purchased from Berkeley Advanced Biomaterials, Inc. (BABI) as measures of comparison with our materials. The two BABI products were BABI-HAP-SP, with an advertised mean particle size of 5 µm, and BABI-HAP-N20, with an advertised mean size of 20 nm.

Characterization of Apatite

Powder X-ray diffraction (XRD) patterns of the various apatite powders were obtained with a Siemens D5000 θθ diffractometer (45 kV, 40 mA, Cu Kα). Grain size analyses were performed on the diffraction peaks using Scherrer's method. The BET surface areas of the apatite powders were determined by nitrogen adsorption on a Micromeritics ASAP 2000/2010 Analyzer. Particle size distribution was evaluated using a Horiba CAPA-300 Particle Size Analyzer.

Preparation of Apatite-Protein Complexes

Fluorescein isothiocyanate-bovine serum albumin (FITCBSA, Sigma) was used as a model protein. FITC-BSA was dissolved in distilled water and added to an aqueous suspension of HAP, sHAP, CAP, or sCAP. The suspension was stirred at room temperature for 16 hours to allow the adsorption of the protein onto the apatite. The BSA-apatite complex was collected by centrifugation, washed with distilled water, and lyophilized. BMP-2 (R&D Systems) was adsorbed onto apatite by the same procedure, except the adsorption time was reduced to 8 hours. The amount of protein adsorbed was determined by measuring the protein concentrations of the initial stock solution and the supernatant after adsorption, and taking the difference. FITC-BSA concentration was analyzed by Coomassie Plus total protein assay (Pierce). BMP-2 concentration was evaluated with an enzyme-linked immunosorbent assay (ELISA) kit (R&D Systems).

Maximum protein adsorption was determined for HAP, CAP, sHAP, sCAP, BABI-HAP-SP, and BABI-HAP-N20. Adsorption isotherms for FITC-BSA onto CAP and HAP at 4° C. and room temperature were obtained by varying the concentration of the initial FITC-BSA solution from 0.25 to 6.00 mg/ml. Adsorption times ranging from 0.5 hours to 7 days were used to determine the minimum amount of time required for maximum protein adsorption at room temperature.

To explore the possibility of adsorbing other types of proteins, proteins of different isoelectric point (IEP) and size were tested for adsorption onto CAP. These proteins (all from Sigma) included lysozyme (IEP=11, MW=14 kD), cytochrome C (IEP=10, MW=12.4 kD), and alcohol dehydrogenase (IEP=5.5, MW=141 kD). Protein stock solutions of 100–200 µg/ml were prepared with DI water. Each protein solution was added to 10 mg of CAP and allowed to stir for 8 h at room temperature.

The amount of protein adsorbed was expressed as a percentage of the amount of protein in the original stock solution.

Zeta potential measurements (Brookhaven ZetaPALS Zeta Potential Analyzer) were performed at pH 7 on CAP and HAP before and after the adsorption of FITC-BSA.

Effect of pH on the Dissolution of Apatite and the Release of Adsorbed Proteins

To study the effect of pH on the dissolution of apatite and the release of adsorbed proteins from apatite-BSA complexes, 10 mg of either CAP-BSA or HAP-BSA powder was added to microvials containing 1.5 ml of medium. The BSA loading on the apatites was 7.5 w/w/o (750 µg BSA per 10 mg of BSA-apatite complex). The medium was citrate buffer of pH 3 or 5. As a comparison, N,N-bis(2-hydroxyethyl)-2-aminoethanesulfonic acid (BES) buffer of physiological pH (pH 7.4) was also used. The vials were incubated in a 37° C. water bath for 8 weeks. At pre-determined time intervals of 1, 4, 7, 14, 21, 28, 42, and 56 days, the vials were centrifuged. Half of the supernatant (0.75 ml) was removed and filtered, and replaced with the same volume of fresh buffer. The vials were then returned to the water bath. The supernatants were stored at 4° C. until analysis by Coomassie Plus total protein assay for protein concentration. The results were used to construct a cumulative protein release profile for each apatite-protein complex at each pH.

Preparation of Composite Microparticles

Composite microparticles were synthesized by a modification of a solid-in-oil-in-water emulsion process previously used to encapsulate proteins in the solid state [Castellanos, I. J. et.al., Pharm. Pharmacol. 2001, 53, 167–178]. A typical synthesis involved dissolving 250 mg of PLGA (24 kD, Alkermes) in 2 ml of dichloromethane. To this polymer solution, 10 mg of protein-apatite (BSA, rhBMP-2-apatite) complex was added and vortexed to create a uniform suspension. The solid-in-oil suspension was homogenized in 50 ml of 0.1 w/v % aqueous methyl cellulose solution at 8000 rpm for 2 minutes at room temperature. The resulting solid-in-oil-in-water suspension was heated at 30° C. for 3 hours to drive off dichloromethane and solidify the particles. The particles were collected by centrifugation, washed with distilled water, and lyophilized. This protocol was systemically varied one parameter at a time to investigate the effect of different processing parameters.

Preparation of PLGA Microspheres by Double Emulsion Processing

As a standard for comparison, the double emulsion technique modified from Blanco et al. was used to prepare polymeric microspheres encapsulating proteins [Blanco, M. D. and M. J. Alonso, Eur. J. Pharm. Biopharm., 1997. 43: p. 287–294]. An aqueous solution of FITC-BSA was first created by dissolving 4 mg of the protein in 50 µl of DI water. This aqueous phase was added to an organic phase containing 250 mg of PLGA in 2 ml of dichloromethane. The two phases were homogenized at 8000 rpm for 2 minutes to form a water-in-oil (W/O) emulsion. The emulsion was then transferred to 50 ml of aqueous 0.1 w/v % methyl cellulose solution and homogenized at 8000 rpm for another 2 min to create a water-in-oil-in-water (W/O/W) emulsion. This double emulsion was stirred and heated at 30° C. for 3 h to drive off dichloromethane. The resulting microparticles were collected by centrifugation, washed 3 times with DI water, and freeze-dried to obtain the final product.

Characterization of Microparticle Morphology and Size

The morphology of the composite particles was evaluated by environmental scanning electron microscopy (ESEM, FEI/Philips XL30 FEG) at 6–7 kV. The average particle size and size distribution were determined by measuring the dimensions of a minimum of 100 particles under ESEM.

Evaluation of Encapsulation Efficiency of Composite Microparticles

To evaluate the protein content of the composite microparticles, the polymeric phase was first dissolved with 0.5 ml of dichloromethane per 10 mg of composite particles. 3 ml of citrate buffer of pH 2 was then added to the organic suspension to dissolve the apatitic phase. Prior testing showed that 3 ml of pH 2 citrate buffer was sufficient to dissolve more than 8 mg of apatite-protein complex. Among all the sets of composite particles that were prepared, the maximum loading of apatite-protein in 10 mg of composite particles was 2.65 mg. The dichloromethane-citrate buffer mixture was vortexed periodically over 2 days to allow protein extraction into the aqueous phase. The aqueous phase was then removed for protein concentration analysis by Coomassie Plus total protein assay (Pierce). The low pH of the citrate buffer sometimes led to the precipitation of BSA. To dissolve the protein precipitate, 1 ml of 0.1 N NaOH was added. The alkaline protein solution obtained was also measured for protein concentration. The total protein content of the composite particles was the summation of the quantities of protein measured in the citrate buffer and in the NaOH solution. Hence, the protein loading of the composite particles was calculated as:

$$\text{Protein Loading (\%)} = \frac{\text{Protein } Amt._{citrate\ buffer} + \text{Protein } Amt._{NaOH\ soln}}{\text{Mass of Composite Particles}} \times 100$$

The encapsulation efficiency was calculated as follows:

$$\text{Encapsulation Efficiency (\%)} = \frac{\text{Measured Protein Loading}}{\text{Theoretical Protein Loading}} \times 100$$

An alternative method of loading these composite particles with protein was to allow post-synthesis uptake of protein into blank PLGA-apatite composite particles. Both PLGA-CAP and PLGA-HAP composite particles were tested in triplicates. 15 mg of blank PLGA-apatite particles were mixed with 1 mg of FITC-BSA in 1 ml of DI water. The mixtures were allowed to stir at room temperature for 24 h, and were then centrifuged. The protein loading for each sample was derived from the difference between the protein concentration of the original stock solution and that of the supernatant.

Evaluation of in Vitro Release

Protein-loaded composite microparticles (30 mg) were re-suspended in 1.5 ml of pH 7.4 N, N-bis(2-hydroxyethyl)-2-aminoethanesulfonic acid (BES) buffer supplemented with 0.02 w/v % sodium azide. The samples were incubated at 37° C. At pre-determined time intervals (1, 4, 7, 14, 21, 28, 42, 56 . . . days, up to 20 weeks), the samples were centrifuged, 0.75 ml of the supernatant was withdrawn and replaced with 0.75 ml of fresh BES buffer. For samples containing FITC-BSA, the collected supernatant was filtered and assayed for fluorescence, and stored at 4° C. until further analysis of protein concentration with the Coomassie Plus total protein assay. For samples containing BMP-2, the collected supernatant was filtered and stored at −20° C. until evaluation by a BMP-2 ELISA kit. The protein concentration at each time point was used to construct cumulative release profiles.

Evaluation of Calcium Release from Composite Microparticles

The calcium concentration of release media incubated with composite microparticles was analyzed using a fluorescent calcium indicator, Rhod-5N (Molecular Probes). Rhod-5N is a rhodamine-based fluorophore that exhibits enhanced fluorescence (Ex/Em=551/576) when bound to calcium. It is sensitive in the range of 10 µM to 1 mM calcium.

PLGA-CAP composite microparticles prepared from polymers of different molecular weight were tested. In addition, one set of PLGA-CAP-BSA composite particles with a BSA loading of 1.67 w/w % was tested (polymer MW of 59 kD). The apatite loading for all sets of particles was 0.2 mg per mg of PLGA. For each set of composite particles, duplicates were prepared consisting of 30 mg of composite particles incubated in 1.5 ml of BES buffer (pH 7.4) at 37° C. The release medium was collected and renewed at 1, 4, 7, 14, 21, 28, and 42 days. To generate a calcium calibration curve, standards ranging in concentration from 10 µM to 1 mM were prepared using calcium nitrate tetrahydrate (Fluka).

Example 1

Construction of and Parameters Affecting Apatite-Polymer Composite Particles

Preparation of HAP and CAP yielded approximately the same particle size. XRD analysis of HAP and CAP (FIG. 1) demonstrated that CAP is less crystalline than HAP, and possessed a smaller grain size.

Figure 1A:
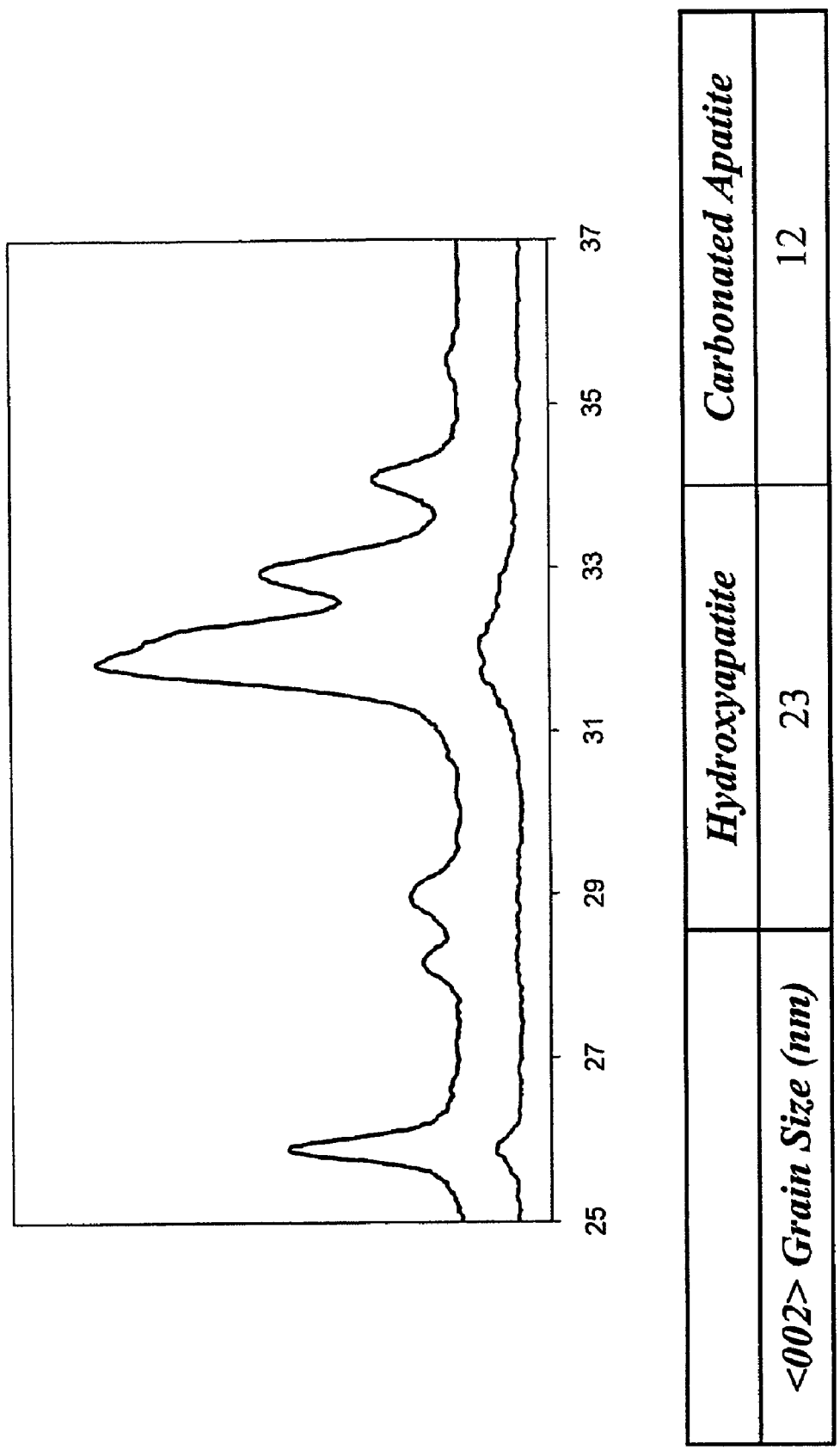
FIG. 1 demonstrates an XRD analysis of the synthesized Hydroxyapatite and carbonated Apatite. Grain size of the carbonated Apatite is significantly smaller than Hydroxyapatite.
Figure 1B:
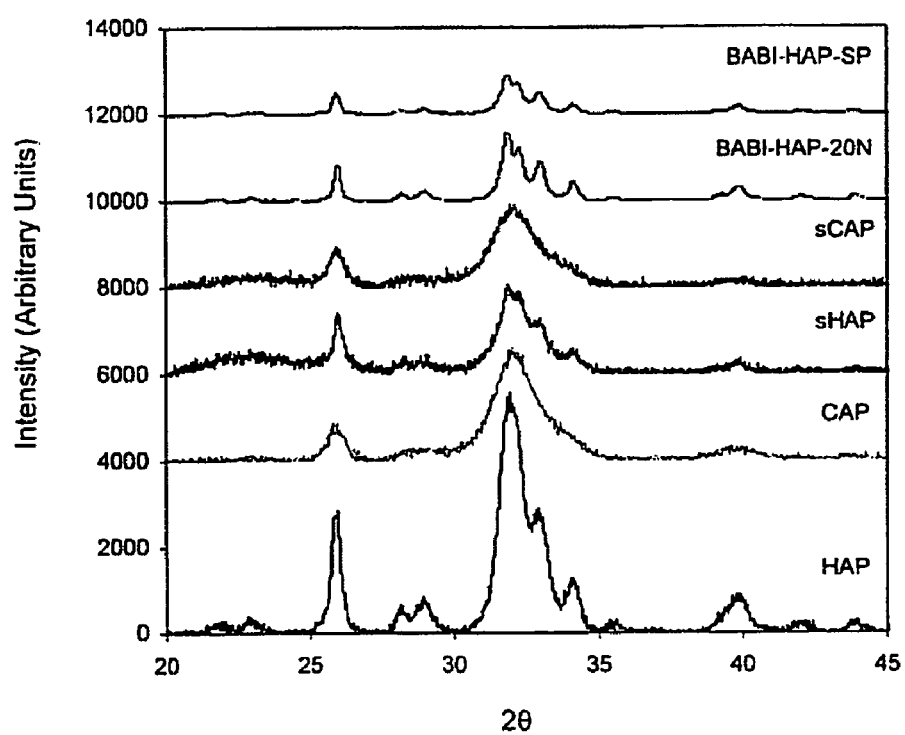

The preparation of apatite by chemical precipitation resulted in the formation of a pure apatitic phase, as evaluated by XRD (FIG. 1). Characteristic apatite peaks occur at 25.88° (002 plane) and 32.90° (300 plane). Calcination of HAP led to higher crystallinity, as indicated by the sharper and narrower peaks, though approximately the same particle size is seen (FIG. 1A). BABI-HAP-SP and BABI-HAP-N20, which were obtained from commercial sources, appeared crystalline and CAP, sCAP, and sHAP, which were prepared without calcination, were more amorphous (FIG. 1B).

The grain size of HAP was the highest among the apatites synthesized (Table 1.1). BABI-HAP-SP and BABI-HAP-N20, which were obtained from commercial sources, had grain sizes ~2 times that of HAP. CAP, sCAP, and sHAP, which were prepared without calcination, had smaller grain sizes.

TABLE 1.1

Grain Size And Particle Size Of Apatite Powders

| Apatite Sample | Grain Size (nm) | Average Particle Size (µm) |
|---|---|---|
| HAP | 23 | 5.3 |
| CAP | 12 | 6.8 |
| sHAP | 30 | 0.7 |

TABLE 1.1-continued

Grain Size And Particle Size Of Apatite Powders

| Apatite Sample | Grain Size (nm) | Average Particle Size (μm) |
|---|---|---|
| sCAP | 15 | 1.0 |
| BABI-HAP-SP | 47 | 4.5 |
| BABI-HAP-N20 | 43 | 0.6 |

HAP and CAP had approximately the same average particle size of 5–7 μm. (Table 1). The use of surfactant in the synthesis of sHAP and sCAP contributed to less agglomeration and submicron particle size. The measured particle size of BABI-HAP-SP was close to its advertised particle size of 5 μm, and was in the same range as HAP and CAP. However, the measured particle size of BABI-HAP-N20 was 30 times larger than its advertised size, probably as a result of agglomeration. Apatite particle size is important as it places a lower limit on the size of the apatite-polymer composite microparticles that can be formed. Smaller apatite particle size facilitates more uniform dispersion of apatite in the polymeric matrix, as well as the creation of smaller composite particles without phase separation.

Figure 2:
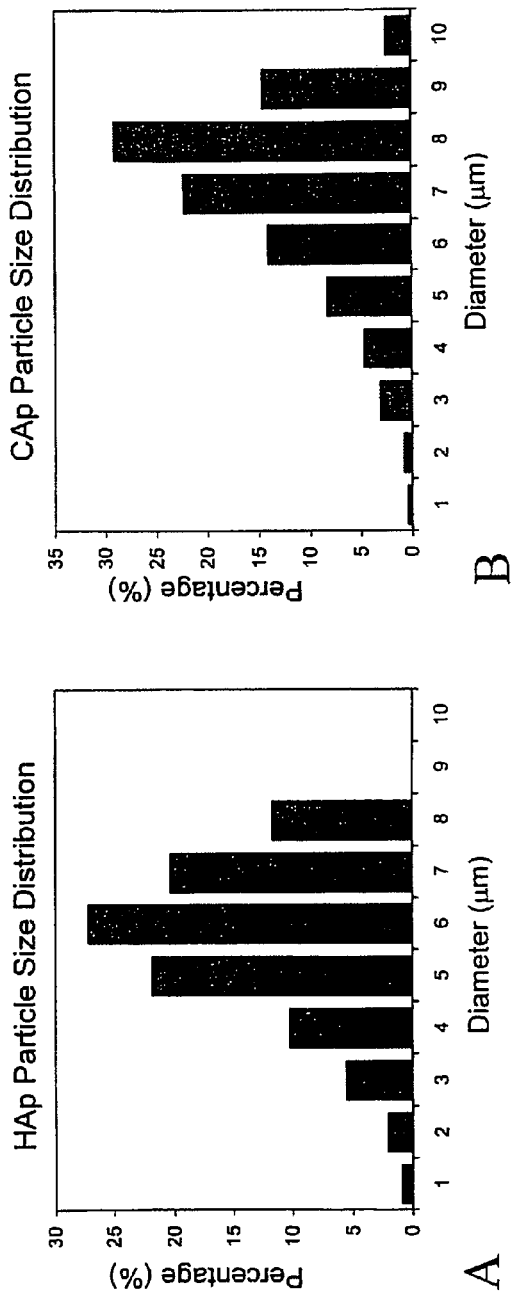
FIG. 2 demonstrates nitrogen adsorption and sedimentation analysis of the synthesized HAP and CAP particles. The uncalcined carbonated apatite (B) has a greater surface area than the HAP, with a greater percentage of the microparticles having a larger diameter, as compared to HAP (A). C-E: Adsorption isotherms for FITC-BSA onto HAP and CAP at room temperature (C, D); Adsorption of FITC-BSA onto HAP with time at room temperature(E)
Figure 2:
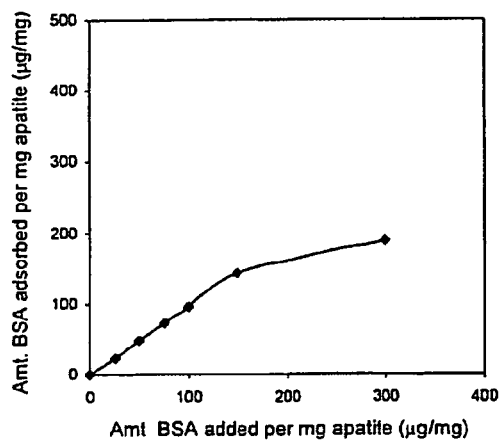
Figure 2:
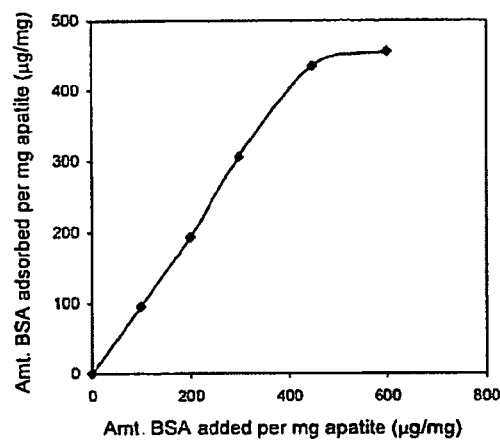
Figure 2:
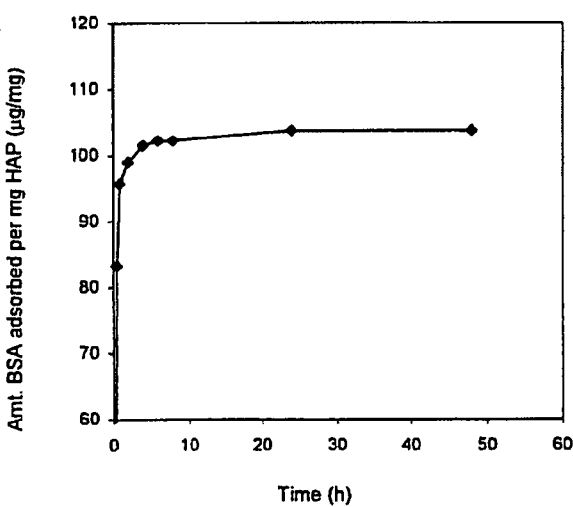

The physical characteristics of the apatite powders determined by nitrogen adsorption are tabulated in Table 1.2, and shown in FIG. 2A. CAP had a high BET surface area of 302 $m^2/g$ as well as a high pore volume, suggesting that it might be able to sequester larger amounts of protein than HAP. The hydroxyapatite powders obtained from BABI had lower surface area and pore volume, but higher mean pore radius than the apatites synthesized. Nitrogen adsorption studies on apatites synthesized with surfactant, namely, sCAP and sHAP, gave inconsistent measurements of BET surface area, likely due to surfactant remaining in the pores. Attempts to drive off this residual surfactant by gentle calcination to 300° C. resulted in discoloration of the apatite powders and further reduction in surface area (Data not shown).

TABLE 1.2

BET surface area, pore volume, and mean pore radius of apatites.

| Property | CAP | HAP | BABI-HAP-SP | BABI-HAP-N20 |
|---|---|---|---|---|
| BET Surface Area ($m^2/g$) | 302 | 86 | 48 | 53 |
| Pore Volume ($cm^3/g$) | 1.24 | 0.52 | 0.18 | 0.27 |
| Mean Pore Radius (nm) | 8.2 | 12.2 | 24 | 36 |

Sedimentation analysis indicated that a greater percentage of CAP particles had a larger size distribution as compared to HAP (FIG. 2B).

The maximum FITC-BSA adsorption capacities of various apatites obtained are summarized in Table 1.3. BABI-HAP-SP and BABI-HAP-N20 were found to have lower capacities for adsorbing protein, which is in line with their lower surface areas (Table 1.2). In particular, the surface area and protein adsorption capacity of BABI-HAP-N20 was low although it had the smallest particle size at 600 nm. In contrast, sHAP that was synthesized with surfactant had approximately the same particle size but adsorbed more than thrice the amount of protein.

TABLE 1.3

Protein adsorption capacity of various apatites

| Apatite Sample | Maximum BSA Adsorption (w/w %) |
|---|---|
| HAP | 15.9 |
| CAP | 31.4 |
| sHAP | 25.3 |
| sCAP | 21.3 |
| BABI-HAP-SP | 7.1 |
| BABI-HAP-N20 | 8.0 |

The room temperature adsorption isotherms of FITC-BSA onto CAP and HAP are shown in FIGS. 2C and D. The value of the plateau was taken as the maximum amount of protein adsorbed for the given mass of apatite used. These are the values tabulated in Table 1.3. The maximum amount of FITC-BSA adsorbed onto CAP was 2.4 times higher than the amount adsorbed onto HAP, although the BET surface area of CAP was 3.5 times higher (Table 1.2). The availability of surface area for adsorption was likely constrained by the pore size of the material. The mean pore size of CAP was 8.2 nm, which is equivalent to the hydrodynamic diameter of a BSA molecule. Therefore, pores at the smaller end of the distribution were inaccessible to BSA. Even in larger pores, the adsorption of one BSA molecule could have blocked off passage to the rest of the pore, thereby reducing the surface area available for protein adsorption.

Protein adsorption onto apatite was found to be a rapid process, and maximum adsorption could be achieved within 6 hours. A representative profile for adsorption onto HAP is shown in FIG. 2E. The minimum adsorption time required for maximum protein adsorption should be used to reduce processing time and exposure of sensitive proteins to elevated temperatures. However, in the case of FITC-BSA, which is a comparatively stable protein, adsorption was typically conducted overnight for 16 hours. For the adsorption of bone morphogenetic proteins, which is discussed below, the adsorption time was shortened.

The ability of apatite to adsorb other types of proteins was tested using a series of proteins of different isoelectric points (IEP) and sizes (Table 1.4). FITC-BSA is included as a reference. The amount of protein adsorbed is expressed as a percentage of the total amount of protein in the initial stock solution. The apatite used, CAP, was found to be capable of adsorbing a high percentage of all the proteins tested, with the exception of lysozyme. Only 24% of the lysozyme added to the apatite suspension was adsorbed. This lower affinity could be attributed to the rigid structure of lysozyme, which causes it to only partially unfold during adsorption and make fewer contacts with the substrate.

TABLE 1.4

Adsorption of proteins of different IEP and size onto CAP.

| Protein | Isoelectric Point | Molecular Weight (kD) | Amt. Adsorbed (%) |
|---|---|---|---|
| FITC-BSA | 4.7 | 66 | 99.2 |
| Lysozyme | 11 | 14 | 23.7 |
| Cytochrome C | 10 | 12 | 96.9 |
| Alcohol Dehydrogenase | 5.5 | 141 | 97.5 |

The zeta potential of CAP at pH 7 was found to be slightly negative (Table 1.5). HAP, which was also negatively charged, had a higher zeta potential. A higher zeta potential is related to increased stability of the suspension, as the charged particles repel one another and prevent agglomeration. Hence, a suspension of higher zeta potential can be expected to have lower particle size. Indeed, HAP had a smaller particle size than CAP (Table 1.5). Upon the adsorption of BSA (IEP =4.7), which is negatively charged at pH 7, the zeta potential of both CAP and HAP rose in magnitude. The particle size of CAP-BSA and HAP-BSA were also reduced correspondingly.

TABLE 1.5

Zeta potential and particle size of apatites and apatite-BSA complexes

| Sample | CAP | HAP | CAP-BSA | HAP-BSA |
|---|---|---|---|---|
| Zeta Potential at pH 7 (mV) | −2.82 ± 1.78 | −11.19 ± 2.12 | −18.59 ± 0.66 | −22.16 ± 1.81 |
| Particle Size (μm) | 6.8 ± 1.7 | 5.3 ± 1.5 | 5.8 ± 1.8 | 3.8 ± 2.1 |

As BSA and apatite are both negatively charged at pH 7, in this instance, electrostatic interactions are not the driving force for protein adsorption. The surface of bare hydroxyapatite has been found to be hydrophobic, leading researchers to suggest that hydrophobic interactions between BSA and hydroxyapatite induce adsorption. BSA is considered a "floppy" protein with high conformational adaptability that can expose hydrophobic groups for interactions with the surface. Other mechanisms of protein adsorption include ion-exchange and hydrogen bonding. Therefore, protein adsorption onto apatite is not limited to proteins that are oppositely charged at the pH of interest. Both positively charged proteins, including cytochrome C and bone morphogenetic proteins (as described further hereinbelow) and negatively charged proteins such as BSA and alcohol dehydrogenase were found to adsorb onto CAP (Table 1.4).

Effect of ph on Protein Release from Apatite-Protein Complexes

Figure 3:
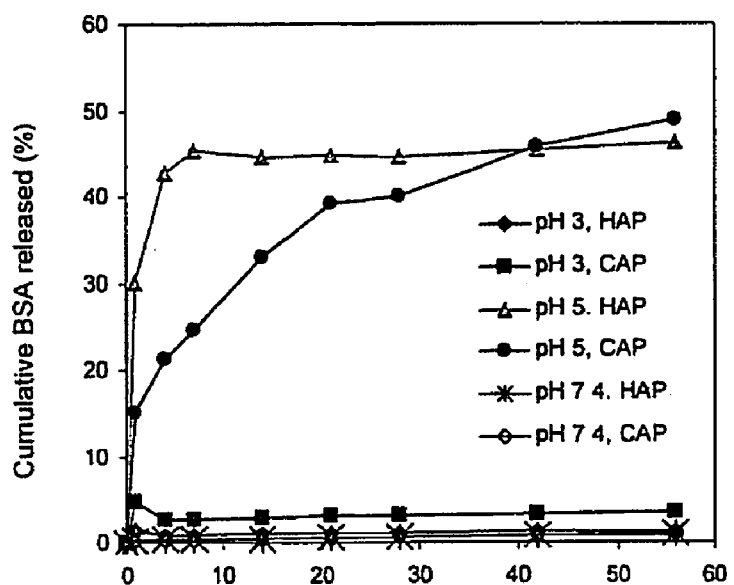
FIG. 3 demonstrates the release of BSA from HAP-BSA and CAP-BSA complexes in buffers of pH 3, 5, and 7.4.

The effect of pH on the release of BSA from apatite-BSA complexes is shown in FIG. 3. It was hypothesized that, since apatite is basic, its dissolution in an acidic medium would cause proteins sequestered on its surface or within its pores to be released. At the physiological pH of 7.4, protein release was very low and almost negligible over the testing period of 8 weeks. One additional data point was obtained at 436 days for pH 7.4, indicating that even after this extended period of time, only 2.6% and 1.5% of the protein had been released from the HAP-BSA and CAP-BSA complexes, respectively. Hence, under neutral pH conditions, the affinity of apatite for BSA remained high and apatite dissolution was low, even over a time course of more than one year.

Lowering of the pH to 5 led to a sharp increase in protein release from both the HAP-BSA and CAP-BSA complexes, but with different profiles. The HAP-BSA complex released 45% of its loaded protein in the first week, but the release plateaued thereafter. Protein release from CAP-BSA was more gradual and constant over the period tested. A possible explanation for the observed difference is that HAP, being less porous, holds a larger proportion of BSA on its surface whereas CAP has a more even distribution of BSA on its surface and in its pores. Any acid that is present erodes the surface of the apatite first, resulting in a large burst of protein from HAP-BSA. In the case of CAP-BSA, the protein is released gradually as acids dissolve deeper and deeper layers of the apatite. However, when the pH was further lowered to 3, release was observed to fall to levels approaching those at pH 7.4. The low pH might have induced protein precipitation.

Figure 4:
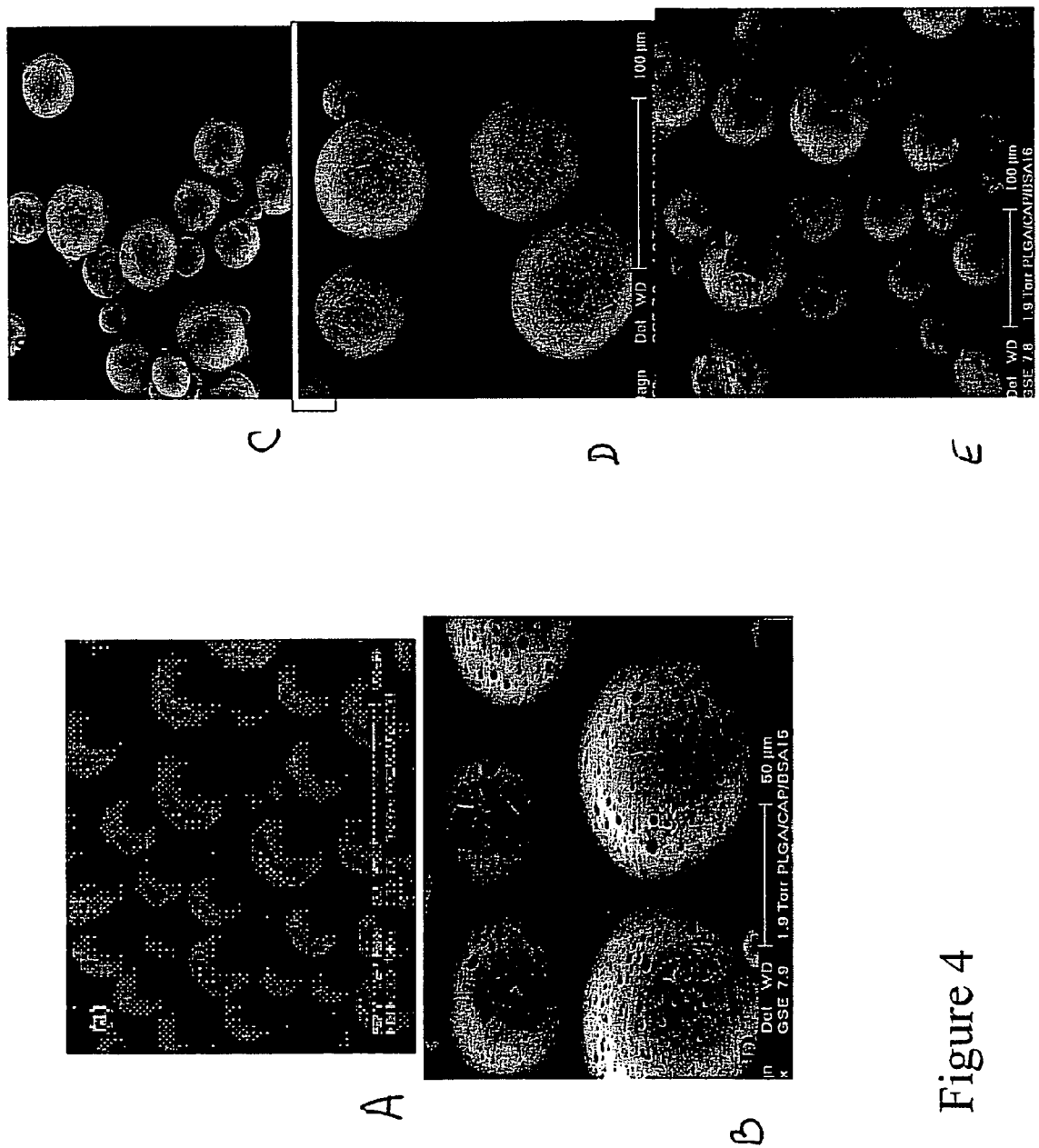
FIG. 4 demonstrates ESEM micrographs of composite microparticles prepared from sCAP (A), CAP (B), particles prepared as in b, but at double the homogenization speed (C), with double the concentration of the polymer (D), or with double the surfactant solution volume (E). ESEM micrographs of composite microparticles prepared from CAP and (F) 13 kD PLGA and (G) 50/50 blend of 13 kD and 24 kD PLGA FIG. 5 demonstrates protein release from composite microparticles in comparison to BSA encapsulated in PLGA microspheres prepared via w/o/w emulsion methods.
Figure 4F:
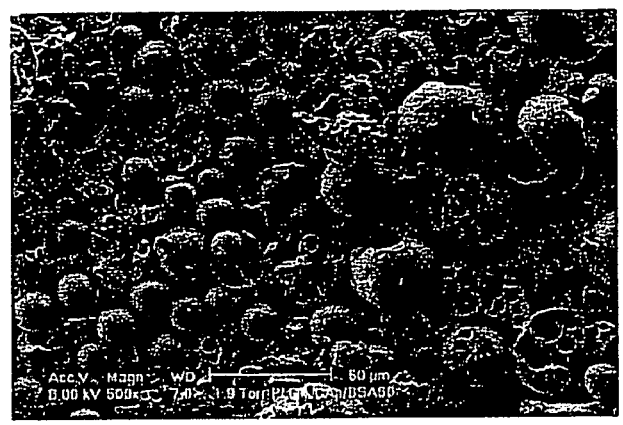
Figure 4G:
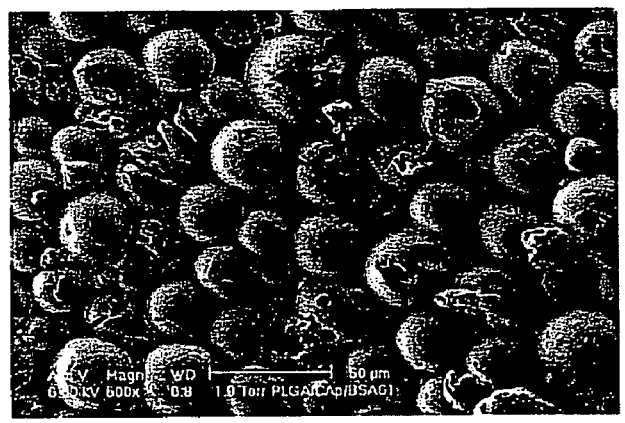

ESEM micrographs of two representative sets of composite microparticles are shown in FIG. 4. Both sets of particles have an average diameter of ~40 μm. Particles prepared from submicron-sized sCAP (a) have smoother surfaces whereas particles containing micron-sized CAP (B) appear rougher and more porous. The effect of various processing parameters on the size of the composite particles is summarized hereinabove, with ESEM preparations (FIGS. 4C, D, E) of microparticles prepared by via doubling homogenization speed, polymer concentration or surfactant solution volume, shown as well. FIGS. 4F and G illustrates the effect of blending in a higher molecular weight polymer. Particles prepared from 13 kD PLGA were smaller (~20 μm) and contained a larger proportion of non-spherical debris (F), while the addition of 24 kD PLGA led to slightly larger (~23 μm) and more spherical particles (G).

The effect of various processing parameters on the size of the composite particles is summarized in Table 1.6. For each parameter, low and high values around a midpoint were investigated to obtain a sense of the general trend. Variations that caused higher shear during homogenization led to the creation of smaller particles. For example, increase in homogenization speed and time directly increased the amount of shear experienced by the suspension. Decrease in polymer solution concentration and polymer molecular weight reduced the viscosity of the organic phase and also reduced particle size concomitantly.

TABLE 1.6

Effect Of Processing Parameters On Composite Particle Size

| Processing Parameters Particle | Size (μm) |
|---|---|
| Standard processing conditions as described - | 41 ± 12 |
| Increase homogenization speed to 12000 rpm | 30 ± 8 |
| Increase homogenization speed to 16000 rpm (FIG. 1c) | 27 ± 8 |
| Decrease homogenization time to 1 min | 55 ± 21 |
| Increase homogenization time to 4 min | 31 ± 10 |
| Increase $CH_2Cl_2$ volume to 4 ml | 27 ± 8 |
| Decrease in $CH_2Cl_2$ volume to 1 ml (FIG. 1d) | 65 ± 24 |
| Increase aqueous surfactant volume to 100 ml (FIG. 1e) | 51 ± 15 |
| Reduce aqueous surfactant volume to 25 ml | 35 ± 12 |
| Increase CAP-BSA complex loading to 30 mg | 37 ± 13 |
| Increase CAP-BSA complex loading to 50 mg | 37 ± 12 |
| Use of lower molecular weight PLGA (6 kD) | 23 ± 7 |
| Decrease apatite particle size to 1 μm (use of sCAP) | 44 ± 13 |
| Use of higher molecular weight PLGA (59 kD) | 45 ± 15 |
| Blending in 60 wt % PLA (15–25 kD) | 44 ± 12 |
| Blending in 20 wt % PLA (15–25 kD) | 42 ± 13 |
| Blending in 10 wt % PEG (3.4 kD) | 37 ± 12 |
| Blending in 30 wt % PEG (3.4 kD) | 23 ± 7 |

Encapsulation Efficiency of Protein in Composite Microparticles

More than 60 formulations of BSA-loaded composite microparticles were prepared, differing in polymer molecular weight, polymer blend, apatite type, apatite particle size, etc. All 60 formulations were tested for encapsulation efficiency, and the average was found to be 69.8%±19.9%. The multi-step nature of the extraction process used to determine encapsulation efficiency might have led to under-estimations as a result of protein loss at each step, however, the average encapsulation efficiency was high and comparable to that of particles prepared by the double emulsion technique. The encapsulation efficiency of selected formulations is shown in Table 1.7.

TABLE 1.7

Encapsulation Efficiency Of Selected BSA-Loaded Composite Microparticles.

Formulation

| Polymer | Polymer MW | AP-BSA Complex* | Theoretical BSA Loading♦ | Encapsulation Efficiency |
|---|---|---|---|---|
| PLGA | 6 kD | CAP-BSA (15 w/w %) | 1.5 w/w % | 77.1% |
| PLGA | 24 kD | CAP-BSA (15 w/w %) | 1.5 w/w % | 52.1% |
| PLGA | 24 kD | CAP-BSA (8 w/w %) | 2.2 w/w % | 68.7% |
| PLGA | 24 kD | HAP-BSA (20 w/w %) | 2.0 w/w % | 73.8% |
| PLGA | 59 kD | CAP-BSA (15 w/w %) | 1.5 w/w % | 50.9% |
| PLA | 10–15 kD | CAP-BSA (15 w/w %) | 1.5 w/w % | 57.9% |
| PLGA + PEG (7:3) | 24 kD, 70 kD | CAP-BSA (9 w/w %) | 0.9 w/w % | 94.0% |

*values in parentheses refer to the weight percent of the apatite-BSA complex in the composite microparticles.
♦weight percent of BSA in the composite microparticles.

The maximum amount of protein that could be loaded into blank composite particles post-synthesis was 0.26 and 0.28 w/w% for PLGA-CAP and PLGA-HAP particles, respectively. If the apatite powders had been pre-adsorbed with protein, the maximum theoretical loading would have been 5.3 and 2.7 w/w% for PLGA-CAP and PLGA-HAP particles, respectively. Thus, post-synthesis loading of protein is inefficient. The low uptake of protein into the particles was expected, as the apatite, being embedded in the PLGA matrix, was shielded from the protein. In addition, PLGA is not known to have a particularly high affinity for proteins. Hence, the pre-adsorption of protein onto apatite is an important step in ensuring adequate and appropriate protein loading of these composite particles for use in controlled delivery applications.

Example 2

Release Kinetics are a Function of Microparticle Composite Composition

Figure 5:
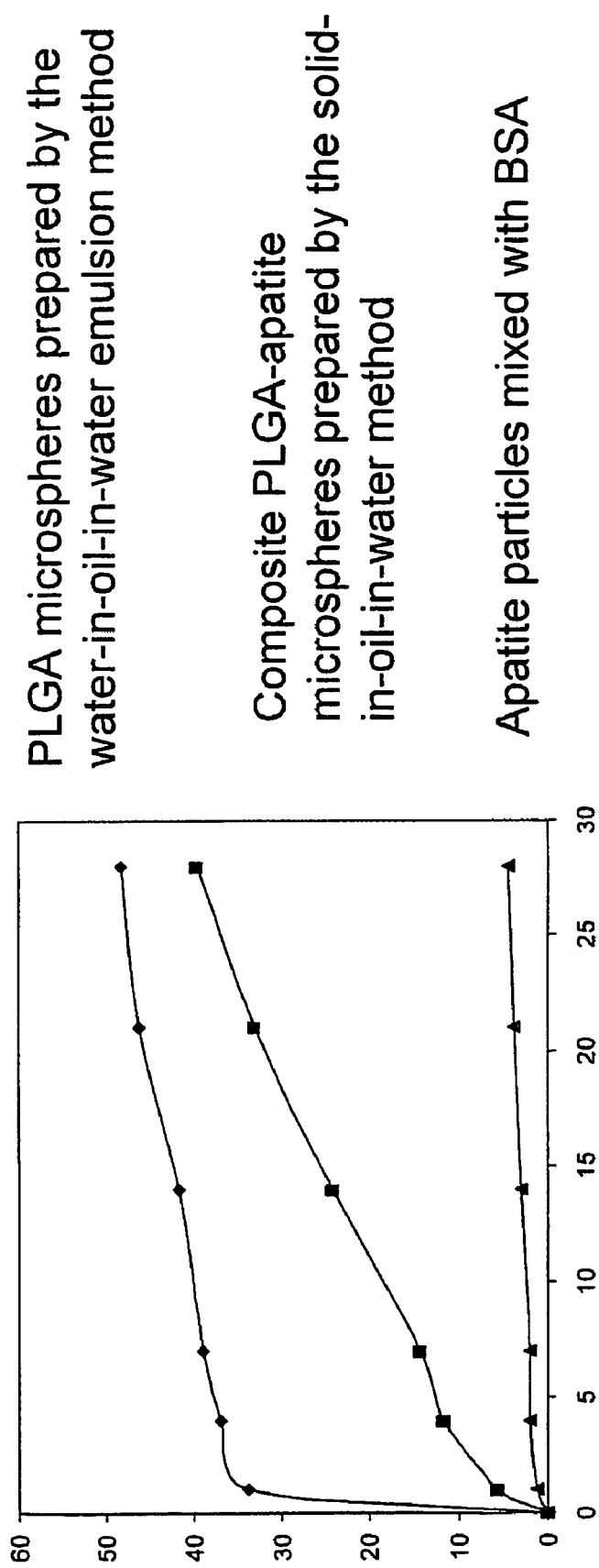

Microparticle protein release is a function of microsphere preparation. PLGA microspheres prepared via a water-in-oil-in-water emulsion method showed a high initial burst, with a sustained release, while composite PLGA-apatite microspheres prepared via a solid-in-oil-in-water method exhibit a low initial burst, with release kinetics approximating that of zero-order (FIG. 5). Apatite particles adsorbed with BSA show little release in comparison.

Figure 6:
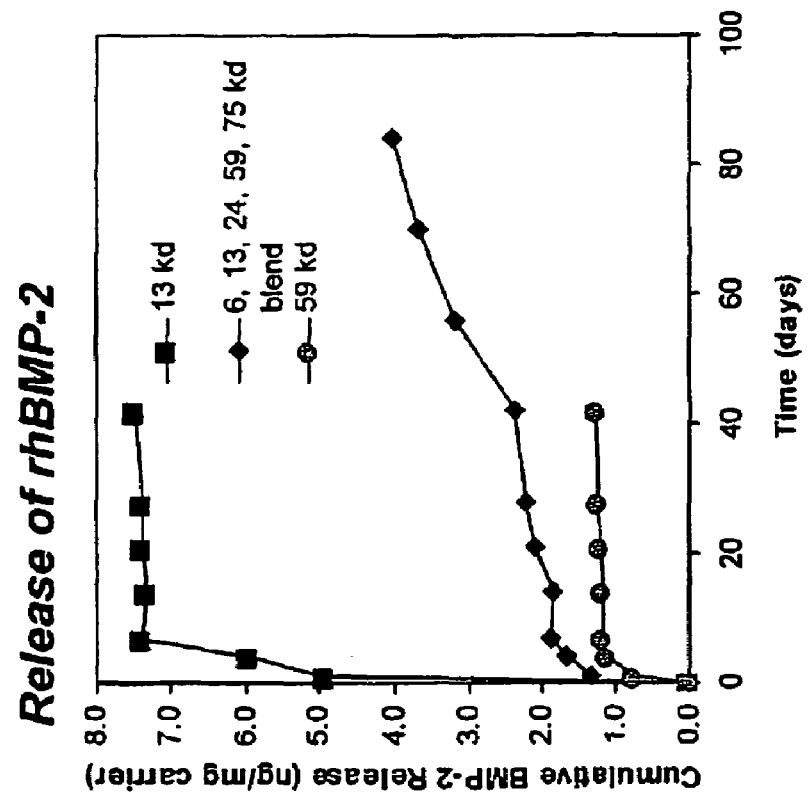
FIG. 6 demonstrates the effects of PLGA molecular weight on encapsulated protein release. Encapsulated FITC-BSA (15 µg/mg carrier) (A), or BMP-2 (64.5 ng/mg carrier) (B), in PLGA, with molecular weights as indicated, including (in (B)) a blend of particles comprising several PLGA molecular weights, or (C) blends of PLGA of different molecular weights.
Figure 6:
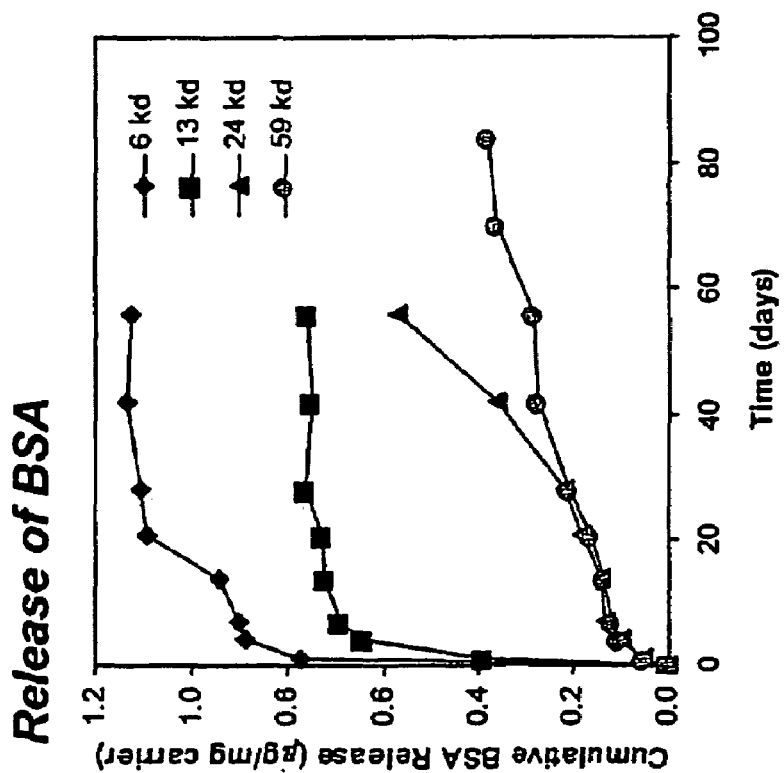
Figure 6C:
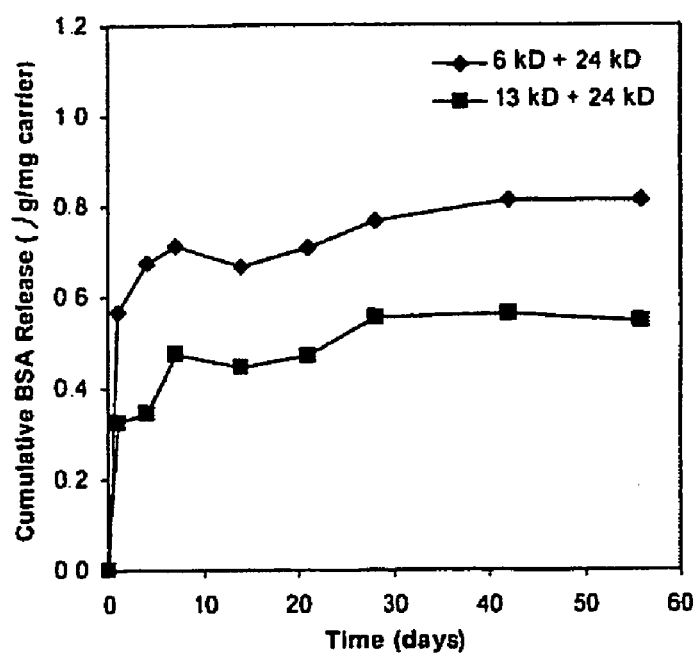

The molecular weight of a biodegradable polymer influences its degradation rate and lifetime. As molecular weight increases, degradation becomes slower and longevity is extended. Apatite-polymer composite particles were prepared from PLGA of different molecular weights ranging from 6 kD to 59 kD. The onset of the accelerated phase of protein release was observed to occur at different times depending on the molecular weight of the polymer used (FIG. 6A). For particles fabricated from the short-chained, 6 kD and 13 kD PLGA, the rapid release phase began immediately. An upturn in the release profile was seen at ~4 weeks for 24 kD PLGA, whereas release remained gradual up to 8 weeks for 59 kD PLGA. Such control of release rate by polymer molecular weight may be useful in sequential release, such as to direct the debut of a protein in a wound healing process. Polymers of different molecular weights could also be blended together to equalize the production of acid over time. Through the use of an equi-proportion blend of 6, 13, 24, 59 and 75 kD PLGA, a sustained and gradual release of BMP-2 was obtained (FIG. 6B). An observed slowing of the rapid protein release from low molecular polymers (6 and 13 kD PLGA) occurred with the blending of an equi-proportion of a higher molecular weight polymer (24 kD PLGA) (FIG. 6C) with the lower molecular weight PLGA.

It is possible, however, to manipulate the microparticles such that constant apatite and BSA loading is achieved. Processing parameters were adjusted to obtain particles of different sizes, with comparable apatite-BSA loading. Protein release measured in vitro, at 37° C. (FIG. 7A) indicated that comparable cumulative BSA was released from the particles.

When the amount of rhBMP-2 was held constant while the loading of apatite in composite microparticles was varied from 18 to 45 mg per 250 mg of polymer, rhBMP-2 release was found to decrease with increasing apatite loading (FIG. 7B). For the release of a fixed amount of protein, a higher apatite loading requires a larger amount of apatite to be dissolved, corresponding to a greater extent of polymer degradation. In addition, apatite served as a buffer, mitigating the acidity within the composite particles and diminishing the autocatalytic effect of pH on polymer hydrolysis. Hence, the apatite served towards dampening the protein release.

Example 3

Manipulation of the Polymer Influences Protein Release Rates

In order to determine what contribution the properties of the polymer play in protein release, composite particles were synthesized from blends of PLGA (50:50 copolymer) and poly (lactic acid) (PLA), which were measured for their rate of protein release. Lactic acid (LA) contains a methyl group that augments its hydrophobicity relative to glycolic acid (GA), hence, PLA is more hydrophobic. Because it is a homopolymer, PLA is also more crystalline than PLGA, which is a random copolymer of LA and GA. An increase in polymer hydrophobicity would delay water penetration, polymer degradation and acid production, and consequently, reduce protein release. This parameter could be varied by using different types, blends, or compositions of polymers. For example, the LA to GA ratio in PLGA could be varied to obtain a range of hydrophobicities and degradation rates. Increased proportion of PLA in the composite particles decreased the release rate of BSA, in vitro (FIG. 8A). Since lactic acid (LA) contains a methyl group that augments its hydrophobicity relative to glycolic acid (GA), hence, PLA is more hydrophobic than PLGA. An increase in polymer hydrophobicity delayed water penetration and polymer degradation, and consequently, reduced protein release from composite particles. This parameter could be adjusted by using different types, blends, or compositions of polymers. For example, the LA to GA ratio in PLGA could be varied to obtain a range of hydrophobicities and degradation rates.

Increasing polymer hydrophobicity by the addition of PLA led to a surprising enhancement of rhBMP-2 release with increasing polymer hydrophobicity. Polymer hydrophobicity was expected to reduce water penetration and polymer degradation, and hence, decrease protein release, as was seen with BSA. The unexpected result may be due to enhanced detection, since release of structurally intact, biologically active protein was measured, as opposed to measurement of the total release of protein. The determination of rhBMP-2 concentration by ELISA is highly specific; rhBMP-2 molecules have to be of the appropriate conformation for binding to antibodies. Denatured rhBMP-2 molecules are not detected by ELISA. Therefore, higher polymer hydrophobicity could have led to a less aggressive pH environment within the composite microparticles, contributing to less protein denaturation and greater release of bioactive rhBMP-2.

Figure 9:
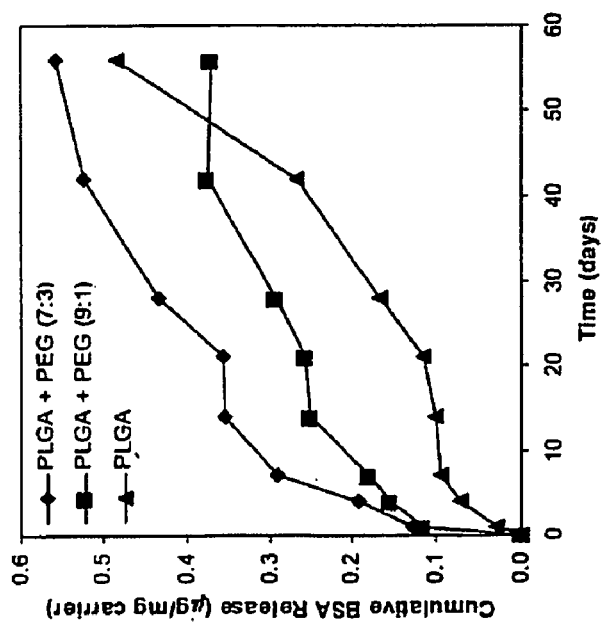
FIG. 9 demonstrates the effect of incorporating a hydrophilic polymer (PEG, 3.4 kD) on protein release. Particles contained 9 µg of FITC-BSA per mg carrier. Molecular weight of PLGA was 24 kD.

Polyethylene glycol (PEG), a hydrophilic, biocompatible, and non-degradable polymer, was blended with PLGA in the fabrication of composite particles. Increase in PEG content led to faster initial release (FIG. 9). All release profiles showed an upturn at approximately 21 days, which corresponded to the degradation of 24 kD. The hydrophilicity of PEG draws water into the particles where the PEG chains reside. In addition, PEG might leach out of the polymer matrix, leaving behind pores. The aqueous channels thus formed would facilitate water penetration and PLGA hydrolysis, as well as protein diffusion out of the particles, hence incorporation of the hydrophilic polymer increased the rate of release.

Example 4

Figure 10:
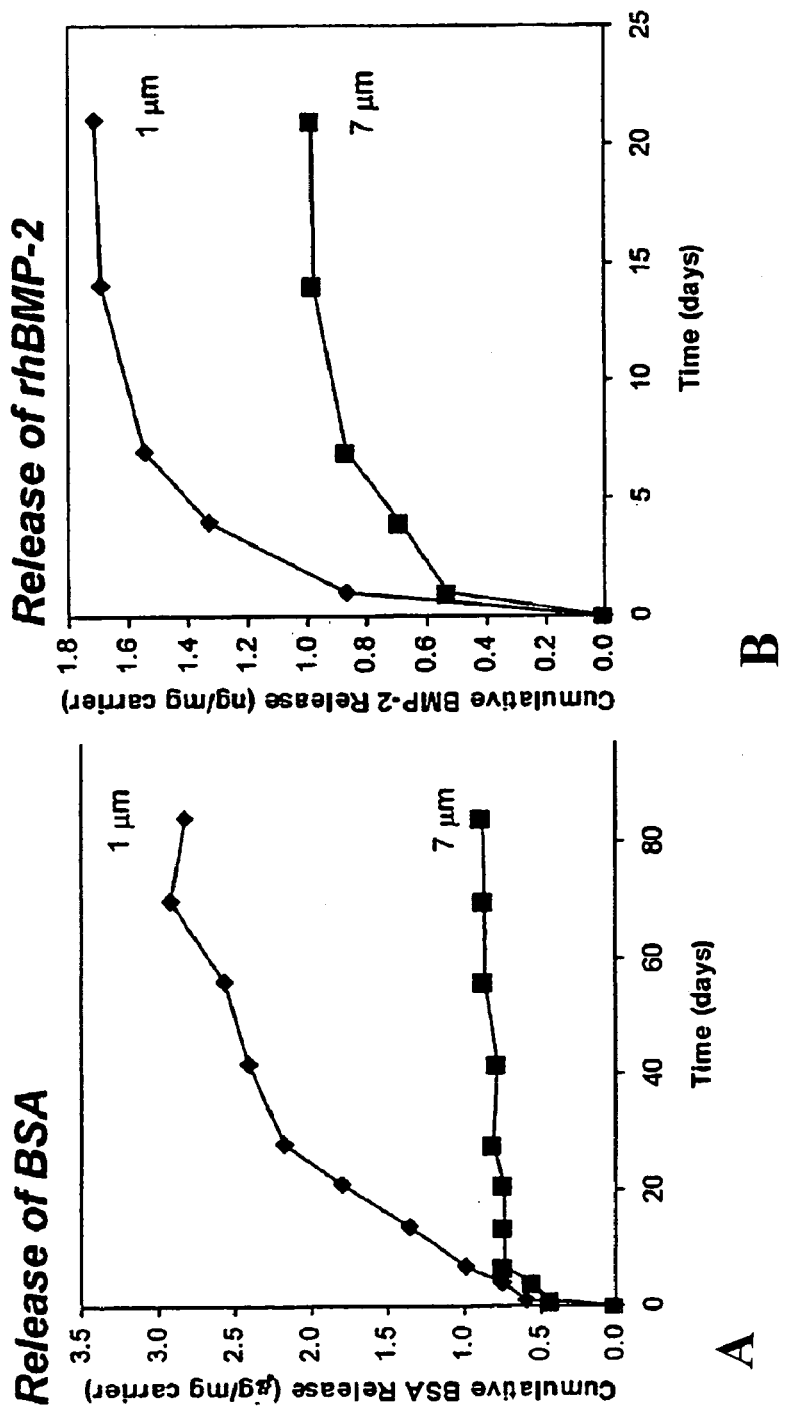
FIG. 10 demonstrates the effect of apatite particle size on protein release. Particles were fabricated from 59 kD PLGA and contained 18 µg of FITC-BSA per mg carrier (a), or rhBMP-2 (64.5 ng/mg carrier) (b). Protein release is enhanced when 1 µm-sized apatite particles are incorporated into the composite microparticles.

Varying Parameters Related to Apatite-Protein Complexes Affects the Rate of Protein Release In order to determine the effect of apatite particle size on protein release, CAP-BSA complexes prepared from sCAP (1 μm) and CAP (7 μm) were incorporated into composite particles. Reducing the apatite particle size resulted in release that more closely approximated zero-order for a longer period of time (FIG. 10). In contrast, the release plateaued after the first week of release from composite particles containing the larger, 7 μm-sized CAP particles. Similarly, rhBMP-2 release in composite microparticles comprising 59 kD PLGA was enhanced when 1 μm-sized apatite particles were incorporated in the composite particles, as compared to 7 μm (FIG. 10B).

For a given amount of acid produced by polymer degradation, a certain amount of apatite would be dissolved. Consequently, the protein adsorbed on that amount of apatite would be released. For small apatite particles, most of the area available for protein adsorption is on the surface of the particles due to their higher surface/volume ratio, and their lower porosity and pore size compared to larger particles. (SCAP has porosity of 0.27 cm3/g and mean pore size of 4.2 nm compared to porosity of 1.24 cm3/g and mean pore size of 8.2 nm for CAP.) As the surface of the apatite particles is gradually eroded by acid dissolution, the protein is released. For larger, porous apatite particles, the protein may be adsorbed on the surface as well as within the pores inside the particles. To free the protein adsorbed within the pores, a larger volume of apatite has to be dissolved. This difference in adsorption site may account for the difference in the release profiles for the 1 μm- and 7 μm-sized apatite particles.

Figure 11:
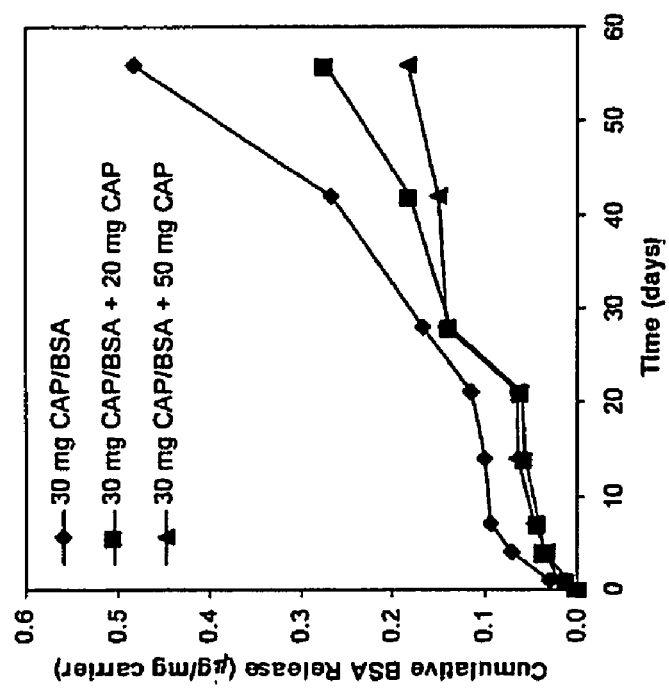
FIG. 11 demonstrates the effect of buffering apatite on protein release. Particles were fabricated form 24 kD PLGA and contained 9 (diamonds), 8.4 (squares) and 7.6 (triangles) µg of FITC-BSA per mg carrier.

In addition to apatite-protein complexes, varying amounts of bare apatite with no adsorbed protein, referred to as "buffering apatite", was loaded into the composite particles. As the proportion of buffering apatite was raised, the protein release rate decreased (FIG. 11). Protein release was dependent on the dissolution of apatite by acidic polymer degradation products. By incorporating buffering apatite into the composite particles, a portion of the acidity was neutralized by the presence of bare apatite instead of by apatite-protein complexes. As a result, less protein was released.

Loading of the same mass of CAP-BSA differing in BSA content into composite particles constructed of 24 kD PLGA was used to determine whether protein release was affected. Apatite-BSA complexes were prepared by adsorbing 9 and 20 w/w % of FITC-BSA onto CAP. The resulting complexes were incorporated into composite particles (labeled "9 w/w %" and "20 w/w %" in FIG. 12A) such that each set of particles contained the same mass of CAP-BSA and approximately the same mass of apatite, but the BSA content of the "20 w/w %" particles was twice that of the "9 w/w %" particles. As the protein loading on apatite was increased, the amount released was higher, as expected. However, the release profile of the "20 w/w %" particles was steeper at the start and then leveled off, which deviated from the typical release profile of composite particles constructed with 24 kD PLGA, where the upturn occurred at ~21 days. This higher initial burst might be indicative of protein adsorption in multilayers instead of in a monolayer on CAP. By applying the Langmuir adsorption isotherm to the protein adsorption results, it was estimated that a protein loading of approximately 28 w/w % would constitute monolayer coverage on CAP if all the surface area were available for protein adsorption. However, a portion of the CAP surface area was occluded due to pores that were smaller than the size of BSA. Hence, a protein loading of 20 w/w % could have exceeded monolayer coverage. Proteins that were adsorbed in multilayers would be released more quickly and in larger quantity upon dissolution of the underlying apatite.

Different amounts of CAP-BSA with the same BSA content (9 w/w %) were loaded into composite particles constructed of 24 kD PLGA. Increasing the CAP-BSA loading diminished the amount of BSA released (FIG. 12B). This result is contrary to that of polymeric particles prepared by W/O/W emulsification, for which raising the protein loading often leads to faster and increased protein release. A possible explanation is as follows. The dissolution of apatite in the apatite-BSA complex released protein but also left behind bare apatite. In addition, acid molecules ($H_3O^+$, lactic acid, glycolic acid, or short uncapped PLGA segments) that are smaller than BSA might be able to access bare apatite surfaces that the protein was unable to reach. This bare apatite has buffering capacity, as discussed hereinabove. Therefore, as the apatite-BSA complex loading was raised, the presence of such bare apatite was also increased, leading to a reduction in protein release.

Decreased CAP-BSA loading in composite particles produces rapid depletion of the protein complex by acid evolution from PLGA such that at later time points, even with the continual degradation of PLGA, there is no further protein release. To determine whether if the proportion of CAP-BSA is increased, some of the complex might remain after complete PLGA degradation, the percent cumulative release from such particles was plotted, and the results indicate a low release (FIG. 12C). Therefore, complex loading can be adjusted so that for a precious therapeutic protein, a high percentage of the protein is released before polymer degradation is complete.

Comparison with Protein Release from Polymeric Microspheres Prepared by Double Emulsion Method The release profiles of polymeric microspheres that were prepared by the double emulsion method (FIG. 12D)

showed protein release beginning with an initial burst, sometimes as high as 55%. This initial burst may be due to the solubilization of protein that is loosely adsorbed on the surface or in the pores of the particles. Protein release then approached a plateau, where protein that is physically entrapped may diffuse through tortuous channels in the particles and emerge slowly. In later stages, an upturn in the release profile may have occurred due to the degradation of the polymer, releasing protein that was bound to the polymer. Hence, the early stages of protein release are diffusion-controlled, and the later stages are degradation-controlled. The release profiles obtained were for 4 weeks and did not reach the degradation-controlled phase. The profiles show that the addition of a more hydrophobic polymer, PLA, reduced the initial burst. However, the release rate was remarkably similar for both sets of particles despite their difference in polymer composition.

Degradation of Polymeric Phase of Composite Microparticles

Acid release from blank PLGA-CAP composite particles was estimated by tracking the molecular weight of the remaining polymer by GPC, and converting the mass lost into the amount of acid released (FIG. 12E). The conversion was performed using the approximation that a two-fold reduction in molecular weight, which suggests the breakage of a polymer chain into two, results in the release of one acid molecule.

PLGA of low molecular weight, namely 6 kD and 13 kD, degraded rapidly, as indicated by the steepness of the slope in the figure. Longer chained polymers degraded more gradually, giving rise to a more constant rate of acid production. The increase in slope at later time points for both low and high molecular weight polymers may be due to an autocatalytic effect: ester hydrolysis is catalyzed by acid or base, and hence, the accumulation of acidic degradation products in the particles can accelerate the rate of hydrolysis Example 5

Composite Microparticles Containing rhBMP-2 Induce Mesenchymal Stem Cell Differentiation Along the Osteoblast Lineage Materials And Experimental Methods Preparation of RhBMP-2-Loaded Composite Microparticles Recombinant human BMP-2 (rhBMP-2) was obtained from R&D Systems. Composite microparticles encapsulating rhBMP-2 were synthesized under aseptic conditions by a solid-in-oil-in-water (S/O/W) emulsion process [Yong, T. Het al., Proceedings of the 2004 Singapore-MIT Alliance Symposium (MEBCS) 2004]. A typical synthesis involved dissolving 250 mg of PLGA (Alkermes) in 2 ml of dichloromethane. The polymer solution was sterile filtered through a 0.45-μm Teflon membrane into a vial containing carbonated apatite pre-adsorbed. with rhBMP-2. The mixture was vortexed to create a solid-in-oil suspension, which was then transferred to 50 ml of 0.1 w/v % methyl cellulose solution that had been autoclaved. An S/O/W suspension was formed by homogenizing at 8000 rpm for 2 min at room temperature. To solidify the composite particles, dichloromethane was evaporated by heating the suspension at 30° C. for 3 h. The particles were collected by centrifugation, washed with sterile water, and freeze-dried.

Helistat sponges (Integra Life Sciences) were trimmed to pieces of approximately 7 mg in mass. Each piece of sponge was loaded with 1.4 μg of BMP-2 in phosphate buffered saline. Sponges soaked up the protein for 15 minutes, and were then transferred to 2 ml of Basal Medium Eagle (BME) in sterile tubes and incubated at 37° C. At pre-determined time intervals (1, 4, 7, 10, 14, 18 days, etc.), medium in the tubes was removed without disturbing or drying out the sponge, and replaced with an equivalent volume of fresh medium.

Evaluation of in Vitro Release

Release studies were conducted in Eagle's basal medium (BME; Sigma) supplemented with 10 v/v % heat-inactivated fetal bovine serum (Invitrogen) and 1 v/v % antibiotics (100 IU/ml penicillin and 100 μg/ml streptomycin; ATCC, referred to as 'complete BME'. RhBMP-2-loaded composite particles were suspended at a concentration of 20 mg/ml in complete BME and incubated at 37° C. At pre-determined time intervals (1, 4, 7, 10, 14, 18, 22, 26, 30 days, up to 100 days), the samples were centrifuged, and the supernatant was withdrawn completely and replaced with an appropriate volume of fresh medium. The collected supernatant was filtered and stored at −20° C. until evaluation by a BMP-2 sandwich enzyme-linked immunosorbent assay (ELISA) kit (R&D Systems). The assay consisted of adding 50 μl of standards and test samples to a 96-well plate coated with anti-BMP-2 monoclonal antibody. The plate was incubated at room temperature for 2 h and washed. Biotinylated anti-BMP-2 antibody was then added, and the plate was further incubated for 2 h. Unbound antibody was removed by washing, following which streptavidin-horse radish peroxidase was introduced. After 30 min, color was developed by the addition of hydrogen peroxide and tetramethylbenzidine. Absorbance was read at 450 nm using a UV-Vis microplate reader (VersaMax, Molecular Devices) with wavelength correction at 570 nm. The concentration of the protein released at each time point was used to construct cumulative release profiles.

Collected supernatants of particle samples, and medium from the sponge cultures was also used to culture C3H10T1/2 cells for 4 days in 24-well plates (cell density of 6000/cm$^2$, medium volume of 0.42 ml). After 4 days, cells were lysed with a solution of Triton X-100. Alkaline phosphatase activity in cell lysates was determined using p-nitrophenylphosphate (p-npp) as the substrate. The amount of p-npp converted to p-nitrophenol per unit time was measured with a UV-vis microplate reader at 405 nm and 37° C. Enzyme activity was normalized to the total intracellular protein concentration present in the lysate and expressed as nmol of p-nitrophenol formed per minute per mg protein. (adapted from Lowry et al., 1954, J Biol. Chem., 207: 19–37.) Using Beer's Law and an extinction coefficient of 18.45 cm·L/mmol for p-nitrophenol, the amount (in nmol) of p-nitrophenol formed per minute was determined. ALP activity was normalized by the protein concentration of the lysate as determined by total protein assay (Pierce) and expressed as nmol/min·mg protein. ALP activity induced by the medium collected at each time point was plotted as a function of time. Data were plotted as mean±standard deviation. Statistical analysis was performed using Student's t-test. A significance level of p<0.05 was used.

Effect of Prolonged Exposure to Release Medium

Based on results from in vitro release-and induced ALP activity at each time point, a set of composite microparticles with a sustained release profile of bioactive rhBMP-2 was chosen. This set of composite particles was constructed of 59 kD PLGA and 0.08 mg of carbonated apatite per mg of PLGA. rhBMP-2 loading in the particles was 145 ng per mg carrier. The effect of prolonged exposure of C3H10T1/2 cells to release medium from this set of particles was studied. As before, the composite microparticles were incubated at 37° C. in complete BME at a concentration of 20 mg/ml. C3H10T1/2 cells were seeded in 24-well plates at a density of 6000 cells/cm$^2$. Twice per week, the medium in the wells was aspirated and replaced with 0.5 ml of filtered release medium collected from the particles. Release medium from blank composite particles served as controls. For comparison, complete BME systems enriched with fixed concentrations of rhBMP-2 (10 and 100 ng/ml; 0.5 ml per well) were used. Cell culture was conducted for 8 weeks in all groups.

At 1, 2, 3, 4, 6 and 8 weeks, cells in 4 wells for each group were lysed, and the ALP activity of the cell lysate was measured. At each week, the osteocalcin level of the conditioned medium of 4 wells in each group was assayed by sandwich ELISA (Biomedical Technologies, Inc.). The procedure for this ELISA was similar to that of the BMP-2 assay. Statistical analyses of ALP and osteocalcin levels were performed using Student's t-test. A significance level of $p<0.05$ was used.

Results

Alkaline phosphatase (ALP) is a marker of the osteoblast phenotype. A pluripotent embryonic mouse mesenchymal stem cell (MSC) line, C3H10 T1/2 can be induced to differentiate into osteoblasts by the administration of rhBMP-2 (FIG. 13A). The induction of ALP activity by rhBMP-2 is dose-dependent.

The induction of ALP activity in C3H10T1/2 cells by different concentrations of rhBMP-2 over 4 days was examined. Increasing the concentration of rhBMP-2 from 0 ng/well to 200 ng/well (400 ng/ml) was found to elevate ALP activity (FIG. 13B). At rhBMP-2 concentrations beyond 200 ng/well, the effect reached saturation. Thus, there appeared to be an optimum dosage of rhBMP-2 for evoking ALP expression, which was related to the commitment of undifferentiated cells to the osteoblast lineage.

Incubation of the MSC with medium collected from sCAP or CAP composite microparticles containing rhBMP-2 provided enhanced ALP production (FIGS. 13C & D, respectively). Significantly lower concentrations of rhBMP-2 were required for comparable ALP production in the cells, and ALP production was sustained over a 28-day period of time. Bioactive protein release is sustained over a long period of time, in that medium collected at these time points induces ALP activity.

Levels of ALP activity induced by release media collected from rhBMP-2-loaded composite microparticles are plotted in FIG. 14. Release media collected over a period of 100 days induced elevated ALP expression in C3H10T1/2 cells. These results indicated that released rhBMP-2 retained at least part of its biological activity and that the release of bioactive rhBMP-2 over extended periods of time was possible, conceivably for even longer periods of time, since the cumulative release and bioactivity of rhBMP-2 appeared to be experiencing an upturn at 100 days (FIG. 14A).

When a higher apatite loading was used in the composite microparticles, rhBMP-2 release was dampened, and the capacity for ALP induction declined within the first week (FIG. 14B). In contrast, when rhBMP-2 release was augmented and prolonged by using a 3:2 blend of PLGA and PLA in the composite microparticles, ALP expression was significantly elevated throughout the course of the study (FIG. 14C).

Moreover, comparison of rhBMP-2 containing-composite microparticles versus BMP-2 loaded Helistat Collagen sponges demonstrated that ALP activity is much greater in the microparticles (FIG. 15A). Despite comparable BMP-2 loading in composite microparticles comprising higher molecular weight PLGA, greater BMP-2 was released, in comparison to composite microparticles comprising PLGA of smaller molecular weight (compare with FIG. 15A with 13C). Thus composite microparticles comprising BMP-2 provide for enhanced ALP production, hence MSC differentiation, as compared to supply of the recombinant protein alone, or that encased in a collagen sponge.

The induction of ALP activity was not a simple function of the amount of rhBMP-2 released, however. As depicted in FIGS. 15B and C, rhBMP-2 release from Helistat® sponges was of greater magnitude than that from composite microparticles shown in FIG. 13. Nevertheless, the level of ALP expression was lower, and tapered off after 2 weeks, despite the continued release of rhBMP-2. It is unclear what caused the lowered bioactivity of rhBMP-2 released from these sponges, a finding consistent in the two experiments thus conducted.

Compared against controls with no exposure to rhBMP-2, prolonged exposure of C3H10T1/2 cells to the growth factor resulted in elevated levels of ALP expression (FIG. 16A). However, the increase was not monotonic; ALP activity reached a maximum at ~2 weeks and then dropped to levels that were maintained over the remainder of the experiment. A dose-dependent response to rhBMP-2 was found, where 50 ng of rhBMP-2 per well induced higher levels of ALP activity than 5 ng/well.

The culture of C3H10T1/2 cells with release medium collected from rhBMP-2-loaded composite microparticles produced a similar effect. ALP activity was considerably raised in the first 2 weeks, and then slowly declined to levels comparable to the controls at the end of 8 weeks (FIG. 16B).

Osteocalcin is a later stage marker of osteoblast differentiation associated with matrix maturation and mineralization. rhBMP-2 was found to upregulate osteocalcin expression in C3H10T1/2 cells in a time- and dose-dependent manner (FIG. 16C). Control cells with no exposure to rhBMP-2 showed low osteocalcin levels, particularly at the start of the experiment. 5 ng of rhBMP-2 per well produced a weak response, which became statistically insignificant ($p>0.05$) at 7 weeks. A more robust response was obtained with 50 ng of rhBMP-2 per well. Osteocalcin levels experienced doubling in the first 3 weeks, held steady for the next 4 weeks, and then peaked again at week 8.

Release medium collected from rhBMP-2-loaded composite microparticles had a remarkable effect on osteocalcin upregulation. Osteocalcin levels increased steadily with time over 4 weeks, then showed an exponential rise from weeks 4 to 7 (FIG. 16D). The level reached at week 7 was 10-fold that of the response to rhBMP-2-enriched BME (50 ng/well). These results suggested that the cells were undergoing a significant amount of mineralization activity, indicative of an osteoblast phenotype.

Example 7

Composites Prepared as Porous Bulk Scaffolds

Materials and Experimental Methods

A precipitation process was devised to prepare composite bulk scaffolds. A typical synthesis involved adding 20 mg of a protein-apatite complex to 250 mg of PLGA in 2 ml of dichloromethane. The mixture was vortexed to form a homogeneous solid-in-oil suspension. The suspension was then added drop-wise to ethanol. Diffusion of dichloromethane into the surrounding ethanol resulted in the precipitation of PLGA, which is insoluble in ethanol. The PLGA-apatite precipitate was dried under vacuum to remove the remaining solvent. Solvent removal led to the creation of pores in the PLGA-apatite composite.

Results

Two types of bulk composite scaffolds were prepared that differed in their method of protein loading: 1) Scaffolds fabricated from a physical mixture of solid protein and solid apatite dispersed in PLGA solution, labeled "pmix"; and 2) Scaffolds prepared from apatite-BSA complexes in which the protein was pre-adsorbed onto the apatite, labeled CAP-cplx and HAP-cplx (FIG. 15). Protein release from CAP-cplx and HAP-cplx samples was approximately 10 times slower than that from the CAP-pmix and HAP-pmix scaffold, and more sustained, indicating that the apatite-protein complex is very stable, that apatite has a high affinity for the protein, which prevents its leaching from the scaffold.

Protein release from composite scaffolds is influenced by additional factors not as pivotal to release from composite particles. Some of these factors include porosity, pore size, and dimensions of the scaffold. The lower surface/volume ratio of these scaffolds compared to composite particles translates into longer diffusion lengths, slower water penetration and polymer degradation, and more sustained protein release. Increasing the porosity or reducing the dimensions leads to faster water entry. Therefore, the morphology and size of the composite delivery vehicle are important determinants of protein release.

Visualization of CAP power alone, or samples following the adsorption of BSA onto CAP visualized by SEM, provided a relatively amorphous aggregate (FIG. 17A and B, respectively). PLGA-HAP-BSA scaffolding, however, produced a more organized porous material (FIG. 17C).

Example 8

Various Methods May be Employed to Produce Composite Controlled Release Particles A solution of a biodegradable polymer yielding acidic degradation products, is prepared in a water-miscible, organic solvent, such as acetone or ethyl acetate. A basic, inorganic material, such as apatite with an adsorbed water-soluble compound of interest, for example a protein such as BMP-2, is dispersed in the polymer solution, the solution may be vortexed, to yield a solid-in-oil suspension.

The solid-in-oil suspension is added dropwise with a needle of fine gauge into an aqueous medium. The organic solvent diffuses into the aqueous phase, leading to precipitation of the polymer and the formation of particles. The suspension is stirred magnetically until all the organic solvent has evaporated. Particles are then collected by centrifugation or filtration.

A modification of the above protocol may involve the use of organic solvents with poor water miscibility, such as dichloromethane and chloroform, to dissolve the polymer. In such cases, the precipitating medium could be, or example, ethanol or hexane, or any medium that is a non-solvent for the polymer and the apatite-protein complex, but is miscible with the organic solvent used to dissolve the polymer.

Another method employs the use of a solution of the biodegradable polymer prepared in an organic solvent, such as dichloromethane, chloroform, acetone or ethyl acetate, which is used to disperse the water-soluble compound adsorbed onto a basic inorganic material, yielding a solid-in-oil suspension. The solid-in-oil suspension is atomized in a spray dryer, and the organic solvent is removed by hot nitrogen or other inert gases to precipitate the polymer around the apatite-protein complex, leading to the formation of particles.

Example 9

Other Forms for the Composites

Materials and Experimental Methods

The apatite-protein complex was prepared as described hereinabove. The apatitic phase used was carbonated apatite (CAP), and the protein used was FITC-BSA. A solution of PLGA was prepared by dissolving 250 mg of 59 kD PLGA in 2 ml of acetone. To this solution, 20 mg of the CAP-BSA complex was added. The suspension was vortexed, and then added dropwise to round glass coverslips. Acetone was allowed to evaporate at room temperature, resulting in the formation of thin composite films.

Protein release was assessed from the resulting films. Three films were carefully detached from the coverslips, and three films were left on their glass substrates. The films were transferred to individual wells of a 24-well plate, and 1.5 mL of BES buffer (pH 7.4) was added to each well. The plate was incubated at 37° C. At 1, 4, 7, 14, 21, and 28 days, 0.75 ml of the release medium was withdrawn and replaced with 0.75 ml of fresh buffer. The FITC-BSA concentration in the release media was determined with the Coomassie Plus total protein assay (Pierce) and used to construct cumulative release profiles.

Results

Free-floating films, which had been detached from their glass substrates, swelled considerably and became porous over the course of the release study. The films that were not detached from the glass coverslips remained well-adhered and showed less swelling. The protein release profiles of the two types of films were similar, as shown in FIG. 19. The gradual rise in the release profiles suggests that such films could be useful in the sustained release of therapeutic agents. Hence, this experiment demonstrates the feasibility of forming apatite-polymer composites into drug-releasing thin films. Such films may be useful as coatings on medical implants.

Example 10

Other Methods for Obtaining Composite Particles

Materials and Methods

Microprecipitation

Protein-loaded composite microparticles were typically prepared by a solid-in-oil-in-water (S/O/W) emulsion in which the solid-in-oil phase is homogenized in an aqueous surfactant solution to create the composite micro-droplets. (Solid phase=apatite-protein complex, oil phase=polymer dissolved in organic solvent.) No surfactant addition or homogenization was carried out. Various chemicals were assessed for use as the oil and aqueous phases, in order to achieve the appropriate interfacial interactions between phases such that the oil phase would form spheres in the aqueous phase with high dispersion. Dichloromethane, acetonitrile, and acetone in various proportions were assessed as the possible oil phase, while aqueous solutions were examined with varying compositions of ethanol and isopropanol.

The encapsulation was performed as follows: PLGA was dissolved in the oil phase at a concentration of 125 mg/ml. A solid-in-oil suspension was formed by adding 20 mg of the apatite-protein complex. This suspension was then added dropwise to the aqueous phase under magnetic stirring at ~300–400 rpm. After heating at 30° C. for 3 hours to drive off the organic solvent, the particles were collected through centrifugation and freeze-drying.

| Oil Phase | Aqueous Phase | Results |
| --- | --- | --- |
| 12.5% acetone, 87.5% dichloromethane | 5% ethanol in water | Flakes of polymer, apatite, and protein. |
| Dichloromethane | 5% ethanol in water | Clumping at the surface, poor yield of spherical polydisperse particles. |
| Acetonitrile | Water | Irregular particles. |
| 50% dichloromethane, 50% acetonitrile | Water | Irregular particles. |
| 2.5% dichloromethane, 97.5% acetone | 5% ethanol in water | Irregular particles. |
| 20% dichloromethane, 80% acetone | 5% ethanol in water | Good yield of non-spherical, polydisperse particles. |

Results

The results of the microprecipitation experiments are summarized in Table 10.1. The morphology of the particles was not as regular (spherical) as that obtained by S/O/W emulsion with homogenization. It should be noted that the release mechanism of the apatite-polymer composites does not require a spherical morphology, although the size and shape of the particles can influence the rate of water penetration and polymer hydrolysis, and the rate of diffusion of the therapeutic agent out of the composites.

Table 10.1 Microprecipitation Results

The microprecipitation process set forth herein is to serve as an example of such methods of obtaining composite particles of the invention.

Example 11

Preparation of Composite Gelatin Scaffolds

Apatite-PLGA composite microparticles loaded with either BSA (model protein) or rhBMP-2 (therapeutic protein) were prepared under aseptic conditions as described hereinabove. Cell culture grade gelatin powder (Type A, 300 Bloom; Sigma) was added to sterile water to form a 10 w/v % solution. The gelatin solution was sterilized by autoclaving. To 5 ml of the gelatin solution, 200 mg of protein-loaded apatite-PLGA composite particles was added, constituting a particle loading of 28.6 w/w %. The mixture was vortexed briefly and 0.5 ml was transferred to each chamber (8 total, area =0.7 cm$^2$) on a chamber slide (Lab-Tek™ II, Nunc).

The gelatin mixture was crosslinked with either glutaraldehyde or N-Ethyl-N'-(3-dimethylaminopropyl)carbodiimide hydrochloride (EDAC; Sigma) and N-hydroxysuccinimide (NHS; Sigma). Glutaraldehyde bridges the amino groups on gelatin to form an imine linkage whereas EDAC/NHS catalyzes the reaction between a carboxyl group and an amino group to form an amide linkage. In the case of crosslinking by glutaraldehyde, 20 μl of a 25 w/v % glutaraldehyde solution in water was added to the gelatin solution, resulting in a glutaraldehyde concentration of 10 w/w % of the gelatin. The gel was left to set at room temperature for 3 hours. The composite gels thus formed were removed from the chamber slide and washed 3 times with 5 w/w % glycine in water. The function of glycine was to cap any unreacted glutaraldehyde, which is highly cytotoxic. The glycine washes were followed by 3 water washes. All washes were at 37° C. and were at least 1 hour in length. Crosslinking by EDAC/NHS was conducted by adding 50 μl of 0.70 mM NHS and 50 μl of 0.98 mM EDAC to 0.5 ml of the gelatin suspension in the chamber. Crosslinking was allowed to proceed at room temperature for 2 hours, after which the composite gels were rinsed 3 times with water to remove unreacted EDAC/NHS and urea, which was the non-toxic side product.

The composite gels were frozen in a −20° C freezer overnight and then freeze-dried for 2 days.

Results

For dual release of proteins from these composite gels, co-encapsulation of two sets of protein-loaded composite particles was performed. For example, fluorescein isothiocyanate (FITC)-BSA-loaded composite particles and tetramethyl rhodamine isothiocyanate (TRITC)-BSA-loaded composite particles were dispersed in the same proportion in gelatin before crosslinking. The FITC-BSA-loaded particles were constructed of 6 kD PLGA and sCAP (carbonated apatite 1-μm in size) and had a faster release profile than the TRITC-BSA-loaded particles constructed of 59 kD PLGA and sCAP.

Two sets of composite particles were prepared, each with different release kinetics. One set encapsulating FITC-BSA was fabricated from 6 kD PLGA and sCAP, and had a fast release profile. The other set encapsulating TRITC-BSA was prepared from 59 kD PLGA and sCAP, and exhibited slower release. The two sets of composite particles were dispersed in separate gelatin scaffolds ('solo gels') as well as combined in equi-proportions in a single gelatin scaffold ('mixed gel'). The release profiles of BSA from the composite particles, 'solo gels', and 'mixed gels' are shown in FIG. 20.

Entrapment of the composite particles in a gelatin scaffold led to protein release of lower magnitude. The gel was an additional diffusion barrier to the proteins, and served to smoothen out release, particularly for the set of composite particles encapsulating FITC-BSA that showed a large initial burst in the absence of the gelatin matrix. The co-entrapment of two sets of composite particles in a single gelatin scaffold demonstrated the feasibility of dual protein release. FITC-BSA and TRITC-BSA were released from the 'mixed gel' with distinct release profiles. Whether the particles were combined in a 'mixed gel' or kept separate in 'solo gels' made little difference to the release profiles. Each set of composite particles functioned essentially on its own in gelatin. Hence, the aggregate protein release profile of a gelatin scaffold is the sum of its parts, which facilitates the design and testing of multifactor release.

Example 12

Calcium Release from Composite Microparticles

Subsequent to polymer degradation and the release of acid, apatite that is embedded in the polymer matrix dissolves to produce calcium and phosphate ions. The release of calcium ions was detected with a calcium-sensitive fluorophore (Rhod-5N). A caveat to the use of this fluorophore is its sensitivity to the pH and salt concentration of the medium. Hence, even with a calibration curve, the results obtained were only estimates of the actual calcium concentration. Nevertheless, the fluorophore was useful in confirming the presence of calcium and the change in its concentration with time. The results for two sets of blank PLGA-CAP microparticles differing in molecular weight of the polymeric phase (13 kD and 59 kD PLGA) are shown in FIG. 21. Comparisons are made with a set of PLGA-CAP-BSA microparticles (59 kD PLGA) and with bare CAP.

For particles prepared with 59 kD PLGA, the release of calcium was gradual and bore similarity to the acid release profile (FIG. 12E) and the protein release profile (FIG. 12D). The presence of BSA on CAP did not appear to affect its dissolution. However, it is unclear if the increase in magnitude of calcium release was the result of a real enhancement due to BSA or a change in fluorescence of Rhod-5N in the presence of BSA.

In the case of the particles containing 13 kD PLGA, the sharp rise in the calcium release profile within the first 7 days also resembled the protein release profile, as did the subsequent plateau. However, although acid continued to be released past 7 days, there appeared to be little calcium or protein release. Another unusual observation was the fall in the cumulative calcium release profile after 7 days, which suggested that calcium was re-precipitated out of the release medium, possibly due to interactions with the anionic groups on the polymer or due to pH shifts. In general, the calcium indicator was able to confirm enhanced release of calcium from the composite microparticles over the passive leaching of calcium ions from CAP alone.

Comparisons amongst the acid, calcium, and protein release profiles of the composite particles confirm that as the polymer degraded, apatite was dissolved and led to the release of protein.

Example 13

In Vivo Composite Efficacy in a Rat Ectopic Model

Materials and Experimental Methods

Two groups of BMP-loaded collagen scaffolds were tested. The dimensions of the Helistat® collagen sponges used were ~6.3 mm×4.2 mm×12.7 mm, weighing ~2.3 mg. The first group comprised sponges injected with ~2.4 mg of rhBMP-2-loaded composite microparticles as described hereinabove; the total amount of rhBMP-2 in the scaffold was ~3 µg. The second group was a positive reference, prepared by soaking the collagen sponges with 3 µg of rhBMP-2 for 15–20 min. Controls were either blank Helistat® sponges (no composite particles) or sponges containing ~2.4 mg of blank composite microparticles.

Animal studies were conducted in accordance with the institute guidelines for the care and use of animals. Male Wistar rats of 7–8 weeks old were anesthetized with an intraperitoneal injection of sodium pentobarbital (~50 mg/kg) before each procedure. The back of each rat was wiped with iodine and 70% ethanol solution. Four incisions, each ~1 cm long, were made on each side of the rat lateral to the spine along the dorsum. On one side of the rat, four sponges of the same group were inserted into subcutaneous pouches while the other side received the appropriate control (either blank sponge or sponge with blank particles).

Each experimental group comprised 6 rats. After surgery, food was given ad libitum. No adverse clinical reactions were observed and all surgical incisions healed without infection.

At time points of 1, 2 and 4 weeks, 2 rats from each group were anesthetized and subjected to radiography. The rats were sacrificed and the collagen scaffolds were removed and fixed in 10% formaldehyde solution. The specimens were dehydrated, embedded in paraffin, sectioned, and stained with hematoxylin and eosin (H&E). Histological sections were examined under a light microscope (Leica).

Based on results from radiography and histology, a second experiment was conducted to determine the minimum dosage of rhBMP-2 and rhBMP-6 required, to induce ectopic bone formation. To increase the persistence time of the collagen sponges in vivo, the extent of crosslinking of the sponges was increased by soaking them in 10 ml of a solution of 0.35 mM EDAC and 0.49 mM NHS for 1 hour, following which the sponges were washed with sterile water and freeze-dried. RhBMP-2 and rhBMP-6 were tested independently at dosages of 2, 5, 10, 20, and 50 µg per sponge. Intramuscular sites, which are more vascularized and may be more responsive than subcutaneous sites, were tested. Each BMP-containing sponge was implanted in one quadriceps of a rat while the other quadriceps received a control. For each dosage, two rats were tested. At 2, 4, 6, and 8 weeks, the rats were anesthetized and x-rayed to evaluate the development, if any, of a radiopaque area indicative of bone formation.

Results

At 1 and 2 weeks, collagen scaffolds were excised from the rats. Scaffolds containing rhBMP-2, either encapsulated within composite particles or directly loaded onto the sponge, were fully resorbed at 4 weeks. Only remnants of the controls—blank composite collagen sponges and blank collagen sponges—could be found at 4 weeks. The explants were stained with hematoxylin and eosin (H&E) (FIGS. 22 and 23). In the histological sections, nuclei appeared blue/blue-black, cytoplasm appeared pink, red blood cells were red, and the collagen scaffold was stained brown (Mayer's hematoxylin) or blue (Harris' hematoxylin).

The presence of rhBMP-2 in the sponges in both groups led to greater cellularity and vascularization, evident one-week post implantation. The density of nuclei, lower proportion of scaffold remnants, etc., indicated greater tissue ingrowth. Angiogenesis was evident as well. Control scaffolds did not appreciably demonstrate tissue ingrowth or population of the scaffold.

Both forms of BMP-2 loaded scaffolds showed tissue ingrowth and vascularization, however microparticle containing sponges revealed greater cellularity than sponges comprising the recombinant protein alone.

What is claimed is:
1. A controlled release composite comprising:
   a basic inorganic material;
   a water-soluble compound adsorbed to said basic inorganic material; and
   a bio-degradable polymer which yields acidic degradation products whereby acidic degradation products from said polymer facilitate dissolution of said basic inorganic material and release of said adsorbed compound.

2. The controlled release composite of claim 1, wherein said water-soluble compound is a peptide, a protein, a nucleic acid or a drug.

3. The controlled release composite of claim 1, wherein said basic inorganic material is hydroxyapatite, carbonated apatite, calcium phosphate, calcium carbonate, zinc oxide, magnesium oxide, or alumina.

4. The controlled release composite of claim 1, wherein said bio-degradable polymer is a poly($\alpha$-hydroxyacid), such as poly(lactic acid), poly(glycolic acid), or blends thereof, a poly(orthoester), poly(anhydride), or a poly(hydroxyl alkanoate).

5. The controlled release composite of claim 1, wherein dissolution of said basic inorganic material releases charged species over a course of time.

6. The controlled release composite of claim 5, wherein said charged species comprises calcium or phosphate, or a combination thereof.

7. The controlled release composite of claim 1, wherein said system may be in the form of a particle.

8. The controlled release composite of claim 1, wherein said composite is in the form of a gel, bulk scaffold, thin film or pellet.

9. The controlled release composite of claim 1, further comprising an amphoteric species, which alters the rate of dissolution of said basic inorganic material, liberation of said adsorbed compound, or a combination thereof.

10. The controlled release composite of claim 9, wherein said amphoteric species serves as a diffusion barrier to the liberated compound.

11. The controlled release composite of claim 10, wherein said amphoteric species is a gelatin.

12. The controlled release composite of claim 1, wherein said biodegradable polymer comprises a blend of at least 2 polymers, which differ in their hydrophobicity.

13. The controlled release composite of claim 12, wherein varying the concentration of said at least 2 polymers affects the release rate of said water-soluble compound.

14. The controlled release composite of claim 1, further comprising unadsorbed basic inorganic material.

15. A process for preparing a composite scaffolding comprising a water-soluble compound, comprising the steps of:
(a) adsorbing a water-soluble compound onto a basic, inorganic material;
(b) combining the product in (a) with a solution of a biodegradable polymer which yields acidic degradation products to form a solid-in oil emulsion;
(c) precipitating the composite scaffolding product in (b); and
(d) isolating said composite scaffolding.

16. The process of claim 15, wherein said water-soluble compound is a peptide, a protein, a nucleic acid or a drug.

17. The process of claim 15, wherein said basic inorganic material is hydroxyapatite or carbonated apatite.

18. The process of claim 15, wherein said bio-degradable polymer is polylactide-co-glycolide.

19. The process of claim 15, wherein isolation of said composite scaffolding comprises drying or lyophilization.

20. The process of claim 15, wherein said polymer solution concentration, molecular weight of said polymer, or a combination thereof, may be varied.

21. The process of claim 20, wherein varying said polymer solution concentration, molecular weight of said polymer, or a combination thereof, produces composite microparticles differing in size.

22. The process of claim 15, wherein said polymer comprises a blend of at least 2 polymers, which differ in their hydrophobicity.

23. The process of claim 22, wherein said blend of at least 2 polymers may be varied in terms of their concentration.

24. The process of claim 23, wherein varying the concentration of said at least 2 polymers affects polymer degradation rate in said scaffolding.

25. The process of claim 15, wherein free apatite is added in step (b).

26. The process of claim 15, wherein the percent water-soluble compound adsorbed onto said basic, inorganic material is varied.

27. The process of claim 26, wherein varying said percent water-soluble compound adsorbed onto said basic, inorganic material affects the release kinetics of said water-soluble compound from said composite scaffolding.

28. The process of claim 15, further comprising the step of combining said composite microparticles with a solution of gelatin, chitosan, arabinogalactan, collagen, alginate, hyaluronic acid, fibrin, or cellulose.

29. The process of claim 28, further comprising the step of adding a cross-linker.

30. The process of claim 29, wherein said cross-linker is glutaraldehyde.

31. A porous scaffolding prepared by the process of claim 15.

32. A method of controlled delivery of a therapeutic water-soluble compound to a subject, comprising administering to said subject a controlled release composite comprising a therapeutic water-soluble compound adsorbed onto a basic, inorganic material and a bio-degradable polymer which yields acidic degradation products, whereby degradation of said polymer yields acidic degradation products therefrom, which stimulates dissolution of the inorganic material and release of said therapeutic water-soluble compound over a period of time, thereby being a method of controlled delivery of a therapeutic water-soluble compound.

33. The method of claim 32, wherein said therapeutic compound is a peptide, a protein, a nucleic acid or a drug.

34. The method of claim 32, wherein said therapeutic compound is osteogenic, chondrogenic or angiogenic.

35. The method of claim 32, wherein said therapeutic compound is an antibacterial, antiviral, antifungal or antiparasitic compound.

36. The method of claim 32, wherein said therapeutic compound is immunostimulatory.

37. The method of claim 32, wherein said therapeutic compound inhibits inflammatory or immune responses.

38. The method of claim 32, wherein said basic inorganic material is hydroxyapatite, carbonated apatite, calcium phosphate, calcium carbonate, zinc oxide, magnesium oxide, or alumina.

39. The method of claim 32, wherein said bio-degradable polymer is a poly($\alpha$-hydroxyacid), such as poly(lactic acid), poly(glycolic acid), or blends thereof, a poly(orthoester), poly(anhydride), or a poly(hydroxy alkanoate).

40. The method of claim 32, wherein dissolution of said basic inorganic material releases charged species over a course of time.

41. The method of claim 32, wherein said charged species comprises calcium or phosphate, or a combination thereof.

42. The method of claim 32, wherein said composite is in the form of a gel, bulk scaffold, thin film or pellet.

43. The method of claim 32, wherein said composite controlled release system further comprises an amphoteric species, which alters the rate of dissolution of said basic inorganic material, liberation of said adsorbed compound, or a combination thereof.

44. The method of claim 42, wherein said amphoteric species serves as a diffusion barrier to the liberated compound.

45. The method of claim 42, wherein said amphoteric species is a gelatin.

46. The method of claim 32, wherein said controlled release composite comprises a biodegradable polymer whose concentration, molecular weight, or combination thereof, is varied.

47. The method of claim 45, wherein varying said biodegradable polymer concentration, molecular weight, or combination thereof, affects the release rate of said water-soluble compound.

48. The method of claim 32, wherein said biodegradable polymer comprises a blend of at least 2 polymers, which differ in their hydrophobicity.

49. A method of tissue engineering comprising the step of contacting a cell with a composite scaffolding comprising a water-soluble tissue-promoting factor adsorbed onto a basic, inorganic material and a bio-degradable polymer which yields acidic degradation products, whereby degradation of said polymer yields acidic degradation products therefrom, which stimulates dissolution of said inorganic material and release of said water-soluble tissue-promoting factor, and whereby said cell responds to said tissue-promoting factor, promoting tissue formation, thereby providing a method of tissue engineering.

50. The method of claim 49, wherein said tissue is bone or cartilage.

51. The method of claim 49, wherein said tissue-promoting factor is a bone morphogenetic protein, a member of the TGF-β superfamily, or a member of the BMP signaling cascade.

52. A method of stimulating or enhancing bone repair, or maintaining or increasing bone volume, bone quality, or bone strength in the body of a subject in need, comprising the steps of: contacting a cell in said subject with a composite controlled release system comprising a water-soluble factor adsorbed onto a basic, inorganic material and a bio-degradable polymer which yields acidic degradation products, whereby degradation of said polymer yields acidic degradation products therefrom, which stimulates dissolution of said inorganic material and release of said water-soluble factor, and whereby said cell responds to said factor, promoting bone repair, increased bone volume, bone quality, or bone strength, thereby providing a method of stimulating or enhancing bone repair, or maintaining or increasing bone volume, bone quality, or bone strength in the body of a subject in need.

53. A method of nucleic acid delivery, comprising contacting a cell with a composite controlled release system comprising a nucleic acid adsorbed onto a basic, inorganic material and a bio-degradable polymer which yields acidic degradation products, whereby degradation of said polymer yields acidic degradation products therefrom, which stimulates dissolution of the inorganic material and release of said nucleic acid, thereby being a method of nucleic acid delivery.

* * * * *